(12) United States Patent
During et al.

(10) Patent No.: US 10,813,899 B2
(45) Date of Patent: Oct. 27, 2020

(54) USE OF (S)-3-AMINO-4-(DIFLUOROMETHYLENYL) CYCLOPENT-1-ENE-L-CARBOXYLIC ACID AND RELATED COMPOUNDS, (1S,3S)-3-AMINO-4-(DIFLUOROMETHYL-IDENE) CYCLOPENTANE-1-CARBOXYLIC ACID AND VIGABATRIN IN THE TREATMENT OF DEVELOPMENTAL DISORDERS

(71) Applicant: Ovid Therapeutics Inc., New York, NY (US)

(72) Inventors: Matthew During, Weston, CT (US); Brett Abrahams, New York, NY (US)

(73) Assignee: Ovid Therapeutics Inc., New York, NY (US)

( * ) Notice: Subject to any disclaimer, the term of this patent is extended or adjusted under 35 U.S.C. 154(b) by 0 days.

(21) Appl. No.: 16/434,300

(22) Filed: Jun. 7, 2019

(65) Prior Publication Data

US 2019/0374492 A1   Dec. 12, 2019

Related U.S. Application Data

(60) Provisional application No. 62/681,913, filed on Jun. 7, 2018.

(51) Int. Cl.
*A61K 31/197* (2006.01)
*A61P 43/00* (2006.01)

(52) U.S. Cl.
CPC .......... *A61K 31/197* (2013.01); *A61P 43/00* (2018.01)

(58) Field of Classification Search
CPC .............................. A61K 31/197; A61P 43/00
See application file for complete search history.

(56) References Cited

U.S. PATENT DOCUMENTS

| | | |
|---|---|---|
| 6,794,413 B1 | 9/2004 | Silverman et al. |
| 7,381,748 B1 | 6/2008 | Silverman et al. |
| 8,969,413 B2 | 3/2015 | Silverman et al. |
| 9,670,141 B2 | 6/2017 | Silverman et al. |
| 9,993,449 B2 | 6/2018 | Silverman et al. |
| 2012/0283323 A1 | 11/2012 | Silva et al. |
| 2013/0041028 A1 | 2/2013 | Silverman et al. |
| 2013/0230586 A1 | 9/2013 | Coelho et al. |
| 2014/0303243 A1 | 10/2014 | Hakonarson et al. |
| 2014/0336256 A1 | 11/2014 | Miller et al. |
| 2015/0224164 A1 | 8/2015 | Glass et al. |
| 2017/0101364 A1 | 4/2017 | Silverman et al. |
| 2017/0239202 A1 | 8/2017 | Silverman et al. |
| 2017/0348232 A1 | 12/2017 | During |
| 2018/0098952 A1 | 4/2018 | Silverman et al. |
| 2018/0221319 A1 | 8/2018 | During |
| 2018/0271816 A1 | 9/2018 | Silverman et al. |

FOREIGN PATENT DOCUMENTS

| | | |
|---|---|---|
| WO | 2009033818 A2 | 3/2009 |
| WO | 2015035402 A1 | 3/2015 |
| WO | 2016073983 A2 | 5/2016 |
| WO | 2017062942 A2 | 4/2017 |
| WO | 2018148380 A1 | 8/2018 |

OTHER PUBLICATIONS

Lippert, et al., "4-Amino-hex-5-enoic Acid, a Selective Catalytic Inhibitor of 4-Aminobutyric-Acid Aminotransferase in Mammalian Brain", Eur. J. Biochem,vol. 74, No. 3; Apr. 15, 1977; pp. 441-445.
Pan et al., "Design, Synthesis, and Biological Activity of a Difluoro-Substituted, Conformationally Rigid Vigabatrin Analogue as a Potent γ-Aminobutyric Acid Aminotransferase Inhibitor", Journal of Medicinal Chemistry, vol. 46, No. 25, Dec. 4, 2003;pp. 5292-5293.
International Search Report and Written Opinion of the International Searching Authority, corresponding to International Application No. PCT/US2016/056245, dated Jan. 26, 2017; 16 total pages.
Lu, et al., "Fluorinated Conformationally-Restricted γ-Aminobutyric Acid Aminotransferase Inhibitors", Journal of Medicinal Chemistry, E-Pub, vol. 49, No. 25, Oct. 11, 2006; pp. 7404-7412 and Figures 1-2.
Kanth et al., "QSAR Analysis of a Few GABA Aminotransferase Inhibitors as Potent Antiepileptics", Indian Journal of Chemistry, vol. 44B, Mar. 2005; pp. 595-599.
Chebib et al., "The Effects of Cyclopentane and Cyclopentene Analogues of GABA at Recombinant GABAC Receptors", European Journal of Pharmacology, vol. 430, No. 2-3; Nov. 2001; pp. 185-192.
Notification concerning Transmittal of International Preliminary Report on Patentability (Chapter I of the Patent Cooperation Treaty), dated Apr. 19, 2018, including International Preliminary Report on Patentability and Written OpinionInternational Search Report and Written Opinion of the International Searching Authority, corresponding to International Application No. PCT/US2016/056245; 13 total pages.
Tolman et al., "Treatement options for refractory and difficult to treat seizures: focus on vigabatrin", (Dovepress) Therapeutics and Clinical Risk Management, 2011, vol. 7; pp. 367-375.
Blume et al., ILAE Commission Report, Glossary of Descriptive Terminology for Ictal Semiology: Report of the ILAE Task Force on Classification and Terminology, Blackwell Science, Inc., International League Against Epilepsy, Epilepsia, (2001), vol. 42, No. 9; pp. 1212-1218.

(Continued)

*Primary Examiner* — Yong S. Chong
(74) *Attorney, Agent, or Firm* — Carter, DeLuca & Farrell LLP

(57) ABSTRACT

Methods and compositions for use treating Fragile X syndrome, Angelman syndrome, Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome with a compound of Formula 1 as described herein, (S)-3-amino-4-(difluoromethylenyl) cyclopent-1-ene-1-carboxylic acid, (1S,3S)-3-amino-4-(difluoromethylidene) cyclopentane-1-carboxylic acid, or vigabatrin, or pharmaceutically acceptable salts of any of the foregoing, are provided.

14 Claims, 6 Drawing Sheets

(56) References Cited

OTHER PUBLICATIONS

International Search Report and Written Opinion, dated Apr. 16, 2018, corresponding to International Application No. PCT/US2018/017382; 8 pages.
Fuchs et al., "Inhibition of GSK3ß rescues hippocampal development and learning in a mouse model of CDKL5 disorder", Neurobiology of Disease, (2015), vol. 82, pp. 298-310.
Richard B. Silverman, "The 2011 E. B. Hershberg Award for IMportant Discoveries in Medicinally Active Substances: (1S, 3S)-3-Amino-4-difluoromethylenyl-1-cyclopentanoic Acid (CPP-115), a GABA Aminotransferase Inactivator and New Treatment for Drug Addiction and Infantile Spasms," Journal of Medicinal Chemistry, (2012), vol. 55; pp. 567-575.
International Search Report and Written Opinion, dated Jun. 17, 2019, corresponding to International Application No. PCT/US2019/017201; 11 pages.
U.S. Appl. No. 16/423,761, filed May 29, 2019, to Silverman et al.
U.S. Appl. No. 16/434,300, filed Jun. 7, 2019, to Silverman et al.
Juncosa et al. "Design and Mechanism of (S)-3-Amino-4-(difluoromethylenyl)cyclopent-1-ene-1-carboxylic Acid, a Highly Potent r-Aminobutyric Acid Aminotransferase Inactivator for the Treatment of Addiction", Journal of the American Chemical Society, Jan. 30, 2018 (Jan. 30, 2018), vol. 140, pp. 2151-2164; Title, Abstract.
International Search Report and Written Opion issued in International Patent Application No. PCT/US2019/024726, dated Jun. 18, 2019 (7 pages).
Muller et al., "Restrospective evaluation of low long-term efficacy of antiepileptic drugs and ketogenic diet in 39 patients with CDKL5-related epilepsy," Official Journal of the European Paediatric Neurology Society, (2016), vol. 20; pp. 147-151.
Doumlele et al., "A case report on teh efficacy of vigabatrin analogue (1S, 3S)-3-amino-4-difluoromethylenyl-1-cyclopentanoic acid (CPP-115) in a patient with infantile spasm," Epilepsy & Behavior Case Reports (2016); pp. 67-69.
U.S. Appl. No. 16/484,595, filed Aug. 8, 2019, to During.
Notification concerning Transmittal of International Preliminary Report on Patentability (Chapter I of the Patent ooperation Treaty), dated Apr. 19, 2018, including International Preliminary Report on Patentability and Written OpinionInternationalSearch Report and Written Opinion of the International Searching Authority, corresponding to International Application No. PCT/US2016/056245; 13 total pages.
Le et al., "Design and Mechanism of Tetrahydrothiophene-Based γ-Aminobutyric Acid Aminotransferase lnactivators," Journal of the American Chemical Society, (2015), vol. 137; pp. 4525-4533.
Juncosa et al., "Desgin and and Mechanism of (S)-3-Amino-4-(difluoromethylenyl)cyclopent-1-ene-1-carboxylic Acid, a Highly Potent γ-Aminobutyric Acid Aminotransferase Inactivator for the Treatment of Addiction," Journal of the American Cbemical Society (2018), vol. 140; pp. 2151-2164.
Qiu et al., "A New Class of Conformationally Rigid Anallogues of 4-Amino-5-halopentanoic Acids, Potent Inactivators of γ-Aminobutyric Acid Aminotransferase," J. Med. Chem. (2000), vol. 43; pp. 706-720.
Zhao et al., "Difluoromethyl 2-Pyridyl Sulfone: A New gem-Difluoroolefination Reagent for Aldehydes and Ketones,"—Organic Letters (2010), vol. 12, No. 7; pp. 1444-1447.
International Search Report and Written Opinion of the International Searching Authority, dated Oct. 7, 2019, corresponding to International Application No. PCT/US2019/035934; 12 pages.

**** p<0.0001

**** p<0.0001

*** p = 0.0003
**** p<0.0001

**** p<0.0001

USE OF (S)-3-AMINO-4-(DIFLUOROMETHYLENYL) CYCLOPENT-1-ENE-L-CARBOXYLIC ACID AND RELATED COMPOUNDS, (1S,3S)-3-AMINO-4-(DIFLUOROMETHYLI-DENE) CYCLOPENTANE-1-CARBOXYLIC ACID AND VIGABATRIN IN THE TREATMENT OF DEVELOPMENTAL DISORDERS

CROSS-REFERENCE TO RELATED APPLICATION

This application claims benefit and priority to U.S. Provisional Application No. 62/681,913, filed Jun. 7, 2018, which is incorporated herein by reference in its entirety.

TECHNICAL FIELD

Methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome with (S)-3-amino-4-(difluoromethylenyl) cyclopent-1-ene-1-carboxylic acid, related compounds, (1S, 3S)-3-amino-4-(difluoromethylidene) cyclopentane-1-carboxylic acid, vagabatrin, or pharmaceutically acceptable salts of any of the foregoing.

BACKGROUND

Developmental disorders include Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, and Jacobsen syndrome. Treatments for these disorders are limited.

Angelman syndrome is a neurodevelopmental disorder caused by loss of function of the UBE3A gene encoding a ubiquitin E3 ligase. Characteristic features of this disorder include delayed development, intellectual disability, and severe speech impairment. Motor dysfunction is a characteristic feature of Angelman syndrome, e.g., problems with movement and balance (ataxia). M but neither the mechanisms of action nor effective therapeutic strategies have yet been elucidated.

Fragile X syndrome may be the most common genetic cause of intellectual disability and the most common single-gene cause of autism. It is caused by mutations on the fragile X mental retardation gene (FMR1) and lack of fragile X mental retardation protein, which in turn, leads to decreased inhibition of translation of many synaptic proteins. The main efforts have focused on metabotropic glutamate receptor (mGluR) targeted treatments; however, investigation on the gamma-aminobutyric acid (GABA) system and its potential as a targeted treatment is less emphasized. The fragile X mouse models (Fmr1-knock out) show decreased GABA subunit receptors, decreased synthesis of GABA, increased catabolism of GABA, and overall decreased GABAergic input in many regions of the brain. These symptoms are also observed in individuals with autism and other neurodevelopmental disorders, therefore the targeted treatments for Fragile X syndrome are leading the way in the treatment of other neurodevelopmental syndromes and autism. Potential GABAergic treatments have been discussed. However, further studies are needed to determine the safety and efficacy of GABAergic treatments for Fragile X syndrome.

Fragile X-associated tremor/ataxia syndrome (FXTAS) is a late-onset disorder, usually occurring after age 50. Mutations in the FMR1 gene increase the risk of developing FXTAS. The mutation relates to a DNA segment known as a CGG triplet repeat which is expanded within the FMR1 gene. Normally, this DNA segment is repeated from 5 to about 40 times. In people with FXTAS the CGG segment may be repeated 55 to 200 times. This mutation is known as an FMR1 gene premutation. An expansion of more than 200 repeats, a full mutation, causes Fragile X syndrome discussed above. FXTAS is typically characterized by problems with movement and thinking ability (cognition). FXTAS signs and symptoms usually worsen with age. Affected individuals have areas of damage in the cerebellum, the area of the brain that controls movement. Characteristic features of FXTAS are intention tremor, which is trembling or shaking of a limb when trying to perform a voluntary movement such as reaching for an object, and problems with coordination and balance (ataxia). Many affected individuals develop other movement problems, such as parkinsonism, which includes tremors when not moving (resting tremor), rigidity, and unusually slow movement (bradykinesia). In addition, affected individuals may have reduced sensation, numbness or tingling, pain, or muscle weakness in the lower limbs, and inability to control the bladder or bowel. Other symptoms may include chronic pain syndromes, such as fibromyalgia and chronic migraine, hypothyroidism, hypertension, insomnia, sleep apnea, vertigo, olfactory dysfunction, and hearing loss. People with FXTAS commonly have cognitive disabilities such as short-term memory loss and loss of executive function, which is the ability to plan and implement actions and develop problem-solving strategies. Loss of this function impairs skills such as impulse control, self-monitoring, focusing attention appropriately, and cognitive flexibility. Many people with FXTAS experience psychiatric symptoms such as anxiety, depression, moodiness, or irritability.

There is currently no targeted therapeutic intervention that can arrest or reverse the pathogenesis of FXTAS. However a number of treatment approaches of potential symptomatic benefit have been suggested. Primidone, beta-blockers such as propanolol, topiramate, carbidopa/levodopa, and benzodiazepines have been suggested to control tremors associated with FXTAS; botulinum toxin for involuntary muscle activities, such as dystonia and spasticity; carbidopa/levodopa, amantadine and buspirone for ataxia; cholinesterase inhibitors such as donepezil, and memantine (an NMDA antagonist) for cognitive deficits and dementia; and antidepressants and antipsychotics for psychiatric symptoms. See, e.g., Hagerman, et al., Clin Interv Aging. 2008 June; 3(2): 251-262.

Autism spectrum disorder (ASD) is a developmental disorder that affects communication and behavior. Symptoms generally appear in the first two years of life. According to the Diagnostic and Statistical Manual of Mental Disorders (DSM-5), people with ASD may have: difficulty with communication and interaction with other people, restricted interests and repetitive behaviors, symptoms that hurt the person's ability to function properly in school, work, and other areas of life. Autism is known as a "spectrum" disorder because there is wide variation in the type and severity of symptoms people experience. Social communication/interaction behaviors may include: making little or inconsistent eye contact, tending not to look at or listen to people, rarely sharing enjoyment of objects or activities by pointing or showing things to others, failing to, or being slow to, respond to someone calling their name or to other verbal attempts to gain attention, having difficulties with the back and forth of conversation, often talking at length about a favorite subject without noticing that others are not interested or without giving others a chance to respond, having facial expressions, movements, and gestures that do not match what is being said, having an unusual tone of voice that may sound sing-song or flat and robot-like, having trouble understanding another person's point of view or being unable to predict or understand other people's actions. Restrictive/repetitive behaviors may include: repeating certain behaviors or having unusual behaviors, e.g., repeating words or phrases, a behavior called echolalia, having a lasting intense interest in certain topics, such as numbers, details, or facts, having overly focused interests, such as with moving objects or parts of objects, getting upset by slight changes in a routine, being more or less sensitive than other people to sensory input, such as light, noise, clothing, or temperature, people with ASD may also experience sleep problems and irritability. Although ASD can be a lifelong disorder, treatments and services can improve a person's symptoms and ability to function.

Asperger's syndrome (AS) is a developmental disorder classified within ASD, but characterized by a relatively high level of functioning. Individuals with Asperger syndrome exhibit impairment in social interaction and a repetitive, stereotyped pattern of behavior. The individual, however, displays no delay in language or cognitive development, which differentiates Asperger Syndrome from other aspects of autism. A distinguishing symptom of AS is a child's obsessive interest in a single object or topic to the exclusion of any other. Children with AS want to know everything about their topic of interest and their conversations with others will be about little else. Other characteristics of AS include repetitive routines or rituals; peculiarities in speech and language; socially and emotionally inappropriate behavior and the inability to interact successfully with peers; problems with non-verbal communication; and clumsy and uncoordinated motor movements.

Pervasive developmental disorder not otherwise specified (PDD-NOS) is a developmental disorder classified within ASD in which symptoms can vary widely from one child to the next. Overall, children with PDD-NOS can be characterized as having impaired social interaction, better language skills than children with autism but not as good as those with Asperger's syndrome, fewer repetitive behaviors than children with Asperger's syndrome or autism, and a possible later age of onset. Symptoms of PDD-NOS may include behavioral and communication problems such as difficulty using and understanding language, difficulty relating to people, objects, and events, e.g., lack of eye contact, pointing behavior, and lack of facial responses, unusual play with toys and other objects, difficulty with changes in routine or familiar surroundings, repetitive body movements or behavior patterns, such as hand flapping, hair twirling, foot tapping, or more complex movements, inability to cuddle or be comforted, difficulty regulating behaviors and emotions, which may result in temper tantrums, anxiety, and aggression, and emotional breakdowns.

Childhood disintegrative disorder (CDD) is a developmental disorder in which children develop normally through age 3 or 4. Then, over a few months, they lose language, motor, social, and other skills that they already learned. CDD has some similarity to autism, and may sometimes be considered a low-functioning form of autism. Typically, between the ages of 2 and 10, skills previously acquired are lost almost completely in at least two of the following six functional areas: 1. Expressive language skills, 2. receptive language skills, i.e., comprehension of language, 3. social skills and self-care skills, 4. bowel and bladder control, 5. play skills, and 6. motor skills. Lack of normal function or impairment also occurs in at least two of the following three areas: 1. social interaction, 2. communication, and 3. repetitive behavior and interest patterns.

Williams syndrome is a developmental disorder that affects many parts of the body. This condition is characterized by mild to moderate intellectual disability or learning problems, unique personality characteristics, distinctive facial features, and heart and blood vessel (cardiovascular) problems. People with Williams syndrome typically have difficulty with visual-spatial tasks such as drawing and assembling puzzles, but they tend to do well on tasks that involve spoken language, music, and learning by repetition (rote memorization). Affected individuals have outgoing, engaging personalities and tend to take an extreme interest in other people. Attention deficit disorder (ADD), problems with anxiety, and phobias are common among people with this disorder. Young children with Williams syndrome have distinctive facial features including a broad forehead, a short nose with a broad tip, full cheeks, and a wide mouth with full lips. Many affected people have dental problems such as teeth that are small, widely spaced, crooked, or missing. In older children and adults, the face appears longer and more gaunt. Supravalvular aortic stenosis occurs frequently in people with Williams syndrome. Additional signs and symptoms of Williams syndrome include abnormalities of connective tissue such as joint problems and soft, loose skin. Affected people may also have increased calcium levels in the blood in infancy, developmental delays, problems with coordination, and short stature.

Jacobsen syndrome is a developmental disorder caused by a loss of genetic material from chromosome 11. Because this deletion occurs at the end (terminus) of the long (q) arm of chromosome 11, Jacobsen syndrome is also known as 11q terminal deletion disorder. The signs and symptoms of Jacobsen syndrome vary considerably. Most affected individuals have delayed development, including delays in the development of speech and motor skills (such as sitting, standing, and walking). Most also have cognitive impairment and learning difficulties. Behavioral problems have been reported, including compulsive behavior (such as shredding paper), a short attention span, and easy distractibility. Many people with Jacobsen syndrome have been diagnosed with attention deficit-hyperactivity disorder (ADHD). Jacobsen syndrome is also associated with an increased likelihood of autism spectrum disorders. Jacobsen syndrome is also characterized by distinctive facial features. These include small and low-set ears, widely set eyes (hypertelorism) with droopy eyelids (ptosis), skin folds covering the inner corner of the eyes (epicanthalfolds), a broad nasal bridge, downturned corners of the mouth, a thin upper lip, and a small lower jaw. Affected individuals often have a large head size (macrocephaly) and a skull abnormality called trigonocephaly, which gives the forehead a pointed appearance. Many people with Jacobsen syndrome have a bleeding disorder called Paris-Trousseau syndrome. This condition causes a lifelong risk of abnormal bleeding and easy bruising. Other features of Jacobsen syndrome can include heart defects, feeding difficulties in infancy, short stature, frequent ear and sinus infections, and skeletal abnormalities. The disorder can also affect the digestive system, kidneys, and genitalia.

There remains a need for effective treatments of patients with developmental disorders such as Autism Spectrum Disorder, Asperger's syndrome, pervasive developmental disorder not otherwise specified, Angelman syndrome, Fragile X syndrome, Fragile X-associated tremor/ataxia syndrome (FXTAS), Childhood Disintegrative Disorder, Williams Syndrome, and Jacobsen syndrome.

SUMMARY

Methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome are provided.

In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering (S)-3-amino-4-(difluoromethylenyl)cyclopent-1-ene-1-carboxylic acid or a pharmaceutically acceptable salt thereof to a subject in need thereof to provide improvement in one or more symptoms of the disorder. In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering (S)-3-amino-4-(difluoromethylenyl)cyclopent-1-ene-1-carboxylic acid or a pharmaceutically acceptable salt thereof to a subject in need thereof to provide improvement in next day functioning of the subject.

In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering to a subject in need thereof an effective amount of (1S,3S)-3-amino-4-(difluoromethylidene)cyclopentane-1-carboxylic acid or a pharmaceutically acceptable salt thereof. In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering (1S,3S)-3-amino-4-(difluoromethylidene)cyclopentane-1-carboxylic acid or a pharmaceutically acceptable salt thereof to a subject in need thereof to provide improvement in one or more symptoms of the disorder. In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering (1S,3S)-3-amino-4-(difluoromethylidene)cyclopentane-1-carboxylic acid or a pharmaceutically acceptable salt thereof to a subject in need thereof to provide improvement in next day functioning of the subject.

In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering to a subject in need thereof an effective amount of vigabatrin ((RS)-4-aminohex-5-enoic acid) or a pharmaceutically acceptable salt thereof. In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering vigabatrin ((RS)-4-aminohex-5-enoic acid) or a pharmaceutically acceptable salt thereof to a subject in need thereof to provide improvement in one or more symptoms of the disorder. In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering vigabatrin ((RS)-4-aminohex-5-enoic acid) or a pharmaceutically acceptable salt thereof to a subject in need thereof to provide improvement in next day functioning of the subject.

In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering to a subject in need thereof an effective amount of Formula I or a pharmaceutically acceptable salt thereof. In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering Formula I or a pharmaceutically acceptable salt thereof to a subject in need thereof to provide improvement in one or more symptoms of the disorder. In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering Formula I or a pharmaceutically acceptable salt thereof to a subject in need thereof to provide improvement in next day functioning of the subject.

In embodiments, methods of treating developmental disorders including Autism Spectrum Disorder, pervasive developmental disorder not otherwise specified, Angelman syndrome, Fragile X syndrome, Fragile X-associated tremor/ataxia syndrome (FXTAS), Asperger's syndrome, Childhood Disintegrative Disorder, Williams Syndrome, and Jacobsen syndrome include administering two or more of: (S)-3-amino-4-(difluoromethylenyl)cyclopent-1-ene-1-carboxylic acid or a pharmaceutically acceptable salt thereof, a compound according to Formula I or a pharmaceutically acceptable salt thereof, (1S,3S)-3-amino-4-(difluoromethylidene)cyclopentane-1-carboxylic acid or a pharmaceutically acceptable salt thereof, or vigabatrin ((RS)-4-aminohex-5-enoic acid) or a pharmaceutically acceptable salt thereof, to a subject in need thereof.

DETAILED DESCRIPTION

Figure 1:
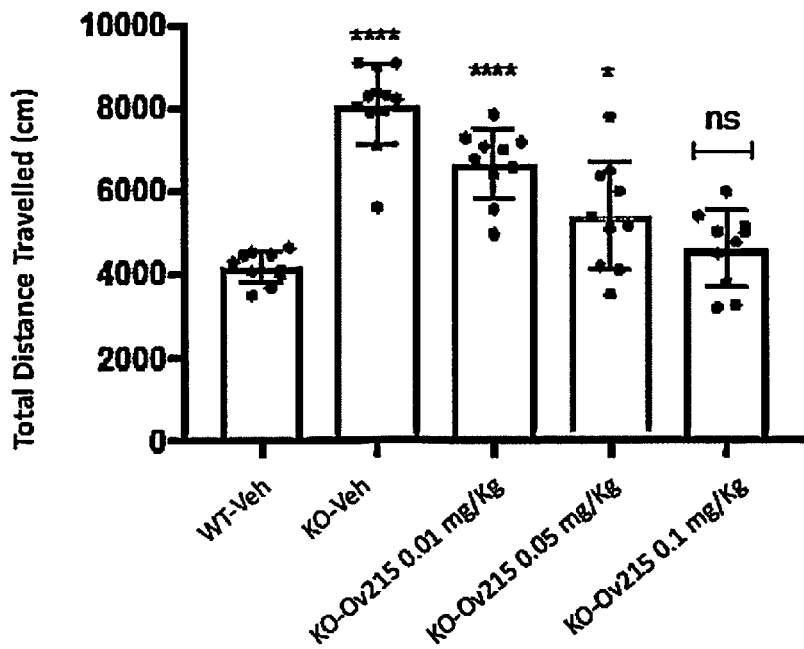
FIG. 1 is a bar graph illustrating open field locomotive activity (total distance traveled) of wild-type mice administered 0.5% methyl cellulose vehicle, Fmr1 KO2 mice administered 0.5% methyl cellulose vehicle, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

Methods of treating a developmental disorder herein are provided and, in embodiments, include administering to a subject in need thereof an effective amount of (S)-3-amino-4-(difluoromethylenyl)cyclopent-1-ene-1-carboxylic acid or a pharmaceutically acceptable salt thereof. In embodiments, methods of treating a developmental disorder include administering (S)-3-amino-4-(difluoromethylenyl)cyclopent-1-ene-1-carboxylic acid or a pharmaceutically acceptable salt thereof to a subject in need thereof to provide improvement in one or more symptoms of the disorder. In embodiments, methods of treating developmental disorder include administering (S)-3-amino-4-(difluoromethylenyl) cyclopent-1-ene-1-carboxylic acid or a pharmaceutically acceptable salt thereof to a subject in need thereof to provide improvement in next day functioning of the subject.

Methods of treating a developmental disorder herein are provided and, in embodiments, include administering to a subject in need thereof an effective amount of (1S,3S)-3-amino-4-(difluoromethylidene)cyclopentane-1-carboxylic acid or a pharmaceutically acceptable salt thereof. In embodiments, methods of treating a developmental disorder include administering (1S,3S)-3-amino-4-(difluoromethylidene)cyclopentane-1-carboxylic acid or a pharmaceutically acceptable salt thereof to a subject in need thereof to provide improvement in one or more symptoms of the disorder. In embodiments, methods of treating a developmental disorder include administering (1S,3S)-3-amino-4-(difluoromethylidene)cyclopentane-1-carboxylic acid or a pharmaceutically acceptable salt thereof to a subject in need thereof to provide improvement in next day functioning of the subject.

In embodiments, methods of treating a developmental disorder herein include administering to a subject in need thereof an effective amount of vigabatrin ((RS)-4-aminohex-5-enoic acid) or a pharmaceutically acceptable salt thereof. In embodiments, methods of treating a developmental disorder include administering vigabatrin ((RS)-4-aminohex-5-enoic acid) or a pharmaceutically acceptable salt thereof to a subject in need thereof to provide improvement in one or more symptoms of the disorder. In embodiments, methods of treating a developmental disorder include administering vigabatrin ((RS)-4-aminohex-5-enoic acid) or a pharmaceutically acceptable salt thereof to a subject in need thereof to provide improvement in next day functioning of the subject.

In embodiments, methods and compositions herein involve compounds according to Formula I:

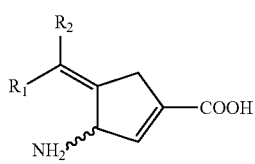

I wherein R$_1$ and R$_2$ can be independently selected from H, F, Cl, Br and I, where at least one of R$_1$ and R$_2$ is not H, or a salt of such a compound. Without limitation, in embodiments, the stereocenter including an amino substituent can have an (S) stereochemical configuration.

Accordingly, methods of treating a developmental disorder herein are provided and, in embodiments, include administering to a subject in need thereof an effective amount of a compound according to Formula I or a pharmaceutically acceptable salt thereof. In embodiments, methods of treating a developmental disorder include a compound according to Formula I or a pharmaceutically acceptable salt thereof to a subject in need thereof to provide improvement in one or more symptoms of the disorder. In embodiments, methods of treating developmental disorder include administering a compound according to Formula I or a pharmaceutically acceptable salt thereof to a subject in need thereof to provide improvement in next day functioning of the subject.

In embodiments, methods of treating a developmental disorder herein include administering two or more of: (S)-3-amino-4-(difluoromethylenyl)cyclopent-1-ene-1-carboxylic acid or a pharmaceutically acceptable salt thereof, (1S,3S)-3-amino-4-(difluoromethylidene)cyclopentane-1-carboxylic acid or a pharmaceutically acceptable salt thereof, and vigabatrin ((RS)-4-aminohex-5-enoic acid) or a pharmaceutically acceptable salt thereof, to a subject in need thereof.

The structure of (S)-3-amino-4-(difluoromethylenyl)cyclopent-1-ene-1-carboxylic acid may be represented as follows:

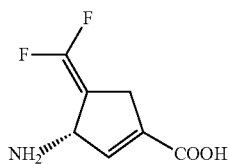 [SMILES: N[C@H]1C=C(C(=O)O)CC1=C(F)F]

The structure of (1S,3S)-3-amino-4-(difluoromethylidene)cyclopentane-1-carboxylic acid may be represented as follows:

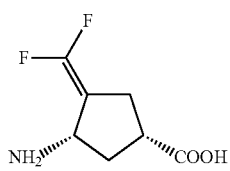

The structure of vigabatrin, also known as gamma-vinyl-GABA, also known as (RS)-4-aminohex-5-enoic acid, may be represented as follows:

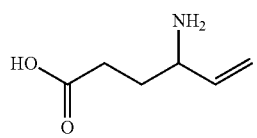

In embodiments, (S)-3-amino-4-(difluoromethylenyl)cyclopent-1-ene-1-carboxylic acid may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-aminobenzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, (1S,3S)-3-amino-4-(difluoromethylidene)cyclopentane-1-carboxylic acid may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, vigabatrin may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, a compound according to Formula I may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, pantothenic, p-amino-benzoic, glutamic, benzene sulfonic or theophylline acetic acid addition salts, as well as the 8-halotheophyllines, for example 8-bromo-theophylline. In embodiments, inorganic acid addition salts, including but not limited to, hydrochloric, hydrobromic, hydroiodic, sulfuric, sulfamic, phosphoric or nitric acid addition salts may be used.

In embodiments, the developmental disorder is Autism Spectrum Disorder, pervasive developmental disorder not otherwise specified, Asperger's syndrome, Angelman syndrome, Fragile X syndrome, Fragile X-associated tremor/ataxia syndrome (FXTAS), Childhood Disintegrative Disorder, Williams Syndrome, or Jacobsen syndrome. In embodiments, the developmental disorder is Fragile X syndrome. In embodiments, the developmental disorder is Angelman syndrome. In embodiments, the developmental disorder is Fragile X-associated tremor/ataxia syndrome (FXTAS). In embodiments, the developmental disorder is autism spectrum disorder. In embodiments, the developmental disorder is Asperger's syndrome. In embodiments, the developmental disorder is a pervasive developmental disorder not otherwise specified (PDD-NOS). In embodiments, the developmental disorder is childhood disintegrative disorder. In embodiments, the developmental disorder is Williams syndrome. In embodiments, the developmental disorder is Jacobsen syndrome.

In embodiments, symptoms of Angelman syndrome include delayed development, intellectual disability, cognitive impairment, uncontrolled laughter, excitability, severe speech impairment, hand flapping, and/or motor dysfunction, e.g., problems with movement and balance (ataxia).

In embodiments, symptoms of Fragile X syndrome include intellectual disability, cognitive impairment, attention disorders, hyperactivity, anxiety, language-processing problems, lack of eye contact, trouble speaking clearly, stuttering, and/or sensitivity to sensory input such as bright light or loud noises.

In embodiments, symptoms of Fragile X-associated tremor/ataxia syndrome include intention tremor, problems with coordination and balance (ataxia), parkinsonism, reduced sensation, numbness or tingling, pain, or muscle weakness in the lower limbs, inability to control the bladder or bowel, chronic pain syndromes, fibromyalgia, chronic migraine, hypothyroidism, hypertension, insomnia, sleep apnea, vertigo, olfactory dysfunction, hearing loss, cognitive impairment, short-term memory loss, loss of executive function, impulse control, self-monitoring, focusing attention appropriately, cognitive impairment, cognitive flexibility, and/or psychiatric symptoms such as anxiety, depression, moodiness, or irritability.

In embodiments, symptoms of autism spectrum disorder include difficulty with communication and interaction with other people, restricted interests and repetitive behaviors, making little or inconsistent eye contact, tending not to look at or listen to people, rarely sharing enjoyment of objects or activities by pointing or showing things to others, failing to, or being slow to, respond to someone calling their name or to other verbal attempts to gain attention, having difficulties with the back and forth of conversation, often talking at length about a favorite subject without noticing that others are not interested or without giving others a chance to respond, having facial expressions, movements, and gestures that do not match what is being said, having an unusual tone of voice that may sound sing-song or flat and robot-like, having trouble understanding another person's point of view or being unable to predict or understand other people's actions, repeating certain behaviors or having unusual behaviors, e.g., echolalia, having a lasting intense interest in certain topics, such as numbers, details, or facts, having overly focused interests, such as with moving objects or parts of objects, getting upset by slight changes in a routine, being more or less sensitive than other people to sensory input, such as light, noise, clothing, or temperature, sleep problems cognitive impairment and/or irritability.

In embodiments, symptoms of PDD-NOS include behavioral and communication problems such as difficulty using and understanding language, difficulty relating to people, objects, and events, e.g., lack of eye contact, pointing behavior, and lack of facial responses, unusual play with toys and other objects, difficulty with changes in routine or familiar surroundings, cognitive impairment, repetitive body movements or behavior patterns, such as hand flapping, hair twirling, foot tapping, or more complex movements, inability to cuddle or be comforted, difficulty regulating behaviors and emotions, temper tantrums, anxiety, aggression, and/or emotional breakdowns.

In embodiments, symptoms of childhood disintegrative disorder include, loss of language, motor, social, and other skills previously learned including loss of one or more of: 1. expressive language skills, 2. receptive language skills, i.e., comprehension of language, 3. social skills and self-care skills, 4. bowel and bladder control, 5. play skills, and 6. motor skills, 7. social interaction, and 8. communication. CDD subjects may demonstrate autistic symptoms, e.g., cognitive impairment, repetitive behavior and interest patterns, etc.

In embodiments, symptoms of Williams syndrome include mild to moderate intellectual disability or learning problems, cognitive impairment, unique personality characteristics, distinctive facial features, heart and blood vessel (cardiovascular) problems, difficulty with visual-spatial tasks such as drawing and assembling puzzles, attention deficit disorder (ADD), problems with anxiety and phobias, developmental delays, problems with coordination, and/or short stature.

In embodiments, symptoms of Jacobsen syndrome include delayed development, including delays in the development of speech and motor skills (such as sitting, standing, and walking), cognitive impairment, learning difficulties, compulsive behavior, short attention span, easy distractibility, attention deficit-hyperactivity disorder (ADHD, autism, and/or feeding difficulties in infancy.

Cognitive impairment in developmental disorders herein may be measured against normal cognitive function, which refers to the normal physiologic activity of the brain, including, but not limited to, one or more of the following: mental stability, memory/recall abilities, problem solving abilities, reasoning abilities, thinking abilities, judging abilities, ability to discriminate or make choices, capacity for learning, ease of learning, perception, intuition, attention, and awareness, as measured by any criteria suitable in the art.

Cognitive impairment may also include deficits in mental activities that are mild or that otherwise do not significantly interfere with daily life. Mild cognitive impairment (MCI) is an example of such a condition. A subject with mild cognitive impairment may display symptoms of dementia (e.g., difficulties with language or memory) but the severity of these symptoms is such that a diagnosis of dementia may not be appropriate.

One skilled in the art will appreciate that there are numerous human and animal models that may be used to evaluate and compare the relative safety and efficacy of (S)-3-amino-4-(difluoromethylenyl)cyclopent-1-ene-1-carboxylic acid, (1S,3S)-3-amino-4-(difluoromethylidene)cyclopentane-1-carboxylic acid, a compound according to Formula I, or vigabatrin in connection with the treatment of the developmental disorders discussed above. In humans, cognitive function may be measured, for example and without limitation, by the clinical global impression of change scale (CGI); the Mini Mental State Exam (MMSE) (aka the Folstein Test); the Neuropsychiatric Inventory (NPI); the Clinical Dementia Rating Scale (CDR); the Cambridge Neuropsychological Test Automated Battery (CANTAB), the Sandoz Clinical Assessment-Geriatric (SCAG) scale, the Benton Visual Retention Test (BVRT), Montreal Cognitive Assessment (MoCA) or Digit Symbol Substitution Test (DSST).

In animal model systems, cognitive function may be measured in various conventional ways known in the art, including using a Morris Water Navigation Task, Barnes maze, radial arm maze task, T maze and the like. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

An effective amount of (S)-3-amino-4-(difluoromethylenyl)cyclopent-1-ene-1-carboxylic acid or a pharmaceutically acceptable salt thereof is used to respectively treat a subject having Autism Spectrum Disorder, pervasive developmental disorder not otherwise specified, Asperger's syndrome, Angelman syndrome, Fragile X syndrome, Fragile X-associated tremor/ataxia syndrome (FXTAS), Childhood Disintegrative Disorder, Williams Syndrome, or Jacobsen syndrome. An effective amount of a compound according to Formula I or a pharmaceutically acceptable salt thereof is used to respectively treat a subject having Autism Spectrum Disorder, pervasive developmental disorder not otherwise specified, Asperger's syndrome, Angelman syndrome, Fragile X syndrome, Fragile X-associated tremor/ataxia syndrome (FXTAS), Childhood Disintegrative Disorder, Williams Syndrome, or Jacobsen syndrome. An effective amount of (1S,3S)-3-amino-4-(difluoromethylidene)cyclopentane-1-carboxylic acid or a pharmaceutically acceptable salt thereof is used to respectively treat a subject having Autism Spectrum Disorder, pervasive developmental disorder not otherwise specified, Asperger's syndrome, Angelman syndrome, Fragile X syndrome, Fragile X-associated tremor/ataxia syndrome (FXTAS), Childhood Disintegrative Disorder, Williams Syndrome, or Jacobsen syndrome. An effective amount of vigabatrin ((RS)-4-aminohex-5-enoic acid) or a pharmaceutically acceptable salt thereof is used to respectively treat a subject having Autism Spectrum Disorder, pervasive developmental disorder not otherwise specified, Asperger's syndrome, Angelman syndrome, Fragile X syndrome, Fragile X-associated tremor/ataxia syndrome (FXTAS), Childhood Disintegrative Disorder, Williams Syndrome, or Jacobsen syndrome.

The subject may be an animal, e.g., mammal, e.g., rodents, humans, etc. As used herein, the terms "treat", "treatment" or "treating" encompass any manner in which symptoms or pathology of a condition, disorder or disease associated with Autism Spectrum Disorder, pervasive developmental disorder not otherwise specified, Asperger's syndrome, Angelman syndrome, Fragile X syndrome, Fragile X-associated tremor/ataxia syndrome (FXTAS), Childhood Disintegrative Disorder, Williams Syndrome, or Jacobsen syndrome are ameliorated or otherwise beneficially altered. In embodiments, "treat", "treatment" or "treating" can refer to inhibiting a disease or condition, e.g., arresting or reducing its development or at least one clinical or subclinical symptom thereof. In embodiments, "treat", "treatment" or "treating" can refer to relieving the disease or condition, e.g., causing regression of the disease or condition or at least one of its clinical or subclinical symptoms. In embodiments, "treating cognitive impairment" means ameliorating, beneficially altering and/or providing relief from one or more of the symptoms of cognitive impairment. The benefit to a subject being treated may be statistically significant, mathematically significant, or at least perceptible to the subject and/or the physician.

In embodiments, the terms "effective amount" or "therapeutically effective amount" refer to an amount of a compound, material, composition, medicament, or other material that is effective to achieve a particular pharmacological and/or physiologic effect in connection with symptoms of a developmental disorder herein such as, but not limited to, one or more of the following: reducing or eliminating difficulty in sucking, reducing or eliminating difficulty in feeding, reducing or eliminating motor dysfunction, reducing or eliminating poor muscle tone, reducing or eliminating hand flapping, increasing motor skills, increasing coordination, increasing bladder control, reducing or eliminating parkinsonism, reducing or eliminating repetitive body movements, reducing or eliminating intellectual disability, reducing or eliminating learning disability, reducing or eliminating delayed speech development, reducing or eliminating delayed language development, reducing or eliminating language processing problems, reducing or eliminating stuttering, reducing or eliminating loss of executive function, reducing or eliminating cognitive rigidity, reducing or eliminating emotional lability, enhancing impulse control, reducing or eliminating anxiety, reducing or eliminating hyperactivity, reducing or eliminating aggressive behavior, reducing or eliminating temper tantrums, reducing or eliminating uncontrolled laughter, reducing or eliminating obsessive-compulsive behavior, reducing or eliminating autistic symptomology, reducing or eliminating psychotic episodes, reducing or eliminating sleep disturbances, reducing or eliminating reduced pain sensitivity, reducing or eliminating reduced sensation, reducing or eliminating pain, reducing or eliminating fibromyalgia, reducing or eliminating chronic migraine, reducing or eliminating insomnia, reducing or eliminating vertigo, reducing or eliminating sensitivity to sensory input, reducing or eliminating cognitive impairment, enhancing cognitive function, increasing daytime activity, improving learning (either the rate or ease of learning), improving attention, improving social behavior, reducing or eliminating lack of eye contact, and/or improving cerebrovascular function. In embodiments, effective amount refers to an amount which may be suitable to prevent a decline in any one or more of the above qualities, or, in embodiments, to improve any one or more of the above qualities, for example, cognitive function or performance, learning rate or ability, problem solving ability, attention span and ability to focus on a task or problem, social behavior, and the like. Such effectiveness may be achieved, for example, by administering compositions described herein to an individual or to a population. In embodiments, the reduction, or delay of such a decline, or the improvement in an individual or population can be relative to a cohort, e.g., a control subject or a cohort population that has not received the treatment, or been administered the composition or medicament.

The dosage amount can vary according to a variety of factors such as subject-dependent variables (e.g., age, immune system, health, etc.), the disease or disorder being treated, as well as the route of administration and the pharmacokinetics of the agent being administered.

Many pharmaceutical products are administered as a fixed dose, at regular intervals, to achieve therapeutic efficacy. Duration of action is typically reflected by a drug's plasma half-life. Since efficacy is often dependent on sufficient exposure within the central nervous system administration of CNS drugs with a short half-life may require frequent maintenance dosing. The plasma elimination half-life of (1S,3S)-3-amino-4-(difluoromethylidene)cyclopentane-1-carboxylic acid is between about 4 to 6 hours. $C_{max}$ increases in a dose proportional manner over a range of 5 mg-500 mg; whereas there is a greater than proportional increase in AUCs in the dose range. (S)-3-amino-4-(difluoromethylenyl)cyclopent-1-ene-1-carboxylic acid is between 9 and 10 times more potent as an inactivator of GABA-AT than (1S,3S)-3-amino-4-(difluoromethylidene)cyclopentane-1-carboxylic acid and may exhibit similar pharmacokinetics. Vigabatrin ((RS)-4-aminohex-5-enoic acid) is rapidly absorbed, reaching peak concentrations within about 1 to 2.5 hours. Administration of a single 37-50 mg/kg dose of an oral solution of vigabatrin results in a $t_{max}$ of approximately 2.5 hours in neonates and infants, and 1 hour in children. Area under plasma concentration-time curves indicated dose-linear pharmacokinetics. Despite the lack of protein binding, cerebrospinal concentrations of vigabatrin are 10% of the plasma concentration 6 h after a single oral dose. The half-life of vigabatrin is between about 5 and 8 hours. The terminal half-life of vigabatrin is about 5.7 hours for infants (5 months-2 years), 9.5 hours for children (10 years-16 years), and 10.5 hours for adults.

In embodiments, methods include treating Autism Spectrum Disorder by administering to a subject in need thereof about 0.001 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of Autism Spectrum Disorder. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Autism Spectrum Disorder may include (S)-3-amino-4-(difluoromethylenyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Autism Spectrum Disorder once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Autism Spectrum Disorder can be about 0.5 to 50 mg per day or 1 mg to 10 mg per day and can be increased to 75 mg per day. Dosages can be lower for infants and children than for adults. In embodiments, an infant or pediatric dose for treating Autism Spectrum Disorder can be from about 0.01 to 10 mg per day once or in 2, 3 or 4 divided doses. In embodiments, a pediatric dose for treating Autism Spectrum Disorder can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with Autism Spectrum Disorder via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Autism Spectrum Disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Autism Spectrum Disorder for more than 1 hour after administration to the subject. In embodiments, methods of treating Autism Spectrum Disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Autism Spectrum Disorder for more than 2 hours after administration to the subject. In embodiments, methods of treating Autism Spectrum Disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Autism Spectrum Disorder for more than 3 hours after administration to the subject. In embodiments, methods of treating Autism Spectrum Disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Autism Spectrum Disorder for more than 4 hours after administration to the subject. In embodiments, methods of treating Autism Spectrum Disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Autism Spectrum Disorder for more than 6 hours after administration to the subject. In embodiments, methods of treating Autism Spectrum Disorder are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Autism Spectrum Disorder for more than 8, 10, 12, 14, 16, 18, 20, 22 or 24 hours after administration to the subject. In embodiments, the pharmaceutical compositions provide improvement of next day functioning of the subject with Autism Spectrum Disorder. For example, the pharmaceutical compositions may provide improvement in one or more symptoms of Autism Spectrum Disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having Autism Spectrum Disorder in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Autism Spectrum Disorder in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Autism Spectrum Disorder simultaneously or at spaced apart intervals.

In embodiments, methods include treating pervasive developmental disorder not otherwise specified (PDD-NOS) by administering to a subject in need thereof about 0.001 mg to about 750 mg of (S)-3-amino-4-(difluoromethylenyl) cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of PDD-NOS. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating PDD-NOS may include (S)-3-amino-4-(difluoromethylenyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with PDD-NOS once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating PDD-NOS can be about 0.5 to 50 mg per day or 1 mg to 10 mg per day and can be increased to 75 mg per day. Dosages can be lower for infants and children than for adults. In embodiments, an infant or pediatric dose for treating PDD-NOS can be from about 0.01 to 10 mg per day once or in 2, 3 or 4 divided doses. In embodiments, a pediatric dose for treating PDD-NOS can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with PDD-NOS via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating PDD-NOS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of PDD-NOS for more than 1 hour after administration to the subject. In embodiments, methods of treating PDD-NOS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of PDD-NOS for more than 2 hours after administration to the subject. In embodiments, methods of treating PDD-NOS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of PDD-NOS for more than 3 hours after administration to the subject. In embodiments, methods of treating PDD-NOS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of PDD-NOS for more than 4 hours after administration to the subject. In embodiments, methods of treating PDD-NOS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of PDD-NOS for more than 6 hours after administration to the subject. In embodiments, methods of treating PDD-NOS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of PDD-NOS for more than 8, 10, 12, 14, 16, 18, 20, 22 or 24 hours after administration to the subject. In embodiments, the pharmaceutical compositions provide improvement of next day functioning of the subject with PDD-NOS. For example, the pharmaceutical compositions may provide improvement in one or more symptoms of PDD-NOS for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having PDD-NOS in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having PDD-NOS in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having PDD-NOS simultaneously or at spaced apart intervals.

In embodiments, methods include treating Asperger's syndrome by administering to a subject in need thereof about 0.001 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of Asperger's syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Asperger's syndrome may include (S)-3-amino-4-(difluoromethylenyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Asperger's syndrome once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Asperger's syndrome can be about 0.5 to 50 mg per day or 1 mg to 10 mg per day and can be increased to 75 mg per day. Dosages can be lower for infants and children than for adults. In embodiments, an infant or pediatric dose for treating Asperger's syndrome can be from about 0.01 to 10 mg per day once or in 2, 3 or 4 divided doses. In embodiments, a pediatric dose for treating Asperger's syndrome can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with Asperger's syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Asperger's syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Asperger's syndrome for more than 1 hour after administration to the subject. In embodiments, methods of treating Asperger's syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Asperger's syndrome for more than 2 hours after administration to the subject. In embodiments, methods of treating Asperger's syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Asperger's syndrome for more than 3 hours after administration to the subject. In embodiments, methods of treating Asperger's syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Asperger's syndrome for more than 4 hours after administration to the subject. In embodiments, methods of treating Asperger's syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Asperger's syndrome for more than 6 hours after administration to the subject. In embodiments, methods of treating Asperger's syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Asperger's syndrome for more than 8, 10, 12, 14, 16, 18, 20, 22 or 24 hours after administration to the subject. In embodiments, the pharmaceutical compositions provide improvement of next day functioning of the subject with Asperger's syndrome. For example, the pharmaceutical compositions may provide improvement in one or more symptoms of Asperger's syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having Asperger's syndrome in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Asperger's syndrome in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Asperger's syndrome simultaneously or at spaced apart intervals.

In embodiments, methods include treating Angelman syndrome by administering to a subject in need thereof about 0.001 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of Angelman syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.01 to 0.1 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Angelman syndrome may include (S)-3-amino-4-(difluoromethylenyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Angelman syndrome once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Angelman syndrome can be about 0.5 to 50 mg per day or 1 mg to 10 mg per day and can be increased to 75 mg per day. Dosages can be lower for infants and children than for adults. In embodiments, an infant or pediatric dose for treating Angelman syndrome can be from about 0.01 to 10 mg per day once or in 2, 3 or 4 divided doses. In embodiments, a pediatric dose for treating Angelman syndrome can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with Angelman syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Angelman syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Angelman syndrome for more than 1 hour after administration to the subject. In embodiments, methods of treating Angelman syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Angelman syndrome for more than 2 hours after administration to the subject. In embodiments, methods of treating Angelman syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Angelman syndrome for more than 3 hours after administration to the subject. In embodiments, methods of treating Angelman syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Angelman syndrome for more than 4 hours after administration to the subject. In embodiments, methods of treating Angelman syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Angelman syndrome for more than 6 hours after administration to the subject. In embodiments, methods of treating Angelman syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Angelman syndrome for more than 8, 10, 12, 14, 16, 18, 20, 22 or 24 hours after administration to the subject. In embodiments, the pharmaceutical compositions provide improvement of next day functioning of the subject with Angelman syndrome. For example, the pharmaceutical compositions may provide improvement in one or more symptoms of Angelman syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having Angelman syndrome in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Angelman syndrome in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Angelman syndrome simultaneously or at spaced apart intervals.

In embodiments, methods include treating Fragile X syndrome by administering to a subject in need thereof about 0.005 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of Fragile X syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Fragile X syndrome may include (S)-3-amino-4-(difluoromethylenyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Fragile X syndrome once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Autism Spectrum Disorder can be about 0.5 to 50 mg per day or 1 mg to 10 mg per day and can be increased to 75 mg per day. Dosages can be lower for infants and children than for adults. In embodiments, an infant or pediatric dose for treating Fragile X syndrome can be from about 0.01 to 10 mg per day once or in 2, 3 or 4 divided doses. In embodiments, a pediatric dose for treating Fragile X syndrome can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with Fragile X syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Fragile X syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Fragile X syndrome for more than 1 hour after administration to the subject. In embodiments, methods of treating Fragile X syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Fragile X syndrome for more than 2 hours after administration to the subject. In embodiments, methods of treating Fragile X syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Fragile X syndrome for more than 3 hours after administration to the subject. In embodiments, methods of treating Fragile X syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Fragile X syndrome for more than 4 hours after administration to the subject. In embodiments, methods of treating Fragile X syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Fragile X syndrome for more than 6 hours after administration to the subject. In embodiments, methods of treating Fragile X syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Fragile X syndrome for more than 8, 10, 12, 14, 16, 18, 20, 22 or 24 hours after administration to the subject. In embodiments, the pharmaceutical compositions provide improvement of next day functioning of the subject with Fragile X syndrome. For example, the pharmaceutical compositions may provide improvement in one or more symptoms of Fragile X syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having Fragile X syndrome in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Fragile X syndrome in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Fragile X syndrome simultaneously or at spaced apart intervals.

In embodiments, methods include treating Fragile X-associated tremor/ataxia syndrome (FXTAS) by administering to a subject in need thereof about 0.001 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of FXTAS. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating FXTAS may include (S)-3-amino-4-(difluoromethylenyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 11 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with FXTAS once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating FXTAS can be about 0.5 to 50 mg per day or 1 mg to 10 mg per day and can be increased to 75 mg per day. Dosages can be lower for infants and children than for adults. In embodiments, an infant or pediatric dose for treating FXTAS can be from about 0.01 to 10 mg per day once or in 2, 3 or 4 divided doses. In embodiments, a pediatric dose for treating FXTAS can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with FXTAS via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating FXTAS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of FXTAS for more than 1 hour after administration to the subject. In embodiments, methods of treating FXTAS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of FXTAS for more than 2 hours after administration to the subject. In embodiments, methods of treating FXTAS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of FXTAS for more than 3 hours after administration to the subject. In embodiments, methods of treating FXTAS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of FXTAS for more than 4 hours after administration to the subject. In embodiments, methods of treating FXTAS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of FXTAS for more than 6 hours after administration to the subject. In embodiments, methods of treating FXTAS are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of FXTAS for more than 8, 10, 12, 14, 16, 18, 20, 22 or 24 hours after administration to the subject. In embodiments, the pharmaceutical compositions provide improvement of next day functioning of the subject with FXTAS. For example, the pharmaceutical compositions may provide improvement in one or more symptoms of FXTAS for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having FXTAS in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having FXTAS in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having FXTAS simultaneously or at spaced apart intervals.

In embodiments, methods include treating Childhood Disintegrative Disorder (CDD) by administering to a subject in need thereof about 0.005 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of CDD. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating CDD may include (S)-3-amino-4-(difluoromethyl-enyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 11 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with CDD once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating CDD can be about 0.5 to 50 mg per day or 1 mg to 10 mg per day and can be increased to 75 mg per day. Dosages can be lower for infants and children than for adults. In embodiments, an infant or pediatric dose for treating CDD can be from about 0.01 to 10 mg per day once or in 2, 3 or 4 divided doses. In embodiments, a pediatric dose for treating CDD can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with CDD via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating CDD are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of CDD for more than 1 hour after administration to the subject. In embodiments, methods of treating CDD are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of CDD for more than 2 hours after administration to the subject. In embodiments, methods of treating CDD are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of CDD for more than 3 hours after administration to the subject. In embodiments, methods of treating CDD are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of CDD for more than 4 hours after administration to the subject. In embodiments, methods of treating CDD are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of CDD for more than 6 hours after administration to the subject. In embodiments, methods of treating CDD are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of CDD for more than 8, 10, 12, 14, 16, 18, 20, 22 or 24 hours after administration to the subject. In embodiments, the pharmaceutical compositions provide improvement of next day functioning of the subject with CDD. For example, the pharmaceutical compositions may provide improvement in one or more symptoms of CDD for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having CDD in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having CDD in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having CDD simultaneously or at spaced apart intervals.

In embodiments, methods include treating Williams Syndrome by administering to a subject in need thereof about 0.005 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of Williams Syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Williams Syndrome may include (S)-3-amino-4-(difluoromethylenyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Williams Syndrome once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Williams Syndrome can be about 0.5 to 50 mg per day or 1 mg to 10 mg per day and can be increased to 75 mg per day. Dosages can be lower for infants and children than for adults. In embodiments, an infant or pediatric dose for treating Williams Syndrome can be from about 0.01 to 10 mg per day once or in 2, 3 or 4 divided doses. In embodiments, a pediatric dose for treating Williams Syndrome can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with Williams Syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Williams Syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Williams Syndrome for more than 1 hour after administration to the subject. In embodiments, methods of treating Williams syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Williams Syndrome for more than 2 hours after administration to the subject. In embodiments, methods of treating Williams syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Williams Syndrome for more than 3 hours after administration to the subject. In embodiments, methods of treating Williams Syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Williams Syndrome for more than 4 hours after administration to the subject. In embodiments, methods of treating Williams Syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Williams Syndrome for more than 6 hours after administration to the subject. In embodiments, methods of treating Williams Syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Williams Syndrome for more than 8, 10, 12, 14, 16, 18, 20, 22 or 24 hours after administration to the subject. In embodiments, the pharmaceutical compositions provide improvement of next day functioning of the subject with Williams Syndrome. For example, the pharmaceutical compositions may provide improvement in one or more symptoms of Williams Syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having Williams Syndrome in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Williams Syndrome in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Williams Syndrome simultaneously or at spaced apart intervals.

In embodiments, methods include treating Jacobsen syndrome by administering to a subject in need thereof about 0.005 mg to about 750 mg of (S)-3-amino-4-(difluoromethylenyl)cyclopent-1-ene-1-carboxylic acid or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of Jacobsen syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Jacobsen syndrome may include (S)-3-amino-4-(difluoromethylenyl)cyclopent-1-ene-1-carboxylic acid or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 11 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Jacobsen syndrome once, twice, three or four times daily, every other day, once weekly, or once a month. In embodiments, (S)-3-amino-4-(difluoromethylenyl) cyclopent-1-ene-1-carboxylic acid or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, (S)-3-amino-4-(difluoromethylenyl)cyclopent-1-ene-1-carboxylic acid or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Jacobsen syndrome can be about 0.5 to 50 mg per day or 1 mg to 10 mg per day and can be increased to 75 mg per day. Dosages can be lower for infants and children than for adults. In embodiments, an infant or pediatric dose for treating Jacobsen syndrome can be from about 0.01 to 10 mg per day once or in 2, 3 or 4 divided doses. In embodiments, a pediatric dose for treating Jacobsen syndrome can be 0.075 mg/kg/day to 1.0 mg/kg/day. In embodiments, the subject may be started at a low dose and the dosage is escalated over time.

In embodiments, (S)-3-amino-4-(difluoromethylenyl)cyclopent-1-ene-1-carboxylic acid or a pharmaceutically acceptable salt thereof is administered to a subject with Jacobsen syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Jacobsen syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Jacobsen syndrome for more than 1 hour after administration to the subject. In embodiments, methods of treating Jacobsen syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Jacobsen syndrome for more than 2 hours after administration to the subject. In embodiments, methods of treating Jacobsen syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Jacobsen syndrome for more than 3 hours after administration to the subject. In embodiments, methods of treating Jacobsen syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Jacobsen syndrome for more than 4 hours after administration to the subject. In embodiments, methods of treating Jacobsen syndrome are provided which include administering to a subject in need thereof a pharmaceutical composition including (S)-3-amino-4-(difluoromethylenyl) cyclopent-1-ene-1-carboxylic acid or a pharmaceutically acceptable salt thereof wherein the composition provides improvement in one or more symptoms of Jacobsen syndrome for more than 6 hours after administration to the subject. In embodiments, methods of treating Jacobsen syndrome are provided which include administering to a subject in need thereof a pharmaceutical composition including (S)-3-amino-4-(difluoromethylenyl)cyclopent-1-ene-1-carboxylic acid or a pharmaceutically acceptable salt thereof wherein the composition provides improvement in one or more symptoms of Jacobsen syndrome for more than 8, 10, 12, 14, 16, 18, 20, 22 or 24 hours after administration to the subject. In embodiments, the pharmaceutical compositions provide improvement of next day functioning of the subject with Jacobsen syndrome. For example, the pharmaceutical compositions may provide improvement in one or more symptoms of Jacobsen syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (S)-3-amino-4-(difluoromethylenyl)cyclopent-1-ene-1-carboxylic acid or a pharmaceutically acceptable salt thereof is administered to a subject having Jacobsen syndrome in combination with one or more of (1S,3S)-3-amino-4-difluoromethylenyl-1-cyclopentanoic acid or a pharmaceutically acceptable salt thereof, or vigabatrin or a pharmaceutically acceptable salt thereof. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Jacobsen syndrome in separate dosage forms or combined in one dosage form. In embodiments, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Jacobsen syndrome simultaneously or at spaced apart intervals.

In embodiments, methods include treating Autism Spectrum Disorder by administering to a subject in need thereof about 0.001 mg to about 750 mg of a compound according to Formula I or a pharmaceutically acceptable salt thereof, e.g., hydrochloride salt. In embodiments, the amount of a compound according to Formula I or a pharmaceutically acceptable salt thereof, e.g., hydrochloride salt, can be between 0.001 and 1000 mg/day, or 0.001 mg/kg/day to 14 mg/kg/day, for treatment of Autism Spectrum Disorder. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Autism Spectrum Disorder may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Autism Spectrum Disorder once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Autism Spectrum Disorder can be about 0.5 to 50 mg per day or 1 mg to 10 mg per day and can be increased to 75 mg per day. Dosages can be lower for infants and children than for adults. In embodiments, an infant or pediatric dose for treating Autism Spectrum Disorder can be from about 0.01 to 10 mg per day once or in 2, 3 or 4 divided doses. In embodiments, a pediatric dose for treating Autism Spectrum Disorder can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with Autism Spectrum Disorder via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Autism Spectrum Disorder are provided which include administering to a subject in need thereof a pharmaceutical composition including a compound according to Formula I or a pharmaceutically acceptable salt thereof wherein the composition provides improvement in one or more symptoms of Autism Spectrum Disorder for more than 1 hour after administration to the subject. In embodiments, methods of treating Autism Spectrum Disorder are provided which include administering to a subject in need thereof a pharmaceutical composition including a compound according to Formula I or a pharmaceutically acceptable salt thereof wherein the composition provides improvement in one or more symptoms of Autism Spectrum Disorder for more than 2 hours after administration to the subject. In embodiments, methods of treating Autism Spectrum Disorder are provided which include administering to a subject in need thereof a pharmaceutical composition including a compound according to Formula I or a pharmaceutically acceptable salt thereof wherein the composition provides improvement in one or more symptoms of Autism Spectrum Disorder for more than 3 hours after administration to the subject. In embodiments, methods of treating Autism Spectrum Disorder are provided which include administering to a subject in need thereof a pharmaceutical composition including a compound according to Formula I or a pharmaceutically acceptable salt thereof wherein the composition provides improvement in one or more symptoms of Autism Spectrum Disorder for more than 4 hours after administration to the subject. In embodiments, methods of treating Autism Spectrum Disorder are provided which include administering to a subject in need thereof a pharmaceutical composition including a compound according to Formula I or a pharmaceutically acceptable salt thereof wherein the composition provides improvement in one or more symptoms of Autism Spectrum Disorder for more than 6 hours after administration to the subject. In embodiments, methods of treating Autism Spectrum Disorder are provided which include administering to a subject in need thereof a pharmaceutical composition including a compound according to Formula I or a pharmaceutically acceptable salt thereof wherein the composition provides improvement in one or more symptoms of Autism Spectrum Disorder for more than 8, 10, 12, 14, 16, 18, 20, 22 or 24 hours after administration to the subject. In embodiments, the pharmaceutical compositions provide improvement of next day functioning of the subject with Autism Spectrum Disorder. For example, the pharmaceutical compositions may provide improvement in one or more symptoms of Autism Spectrum Disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt thereof is administered to a subject having Autism Spectrum Disorder in combination with one or more of (S)-3-amino-4-(difluoromethylenyl) cyclopent-1-ene-1-carboxylic acid, (1S,3S)-3-amino-4-difluoromethylenyl-1-cyclopentanoic acid or a pharmaceutically acceptable salt thereof, or vigabatrin or a pharmaceutically acceptable salt thereof. In embodiments, a compound according to Formula I or a pharmaceutically acceptable salt thereof, (S)-3-amino-4-(difluoromethylenyl) cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Autism Spectrum Disorder in separate dosage forms or combined in one dosage form. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Autism Spectrum Disorder simultaneously or at spaced apart intervals.

In embodiments, methods include treating pervasive developmental disorder not otherwise specified (PDD-NOS) by administering to a subject in need thereof about 0.001 mg to about 750 mg of a compound according to Formula I or a pharmaceutically acceptable salt thereof, e.g., hydrochloride salt. In embodiments, the amount of a compound according to Formula I or a pharmaceutically acceptable salt thereof, e.g., hydrochloride salt, can be between 0.001 and 1000 mg/day, or 0.001 mg/kg/day to 14 mg/kg/day, for treatment of PDD-NOS. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating PDD-NOS may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with PDD-NOS once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating PDD-NOS can be about 0.5 to 50 mg per day or 1 mg to 10 mg per day and can be increased to 75 mg per day. Dosages can be lower for infants and children than for adults. In embodiments, an infant or pediatric dose for treating PDD-NOS can be from about 0.01 to 10 mg per day once or in 2, 3 or 4 divided doses. In embodiments, a pediatric dose for treating PDD-NOS can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with PDD-NOS via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating PDD-NOS are provided which include administering to a subject in need thereof a pharmaceutical composition including a compound according to Formula I or a pharmaceutically acceptable salt thereof wherein the composition provides improvement in one or more symptoms of PDD-NOS for more than 1 hour after administration to the subject. In embodiments, methods of treating PDD-NOS are provided which include administering to a subject in need thereof a pharmaceutical composition including a compound according to Formula I or a pharmaceutically acceptable salt thereof wherein the composition provides improvement in one or more symptoms of PDD-NOS for more than 2 hours after administration to the subject. In embodiments, methods of treating PDD-NOS are provided which include administering to a subject in need thereof a pharmaceutical composition including a compound according to Formula I or a pharmaceutically acceptable salt thereof wherein the composition provides improvement in one or more symptoms of PDD-NOS for more than 3 hours after administration to the subject. In embodiments, methods of treating PDD-NOS are provided which include administering to a subject in need thereof a pharmaceutical composition including a compound according to Formula I or a pharmaceutically acceptable salt thereof wherein the composition provides improvement in one or more symptoms of PDD-NOS for more than 4 hours after administration to the subject. In embodiments, methods of treating PDD-NOS are provided which include administering to a subject in need thereof a pharmaceutical composition including a compound according to Formula I or a pharmaceutically acceptable salt thereof wherein the composition provides improvement in one or more symptoms of PDD-NOS for more than 6 hours after administration to the subject. In embodiments, methods of treating PDD-NOS are provided which include administering to a subject in need thereof a pharmaceutical composition a compound according to Formula I or a pharmaceutically acceptable salt thereof wherein the composition provides improvement in one or more symptoms of PDD-NOS for more than 8, 10, 12, 14, 16, 18, 20, 22 or 24 hours after administration to the subject. In embodiments, the pharmaceutical compositions provide improvement of next day functioning of the subject with PDD-NOS. For example, the pharmaceutical compositions may provide improvement in one or more symptoms of PDD-NOS for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt thereof is administered to a subject having PDD-NOS in combination with one or more of (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having PDD-NOS in separate dosage forms or combined in one dosage form. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having PDD-NOS simultaneously or at spaced apart intervals.

In embodiments, methods include treating Asperger's syndrome by administering to a subject in need thereof about 0.001 mg to about 750 mg of a compound according to Formula I or a pharmaceutically acceptable salt thereof, e.g., hydrochloride salt. In embodiments, the amount of a compound according to Formula I or a pharmaceutically acceptable salt thereof, e.g., hydrochloride salt, can be between 0.001 and 1000 mg/day, or 0.001 mg/kg/day to 14 mg/kg/day, for treatment of Asperger's syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Asperger's syndrome may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Asperger's syndrome once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Asperger's syndrome can be about 0.5 to 50 mg per day or 1 mg to 10 mg per day and can be increased to 75 mg per day. Dosages can be lower for infants and children than for adults. In embodiments, an infant or pediatric dose for treating Asperger's syndrome can be from about 0.01 to 10 mg per day once or in 2, 3 or 4 divided doses. In embodiments, a pediatric dose for treating Asperger's syndrome can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with Asperger's syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Asperger's syndrome are provided which include administering to a subject in need thereof a pharmaceutical composition including a compound according to Formula I or a pharmaceutically acceptable salt thereof wherein the composition provides improvement in one or more symptoms of Asperger's syndrome for more than 1 hour after administration to the subject. In embodiments, methods of treating Asperger's syndrome are provided which include administering to a subject in need thereof a pharmaceutical composition including a compound according to Formula I or a pharmaceutically acceptable salt thereof wherein the composition provides improvement in one or more symptoms of Asperger's syndrome for more than 2 hours after administration to the subject. In embodiments, methods of treating Asperger's syndrome are provided which include administering to a subject in need thereof a pharmaceutical composition including a compound according to Formula I or a pharmaceutically acceptable salt thereof wherein the composition provides improvement in one or more symptoms of Asperger's syndrome for more than 3 hours after administration to the subject. In embodiments, methods of treating Asperger's syndrome are provided which include administering to a subject in need thereof a pharmaceutical composition including a compound according to Formula I or a pharmaceutically acceptable salt thereof wherein the composition provides improvement in one or more symptoms of Asperger's syndrome for more than 4 hours after administration to the subject. In embodiments, methods of treating Asperger's syndrome are provided which include administering to a subject in need thereof a pharmaceutical composition including a compound according to Formula I or a pharmaceutically acceptable salt thereof wherein the composition provides improvement in one or more symptoms of Asperger's syndrome for more than 6 hours after administration to the subject. In embodiments, methods of treating Asperger's syndrome are provided which include administering to a subject in need thereof a pharmaceutical composition including a compound according to Formula I or a pharmaceutically acceptable salt thereof wherein the composition provides improvement in one or more symptoms of Asperger's syndrome for more than 8, 10, 12, 14, 16, 18, 20, 22 or 24 hours after administration to the subject. In embodiments, the pharmaceutical compositions provide improvement of next day functioning of the subject with Asperger's syndrome. For example, the pharmaceutical compositions may provide improvement in one or more symptoms of Asperger's syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt thereof is administered to a subject having Asperger's syndrome in combination with one or more of (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof. In embodiments, a compound according to Formula I a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Asperger's syndrome in separate dosage forms or combined in one dosage form. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Asperger's syndrome simultaneously or at spaced apart intervals.

In embodiments, methods include treating Angelman syndrome by administering to a subject in need thereof about 0.001 mg to about 750 mg of a compound according to Formula I or a pharmaceutically acceptable salt thereof, e.g., hydrochloride salt. In embodiments, the amount of a compound according to Formula I or a pharmaceutically acceptable salt thereof, e.g., hydrochloride salt, can be between 0.001 and 1000 mg/day, or 0.001 mg/kg/day to 14 mg/kg/day, for treatment of Angelman syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.3 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Angelman syndrome may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Angelman syndrome once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Angelman syndrome can be about 0.5 to 50 mg per day or 1 mg to 10 mg per day and can be increased to 75 mg per day. Dosages can be lower for infants and children than for adults. In embodiments, an infant or pediatric dose for treating Angelman syndrome can be from about 0.01 to 10 mg per day once or in 2, 3 or 4 divided doses. In embodiments, a pediatric dose for treating Angelman syndrome can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with Angelman syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Angelman syndrome are provided which include administering to a subject in need thereof a pharmaceutical composition including a compound according to Formula I or a pharmaceutically acceptable salt thereof wherein the composition provides improvement in one or more symptoms of Angelman syndrome for more than 1 hour after administration to the subject. In embodiments, methods of treating Angelman syndrome are provided which include administering to a subject in need thereof a pharmaceutical composition including a compound according to Formula I or a pharmaceutically acceptable salt thereof wherein the composition provides improvement in one or more symptoms of Angelman syndrome for more than 2 hours after administration to the subject. In embodiments, methods of treating Angelman syndrome are provided which include administering to a subject in need thereof a pharmaceutical composition including a compound according to Formula I or a pharmaceutically acceptable salt thereof wherein the composition provides improvement in one or more symptoms of Angelman syndrome for more than 3 hours after administration to the subject. In embodiments, methods of treating Angelman syndrome are provided which include administering to a subject in need thereof a pharmaceutical composition including a compound according to Formula I or a pharmaceutically acceptable salt thereof wherein the composition provides improvement in one or more symptoms of Angelman syndrome for more than 4 hours after administration to the subject. In embodiments, methods of treating Angelman syndrome are provided which include administering to a subject in need thereof a pharmaceutical composition including (a compound according to Formula I or a pharmaceutically acceptable salt thereof wherein the composition provides improvement in one or more symptoms of Angelman syndrome for more than 6 hours after administration to the subject. In embodiments, methods of treating Angelman syndrome are provided which include administering to a subject in need thereof a pharmaceutical composition including a compound according to Formula I or a pharmaceutically acceptable salt thereof wherein the composition provides improvement in one or more symptoms of Angelman syndrome for more than 8, 10, 12, 14, 16, 18, 20, 22 or 24 hours after administration to the subject. In embodiments, the pharmaceutical compositions provide improvement of next day functioning of the subject with Angelman syndrome. For example, the pharmaceutical compositions may provide improvement in one or more symptoms of Angelman syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt thereof is administered to a subject having Angelman syndrome in combination with one or more of (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof. In embodiments, Formula I or a pharmaceutically acceptable salt thereof, (S)-3-amino-4-(difluoromethylenyl) cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Angelman syndrome in separate dosage forms or combined in one dosage form. In embodiments, Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Angelman syndrome simultaneously or at spaced apart intervals.

In embodiments, methods include treating Fragile X syndrome by administering to a subject in need thereof about 0.005 mg to about 750 mg of a compound according to Formula I or a pharmaceutically acceptable salt thereof, e.g., hydrochloride salt. In embodiments, the amount of a compound according to Formula I or a pharmaceutically acceptable salt thereof, e.g., hydrochloride salt, can be between 0.001 and 1000 mg/day, or 0.001 mg/kg/day to 14 mg/kg/day, for treatment of Fragile X syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Fragile X syndrome may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Fragile X syndrome once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Autism Spectrum Disorder can be about 0.5 to 50 mg per day or 1 mg to 10 mg per day and can be increased to 75 mg per day. Dosages can be lower for infants and children than for adults. In embodiments, an infant or pediatric dose for treating Fragile X syndrome can be from about 0.01 to 10 mg per day once or in 2, 3 or 4 divided doses. In embodiments, a pediatric dose for treating Fragile X syndrome can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with Fragile X syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Fragile X syndrome are provided which include administering to a subject in need thereof a pharmaceutical composition including a compound according to Formula I or a pharmaceutically acceptable salt thereof wherein the composition provides improvement in one or more symptoms of Fragile X syndrome for more than 1 hour after administration to the subject. In embodiments, methods of treating Fragile X syndrome are provided which include administering to a subject in need thereof a pharmaceutical composition including a compound according to Formula I or a pharmaceutically acceptable salt thereof wherein the composition provides improvement in one or more symptoms of Fragile X syndrome for more than 2 hours after administration to the subject. In embodiments, methods of treating Fragile X syndrome are provided which include administering to a subject in need thereof a pharmaceutical composition including a compound according to Formula I or a pharmaceutically acceptable salt thereof wherein the composition provides improvement in one or more symptoms of Fragile X syndrome for more than 3 hours after administration to the subject. In embodiments, methods of treating Fragile X syndrome are provided which include administering to a subject in need thereof a pharmaceutical composition including a compound according to Formula I or a pharmaceutically acceptable salt thereof wherein the composition provides improvement in one or more symptoms of Fragile X syndrome for more than 4 hours after administration to the subject. In embodiments, methods of treating Fragile X syndrome are provided which include administering to a subject in need thereof a pharmaceutical composition including a compound according to Formula I or a pharmaceutically acceptable salt thereof wherein the composition provides improvement in one or more symptoms of Fragile X syndrome for more than 6 hours after administration to the subject. In embodiments, methods of treating Fragile X syndrome are provided which include administering to a subject in need thereof a pharmaceutical composition including a compound according to Formula I or a pharmaceutically acceptable salt thereof wherein the composition provides improvement in one or more symptoms of Fragile X syndrome for more than 8, 10, 12, 14, 16, 18, 20, 22 or 24 hours after administration to the subject. In embodiments, the pharmaceutical compositions provide improvement of next day functioning of the subject with Fragile X syndrome. For example, the pharmaceutical compositions may provide improvement in one or more symptoms of Fragile X syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt thereof is administered to a subject having Fragile X syndrome in combination with one or more of (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Fragile X syndrome in separate dosage forms or combined in one dosage form. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Fragile X syndrome simultaneously or at spaced apart intervals.

In embodiments, methods include treating Fragile X-associated tremor/ataxia syndrome (FXTAS) by administering to a subject in need thereof about 0.001 mg to about 750 mg of a compound according to Formula I or a pharmaceutically acceptable salt thereof, e.g., hydrochloride salt. In embodiments, the amount of a compound according to Formula I or a pharmaceutically acceptable salt thereof, e.g., hydrochloride salt, can be between 0.001 and 1000 mg/day, or 0.001 mg/kg/day to 14 mg/kg/day, for treatment of FXTAS. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating FXTAS may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with FXTAS once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating FXTAS can be about 0.5 to 50 mg per day or 1 mg to 10 mg per day and can be increased to 75 mg per day. Dosages can be lower for infants and children than for adults. In embodiments, an infant or pediatric dose for treating FXTAS can be from about 0.01 to 10 mg per day once or in 2, 3 or 4 divided doses. In embodiments, a pediatric dose for treating FXTAS can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with FXTAS via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating FXTAS are provided which include administering to a subject in need thereof a pharmaceutical composition including a compound according to Formula I or a pharmaceutically acceptable salt thereof wherein the composition provides improvement in one or more symptoms of FXTAS for more than 1 hour after administration to the subject. In embodiments, methods of treating FXTAS are provided which include administering to a subject in need thereof a pharmaceutical composition including a compound according to Formula I or a pharmaceutically acceptable salt thereof wherein the composition provides improvement in one or more symptoms of FXTAS for more than 2 hours after administration to the subject. In embodiments, methods of treating FXTAS are provided which include administering to a subject in need thereof a pharmaceutical composition including a compound according to Formula I or a pharmaceutically acceptable salt thereof wherein the composition provides improvement in one or more symptoms of FXTAS for more than 3 hours after administration to the subject. In embodiments, methods of treating FXTAS are provided which include administering to a subject in need thereof a pharmaceutical composition including a compound according to Formula I or a pharmaceutically acceptable salt thereof wherein the composition provides improvement in one or more symptoms of FXTAS for more than 4 hours after administration to the subject. In embodiments, methods of treating FXTAS are provided which include administering to a subject in need thereof a pharmaceutical composition including a compound according to Formula I or a pharmaceutically acceptable salt thereof wherein the composition provides improvement in one or more symptoms of FXTAS for more than 6 hours after administration to the subject. In embodiments, methods of treating FXTAS are provided which include administering to a subject in need thereof a pharmaceutical composition including a compound according to Formula I or a pharmaceutically acceptable salt thereof wherein the composition provides improvement in one or more symptoms of FXTAS for more than 8, 10, 12, 14, 16, 18, 20, 22 or 24 hours after administration to the subject. In embodiments, the pharmaceutical compositions provide improvement of next day functioning of the subject with FXTAS. For example, the pharmaceutical compositions may provide improvement in one or more symptoms of FXTAS for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt is administered to a subject having FXTAS in combination with one or more of thereof (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having FXTAS in separate dosage forms or combined in one dosage form. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having FXTAS simultaneously or at spaced apart intervals.

In embodiments, methods include treating Childhood Disintegrative Disorder (CDD) by administering to a subject in need thereof about 0.005 mg to about 750 mg of a compound according to Formula I or a pharmaceutically acceptable salt thereof, e.g., hydrochloride salt. In embodiments, the amount of a compound according to Formula I or a pharmaceutically acceptable salt thereof, e.g., hydrochloride salt, can be between 0.001 and 1000 mg/day, or 0.001 mg/kg/day to 14 mg/kg/day, for treatment of CDD. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating CDD may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with CDD once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating CDD can be about 0.5 to 50 mg per day or 1 mg to 10 mg per day and can be increased to 75 mg per day. Dosages can be lower for infants and children than for adults. In embodiments, an infant or pediatric dose for treating CDD can be from about 0.01 to 10 mg per day once or in 2, 3 or 4 divided doses. In embodiments, a pediatric dose for treating CDD can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with CDD via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating CDD are provided which include administering to a subject in need thereof a pharmaceutical composition including a compound according to Formula I or a pharmaceutically acceptable salt thereof wherein the composition provides improvement in one or more symptoms of CDD for more than 1 hour after administration to the subject. In embodiments, methods of treating CDD are provided which include administering to a subject in need thereof a pharmaceutical composition including a compound according to Formula I or a pharmaceutically acceptable salt thereof wherein the composition provides improvement in one or more symptoms of CDD for more than 2 hours after administration to the subject. In embodiments, methods of treating CDD are provided which include administering to a subject in need thereof a pharmaceutical composition including a compound according to Formula I or a pharmaceutically acceptable salt thereof wherein the composition provides improvement in one or more symptoms of CDD for more than 3 hours after administration to the subject. In embodiments, methods of treating CDD are provided which include administering to a subject in need thereof a pharmaceutical composition including a compound according to Formula I or a pharmaceutically acceptable salt thereof wherein the composition provides improvement in one or more symptoms of CDD for more than 4 hours after administration to the subject. In embodiments, methods of treating CDD are provided which include administering to a subject in need thereof a pharmaceutical composition including a compound according to Formula I or a pharmaceutically acceptable salt thereof wherein the composition provides improvement in one or more symptoms of CDD for more than 6 hours after administration to the subject. In embodiments, methods of treating CDD are provided which include administering to a subject in need thereof a pharmaceutical composition including a compound according to Formula I or a pharmaceutically acceptable salt thereof wherein the composition provides improvement in one or more symptoms of CDD for more than 8, 10, 12, 14, 16, 18, 20, 22 or 24 hours after administration to the subject. In embodiments, the pharmaceutical compositions provide improvement of next day functioning of the subject with CDD. For example, the pharmaceutical compositions may provide improvement in one or more symptoms of CDD for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt thereof is administered to a subject having CDD in combination with one or more of (S)-3-amino-4-(difluoromethylenyl)cyclopent-1-ene-1-carboxylic acid or a pharmaceutically acceptable salt thereof (1S,3S)-3-amino-4-difluoromethylenyl-1-cyclopentanoic acid or a pharmaceutically acceptable salt thereof, or vigabatrin or a pharmaceutically acceptable salt thereof. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having CDD in separate dosage forms or combined in one dosage form. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having CDD simultaneously or at spaced apart intervals.

In embodiments, methods include treating Williams Syndrome by administering to a subject in need thereof about 0.005 mg to about 750 mg of a compound according to Formula I or a pharmaceutically acceptable salt thereof, e.g., hydrochloride salt. In embodiments, the amount of (S)-3-amino-4-(difluoromethylenyl)cyclopent-1-ene-1-carboxylic acid or a pharmaceutically acceptable salt thereof, e.g., hydrochloride salt, can be between 0.001 and 1000 mg/day, or 0.001 mg/kg/day to 14 mg/kg/day, for treatment of Williams Syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Williams Syndrome may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Williams Syndrome once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Williams Syndrome can be about 0.5 to 50 mg per day or 1 mg to 10 mg per day and can be increased to 75 mg per day. Dosages can be lower for infants and children than for adults. In embodiments, an infant or pediatric dose for treating Williams Syndrome can be from about 0.01 to 10 mg per day once or in 2, 3 or 4 divided doses. In embodiments, a pediatric dose for treating Williams Syndrome can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with Williams Syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Williams Syndrome are provided which include administering to a subject in need thereof a pharmaceutical composition including a compound according to Formula I or a pharmaceutically acceptable salt thereof wherein the composition provides improvement in one or more symptoms of Williams Syndrome for more than 1 hour after administration to the subject. In embodiments, methods of treating Williams syndrome are provided which include administering to a subject in need thereof a pharmaceutical composition including a compound according to Formula I or a pharmaceutically acceptable salt thereof wherein the composition provides improvement in one or more symptoms of Williams Syndrome for more than 2 hours after administration to the subject. In embodiments, methods of treating Williams syndrome are provided which include administering to a subject in need thereof a pharmaceutical composition including a compound according to Formula I or a pharmaceutically acceptable salt thereof wherein the composition provides improvement in one or more symptoms of Williams Syndrome for more than 3 hours after administration to the subject. In embodiments, methods of treating Williams Syndrome are provided which include administering to a subject in need thereof a pharmaceutical composition a compound according to Formula I a pharmaceutically acceptable salt thereof wherein the composition provides improvement in one or more symptoms of Williams Syndrome for more than 4 hours after administration to the subject. In embodiments, methods of treating Williams Syndrome are provided which include administering to a subject in need thereof a pharmaceutical composition including a compound according to Formula I or a pharmaceutically acceptable salt thereof wherein the composition provides improvement in one or more symptoms of Williams Syndrome for more than 6 hours after administration to the subject. In embodiments, methods of treating Williams Syndrome are provided which include administering to a subject in need thereof a pharmaceutical composition including a compound according to Formula I or a pharmaceutically acceptable salt thereof wherein the composition provides improvement in one or more symptoms of Williams Syndrome for more than 8, 10, 12, 14, 16, 18, 20, 22 or 24 hours after administration to the subject. In embodiments, the pharmaceutical compositions provide improvement of next day functioning of the subject with Williams Syndrome. For example, the pharmaceutical compositions may provide improvement in one or more symptoms of Williams Syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt thereof is administered to a subject having Williams Syndrome in combination with one or more of (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Williams Syndrome in separate dosage forms or combined in one dosage form. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Williams Syndrome simultaneously or at spaced apart intervals.

In embodiments, methods include treating Jacobsen syndrome by administering to a subject in need thereof about 0.005 mg to about 750 mg of a compound according to Formula I or a pharmaceutically acceptable salt thereof, e.g., hydrochloride salt. In embodiments, the amount of a compound according to Formula I or a pharmaceutically acceptable salt thereof, e.g., hydrochloride salt, can be between 0.001 and 1000 mg/day, or 0.001 mg/kg/day to 14 mg/kg/day, for treatment of Jacobsen syndrome. For example, the daily dosage can be, e.g., in the range of about 0.001 to 750 mg, 0.001 to 700 mg, 0.001 to 500 mg, 0.001 to 250 mg, 0.001 to 200 mg, 0.001 to 175 mg, 0.001 to 150 mg, 0.001 to 125 mg, 0.001 to 100 mg, 0.001 to 75 mg, 0.001 to 50 mg, 0.001 to 30 mg, 0.001 to 25 mg, 0.001 to 20 mg, 0.001 to 15 mg, 0.001 to 10 mg, 0.001 to 5 mg, 0.001 to 4 mg, 0.001 to 3 mg, 0.001 to 2 mg, 0.001 to 1 mg, 0.001 to 0.75 mg, 0.001 to 0.5 mg, 0.001 to 0.25 mg, 0.001 to 0.1 mg, 0.01 to 750 mg, 0.01 to 700 mg, 0.01 to 500 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 4 mg, 0.01 to 3 mg, 0.01 to 2 mg, 0.01 to 1 mg, 0.01 to 0.75 mg, 0.01 to 0.5 mg, 0.01 to 0.25 mg, 0.01 to 0.1 mg, 0.1 to 750 mg, 0.1 to 700 mg, 0.1 to 500 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 4 mg, 0.1 to 3 mg, 0.1 to 2 mg, 0.1 to 1 mg, 0.1 to 0.75 mg, 0.1 to 0.5 mg, 0.1 to 0.25 mg, 0.25 to 750 mg, 0.25 to 700 mg, 0.25 to 500 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 4 mg, 0.25 to 3 mg, 0.25 to 2 mg, 0.25 to 1 mg, 0.25 to 0.75 mg, 0.25 to 0.5 mg, 0.3 to 750 mg, 0.5 to 700 mg, 0.3 to 500 mg, 0.3 to 250 mg, 0.3 to 200 mg, 0.3 to 175 mg, 0.3 to 150 mg, 0.3 to 125 mg, 0.3 to 100 mg, 0.3 to 75 mg, 0.3 to 50 mg, 0.3 to 30 mg, 0.3 to 25 mg, 0.3 to 20 mg, 0.3 to 15 mg, 0.3 to 10 mg, 0.3 to 5 mg, 0.3 to 4 mg, 0.3 to 3 mg, 0.3 to 2 mg, 0.3 to 1 mg, 0.3 to 0.75 mg, 0.3 to 0.5 mg, 0.4 to 750 mg, 0.4 to 700 mg, 0.4 to 500 mg, 0.4 to 250 mg, 0.4 to 200 mg, 0.4 to 175 mg, 0.4 to 150 mg, 0.4 to 125 mg, 0.4 to 100 mg, 0.4 to 75 mg, 0.4 to 50 mg, 0.4 to 30 mg, 0.4 to 25 mg, 0.4 to 20 mg, 0.4 to 15 mg, 0.4 to 10 mg, 0.4 to 5 mg, 0.4 to 4 mg, 0.4 to 3 mg, 0.4 to 2 mg, 0.4 to 1 mg, 0.4 to 0.75 mg, 0.4 to 0.5 mg, 0.5 to 750 mg, 0.5 to 700 mg, 0.5 to 500 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 4 mg, 0.5 to 3 mg, 0.5 to 2 mg, 0.5 to 1 mg, 0.5 to 0.75 mg, 0.75 to 750 mg, 0.75 to 700 mg, 0.75 to 500 mg, 0.75 to 250 mg, 0.75 to 200 mg, 0.75 to 175 mg, 0.75 to 150 mg, 0.75 to 125 mg, 0.75 to 100 mg, 0.75 to 75 mg, 0.75 to 50 mg, 0.75 to 30 mg, 0.75 to 25 mg, 0.75 to 20 mg, 0.75 to 15 mg, 0.75 to 10 mg, 0.75 to 5 mg, 0.75 to 4 mg, 0.75 to 3 mg, 0.75 to 2 mg, 0.75 to 1 mg, 1 to 750 mg, 1 to 700 mg, 1 to 500 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 750 mg, 2 to 700 mg, 2 to 500 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 2 to 4 mg, 2 to 3 mg, 3 to 750 mg, 3 to 700 mg, 3 to 500 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 3 to 4 mg, 4 to 750 mg, 4 to 700 mg, 4 to 500 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 750 mg, 5 to 700 mg, 5 to 500 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 7.5 to 15 mg, 2.5 to 5 mg, with doses of, e.g., about 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Jacobsen syndrome may include a compound according to Formula I or a pharmaceutically acceptable salt thereof in an amount of, e.g., about 0.001 to 500 mg, 0.001 to 75 mg, 0.01 to 500 mg, 0.01 to 450 mg, 0.01 to 300 mg, 0.01 to 250 mg, 0.01 to 200 mg, 0.01 to 175 mg, 0.01 to 150 mg, 0.01 to 125 mg, 0.01 to 100 mg, 0.01 to 75 mg, 0.01 to 50 mg, 0.01 to 30 mg, 0.01 to 25 mg, 0.01 to 20 mg, 0.01 to 15 mg, 0.01 to 10 mg, 0.01 to 5 mg, 0.01 to 1 mg, 0.025 to 500 mg, 0.025 to 450 mg, 0.025 to 300 mg, 0.025 to 250 mg, 0.025 to 200 mg, 0.025 to 175 mg, 0.025 to 150 mg, 0.025 to 125 mg, 0.025 to 100 mg, 0.025 to 75 mg, 0.025 to 50 mg, 0.025 to 30 mg, 0.025 to 25 mg, 0.025 to 20 mg, 0.025 to 15 mg, 0.025 to 10 mg, 0.025 to 5 mg, 0.025 to 1 mg, 0.05 to 500 mg, 0.05 to 450 mg, 0.05 to 300 mg, 0.05 to 250 mg, 0.05 to 200 mg, 0.05 to 175 mg, 0.05 to 150 mg, 0.05 to 125 mg, 0.05 to 100 mg, 0.05 to 75 mg, 0.05 to 50 mg, 0.05 to 30 mg, 0.05 to 25 mg, 0.05 to 20 mg, 0.05 to 15 mg, 0.05 to 10 mg, 0.05 to 5 mg, 0.05 to 1 mg, 0.075 to 500 mg, 0.075 to 450 mg, 0.075 to 300 mg, 0.075 to 250 mg, 0.075 to 200 mg, 0.075 to 175 mg, 0.075 to 150 mg, 0.075 to 125 mg, 0.075 to 100 mg, 0.075 to 75 mg, 0.075 to 50 mg, 0.075 to 30 mg, 0.075 to 25 mg, 0.075 to 20 mg, 0.075 to 15 mg, 0.075 to 10 mg, 0.075 to 5 mg, 0.075 to 1 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.25 to 500 mg, 0.25 to 450 mg, 0.25 to 300 mg, 0.25 to 250 mg, 0.25 to 200 mg, 0.25 to 175 mg, 0.25 to 150 mg, 0.25 to 125 mg, 0.25 to 100 mg, 0.25 to 75 mg, 0.25 to 50 mg, 0.25 to 30 mg, 0.25 to 25 mg, 0.25 to 20 mg, 0.25 to 15 mg, 0.25 to 10 mg, 0.25 to 5 mg, 0.25 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 1 to 4 mg, 1 to 3 mg, 1 to 2 mg, 2 to 500 mg, 2 to 450 mg, 2 to 300 mg, 2 to 250 mg, 2 to 200 mg, 2 to 175 mg, 2 to 150 mg, 2 to 125 mg, 2 to 100 mg, 2 to 75 mg, 2 to 50 mg, 2 to 30 mg, 2 to 25 mg, 2 to 20 mg, 2 to 15 mg, 2 to 10 mg, 2 to 5 mg, 3 to 500 mg, 3 to 450 mg, 3 to 300 mg, 3 to 250 mg, 3 to 200 mg, 3 to 175 mg, 3 to 150 mg, 3 to 125 mg, 3 to 100 mg, 3 to 75 mg, 3 to 50 mg, 3 to 30 mg, 3 to 25 mg, 3 to 20 mg, 3 to 15 mg, 3 to 10 mg, 3 to 5 mg, 4 to 500 mg, 4 to 450 mg, 4 to 300 mg, 4 to 250 mg, 4 to 200 mg, 4 to 175 mg, 4 to 150 mg, 4 to 125 mg, 4 to 100 mg, 4 to 75 mg, 4 to 50 mg, 4 to 30 mg, 4 to 25 mg, 4 to 20 mg, 4 to 15 mg, 4 to 10 mg, 4 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.001 mg, 0.005 mg, 0.01 mg, 0.025 mg, 0.05 mg, 0.075 mg, 0.1 mg, 0.2 mg, 0.25 mg, 0.3 mg, 0.4 mg, 0.5 mg, 0.6 mg, 0.7 mg, 0.75 mg, 0.8 mg, 0.9 mg, 1 mg, 1.25 mg, 1.5 mg, 1.75 mg, 2.0 mg, 2.25 mg, 2.5 mg, 2.75 mg, 3.0 mg, 3.25 mg, 3.5 mg, 3.75 mg, 4.0 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 8.0 mg, 8.25 mg, 8.5 mg, 8.75 mg, 9.0 mg, 9.25 mg, 9.5 mg, 9.75 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject with Jacobsen syndrome once, twice, three or four times daily, every other day, once weekly, or once a month. In embodiments, a compound according to Formula I or a pharmaceutically acceptable salt thereof is administered to a subject twice a day, (e.g., morning and evening), or three times a day (e.g., at breakfast, lunch, and dinner), at a dose of 0.01-50 mg/administration. In embodiments, a compound according to Formula I or a pharmaceutically acceptable salt thereof is administered to a subject 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 11.75 mg/per day, 11.5 mg/per day, 11.25 mg/per day, 11 mg/per day, 10.75 mg/per day, 10.5 mg/per day, 10.25 mg/per day, 10 mg/per day, 9.75 mg/per day, 9.5 mg/per day, 9.25 mg/per day, 9 mg/per day, 8.75 mg/per day, 8.5 mg/per day, 8.25 mg/per day, 7 mg/per day, 7.75 mg/per day, 7.5 mg/per day, 7.25 mg/per day, 6.0 mg/per day, 5.75 mg/per day, 5.5 mg/per day, 5.25 mg/per day, 5 mg/per day, 4.75 mg/per day, 4.5 mg/per day, 4.25 mg/per day, 4 mg/per day, 3.75 mg/per day, 3.5 mg/per day, 3.25 mg/per day, 3 mg/per day, 2.5 mg/per day, 2 mg/per day, 1.75 mg/per day, 1.5 mg/per day, 1.25 mg/per day, 1 mg/per day, 0.5 mg/per day, 0.25 mg/per day, in one or more doses. In embodiments, an adult dose for treating Jacobsen syndrome can be about 0.5 to 50 mg per day or 1 mg to 10 mg per day and can be increased to 75 mg per day. Dosages can be lower for infants and children than for adults. In embodiments, an infant or pediatric dose for treating Jacobsen syndrome can be from about 0.01 to 10 mg per day once or in 2, 3 or 4 divided doses. In embodiments, a pediatric dose for treating Jacobsen syndrome can be 0.075 mg/kg/day to 1.0 mg/kg/day. In embodiments, the subject may be started at a low dose and the dosage is escalated over time.

In embodiments, a compound according to Formula I or a pharmaceutically acceptable salt thereof is administered to a subject with Jacobsen syndrome via a pharmaceutical composition. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Jacobsen syndrome are provided which include administering to a subject in need thereof a pharmaceutical composition including a compound according to Formula I or a pharmaceutically acceptable salt thereof wherein the composition provides improvement in one or more symptoms of Jacobsen syndrome for more than 1 hour after administration to the subject. In embodiments, methods of treating Jacobsen syndrome are provided which include administering to a subject in need thereof a pharmaceutical composition including a compound according to Formula I or a pharmaceutically acceptable salt thereof wherein the composition provides improvement in one or more symptoms of Jacobsen syndrome for more than 2 hours after administration to the subject. In embodiments, methods of treating Jacobsen syndrome are provided which include administering to a subject in need thereof a pharmaceutical composition including a compound according to Formula I or a pharmaceutically acceptable salt thereof wherein the composition provides improvement in one or more symptoms of Jacobsen syndrome for more than 3 hours after administration to the subject. In embodiments, methods of treating Jacobsen syndrome are provided which include administering to a subject in need thereof a pharmaceutical composition including a compound according to Formula I or a pharmaceutically acceptable salt thereof wherein the composition provides improvement in one or more symptoms of Jacobsen syndrome for more than 4 hours after administration to the subject. In embodiments, methods of treating Jacobsen syndrome are provided which include administering to a subject in need thereof a pharmaceutical composition including a compound according to Formula I or a pharmaceutically acceptable salt thereof wherein the composition provides improvement in one or more symptoms of Jacobsen syndrome for more than 6 hours after administration to the subject. In embodiments, methods of treating Jacobsen syndrome are provided which include administering to a subject in need thereof a pharmaceutical composition including a compound according to Formula I or a pharmaceutically acceptable salt thereof wherein the composition provides improvement in one or more symptoms of Jacobsen syndrome for more than 8, 10, 12, 14, 16, 18, 20, 22 or 24 hours after administration to the subject. In embodiments, the pharmaceutical compositions provide improvement of next day functioning of the subject with Jacobsen syndrome. For example, the pharmaceutical compositions may provide improvement in one or more symptoms of Jacobsen syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, a compound according to Formula I or a pharmaceutically acceptable salt thereof is administered to a subject having Jacobsen syndrome in combination with one or more of (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Jacobsen syndrome in separate dosage forms or combined in one dosage form. In embodiments, a compound according to Formula I or a pharmaceutically acceptable salt thereof, (S)-3-amino-4-(difluoromethylenyl)cyclopent-1-ene-1-carboxylic acid or a pharmaceutically acceptable salt thereof, (1S,3S)-3-amino-4-difluoromethylenyl-1-cyclopentanoic acid or a pharmaceutically acceptable salt thereof, or vigabatrin or a pharmaceutically acceptable salt thereof, may be administered to a subject having Jacobsen syndrome simultaneously or at spaced apart intervals.

In embodiments, methods include treating Autism Spectrum Disorder by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating Autism Spectrum Disorder by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of Autism Spectrum Disorder. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of Autism Spectrum Disorder. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Autism Spectrum Disorder may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating Autism Spectrum Disorder may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having Autism Spectrum Disorder twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having Autism Spectrum Disorder 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating Autism Spectrum Disorder can be about 5 to 80 mg per day and can be increased to 150 mg per day. Dosages can be lower for infants and children than for adults. In embodiments, an infant or pediatric dose for treating Autism Spectrum Disorder can be about 0.1 to 50 mg per day once or in 2, 3 or 4 divided doses. In embodiments, a pediatric dose for treating Autism Spectrum Disorder can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating Autism Spectrum Disorder. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Autism Spectrum Disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Autism Spectrum Disorder for more than 1 hour after administration to the subject. In embodiments, methods of treating Autism Spectrum Disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Autism Spectrum Disorder for more than 2 hours after administration to the subject. In embodiments, methods of treating Autism Spectrum Disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Autism Spectrum Disorder for more than 3 hours after administration to the subject. In embodiments, methods of treating Autism Spectrum Disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Autism Spectrum Disorder for more than 4 hours after administration to the subject. In embodiments, methods of treating Autism Spectrum Disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Autism Spectrum Disorder for more than 6 hours after administration to the subject. In embodiments, methods of treating Autism Spectrum Disorder are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Autism Spectrum Disorder for more than 8, 10, 12, 14, 16, 18, 20, 22 or 24 hours after administration to the subject. In embodiments, the pharmaceutical compositions provide improvement of next day functioning of the subject having Autism Spectrum Disorder. For example, the pharmaceutical compositions may provide improvement in one or more symptoms of Autism Spectrum Disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having Autism Spectrum Disorder in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Autism Spectrum Disorder in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Autism Spectrum Disorder simultaneously or at spaced apart intervals.

In embodiments, methods include treating pervasive developmental disorder not otherwise specified (PDD-NOS) by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating PDD-NOS by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of PDD-NOS. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of PDD-NOS. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating PDD-NOS may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating PDD-NOS may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having PDD-NOS twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having PDD-NOS 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating PDD-NOS can be about 5 to 80 mg per day and can be increased to 150 mg per day. Dosages can be lower for infants and children than for adults. In embodiments, an infant or pediatric dose for treating PDD-NOS can be about 0.1 to 50 mg per day once or in 2, 3 or 4 divided doses. In embodiments, a pediatric dose for treating PDD-NOS can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating PDD-NOS. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating PDD-NOS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of PDD-NOS for more than 1 hour after administration to the subject. In embodiments, methods of treating PDD-NOS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of PDD-NOS for more than 2 hours after administration to the subject. In embodiments, methods of treating PDD-NOS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of PDD-NOS for more than 3 hours after administration to the subject. In embodiments, methods of treating PDD-NOS are provided which include administering to a subject in need thereof a pharmaceutical composition including (1S,3S)-3- amino-4-difluoromethylenyl-1-cyclopentanoic acid or a pharmaceutically acceptable salt thereof wherein the composition provides improvement in one or more symptoms of PDD-NOS for more than 4 hours after administration to the subject. In embodiments, methods of treating PDD-NOS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of PDD-NOS for more than 6 hours after administration to the subject. In embodiments, methods of treating PDD-NOS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of PDD-NOS for more than 8, 10, 12, 14, 16, 18, 20, 22 or 24 hours after administration to the subject. In embodiments, the pharmaceutical compositions provide improvement of next day functioning of the subject having PDD-NOS. For example, the pharmaceutical compositions may provide improvement in one or more symptoms of PDD-NOS for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having PDD-NOS in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having PDD-NOS in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having PDD-NOS simultaneously or at spaced apart intervals.

In embodiments, methods include treating Asperger's syndrome by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating Asperger's syndrome by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of Asperger's syndrome. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of Asperger's syndrome. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Asperger's syndrome may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating Asperger's syndrome may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having Asperger's syndrome twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having Asperger's syndrome 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating Asperger's syndrome can be about 5 to 80 mg per day and can be increased to 150 mg per day. Dosages can be lower for infants and children than for adults. In embodiments, an infant or pediatric dose for treating Asperger's syndrome can be about 0.1 to 50 mg per day once or in 2, 3 or 4 divided doses. In embodiments, a pediatric dose for treating Asperger's syndrome can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating Asperger's syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Asperger's syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Asperger's syndrome for more than 1 hour after administration to the subject. In embodiments, methods of treating Asperger's syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Asperger's syndrome for more than 2 hours after administration to the subject. In embodiments, methods of treating Asperger's syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Asperger's syndrome for more than 3 hours after administration to the subject. In embodiments, methods of treating Asperger's syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Asperger's syndrome for more than 4 hours after administration to the subject. In embodiments, methods of treating Asperger's syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Asperger's syndrome for more than 6 hours after administration to the subject. In embodiments, methods of treating Asperger's syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Asperger's syndrome for more than 8, 10, 12, 14, 16, 18, 20, 22 or 24 hours after administration to the subject. In embodiments, the pharmaceutical compositions provide improvement of next day functioning of the subject having Asperger's syndrome. For example, the pharmaceutical compositions may provide improvement in one or more symptoms of Asperger's syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having Asperger's syndrome in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Asperger's syndrome in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Asperger's syndrome simultaneously or at spaced apart intervals.

In embodiments, methods include treating Angelman syndrome by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating Angelman syndrome by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of Angelman syndrome. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of Angelman syndrome. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Angelman syndrome may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating Angelman syndrome may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having Angelman syndrome twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having Angelman syndrome 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating Angelman syndrome can be about 5 to 80 mg per day and can be increased to 150 mg per day. Dosages can be lower for infants and children than for adults. In embodiments, an infant or pediatric dose for treating Angelman syndrome can be about 0.1 to 50 mg per day once or in 2, 3 or 4 divided doses. In embodiments, a pediatric dose for treating Angelman syndrome can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating Angelman syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Angelman syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Angelman syndrome for more than 1 hour after administration to the subject. In embodiments, methods of treating Angelman syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Angelman syndrome for more than 2 hours after administration to the subject. In embodiments, methods of treating Angelman syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Angelman syndrome for more than 3 hours after administration to the subject. In embodiments, methods of treating Angelman syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Angelman syndrome for more than 4 hours after administration to the subject. In embodiments, methods of treating Angelman syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Angelman syndrome for more than 6 hours after administration to the subject. In embodiments, methods of treating Angelman syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Angelman syndrome for more than 8, 10, 12, 14, 16, 18, 20, 22 or 24 hours after administration to the subject. In embodiments, the pharmaceutical compositions provide improvement of next day functioning of the subject having Angelman syndrome. For example, the pharmaceutical compositions may provide improvement in one or more symptoms of Angelman syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having Angelman syndrome in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Angelman syndrome in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Angelman syndrome simultaneously or at spaced apart intervals.

In embodiments, methods include treating Fragile X syndrome by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating Fragile X syndrome by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of Fragile X syndrome. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of Fragile X syndrome. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Fragile X syndrome may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating Fragile X syndrome may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having Fragile X syndrome twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having Fragile X syndrome 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating Fragile X syndrome can be about 5 to 80 mg per day and can be increased to 150 mg per day. Dosages can be lower for infants and children than for adults. In embodiments, an infant or pediatric dose for treating Fragile X syndrome can be about 0.1 to 50 mg per day once or in 2, 3 or 4 divided doses. In embodiments, a pediatric dose for treating Fragile X syndrome can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating Fragile X syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Fragile X syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Fragile X syndrome for more than 1 hour after administration to the subject. In embodiments, methods of treating Fragile X syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Fragile X syndrome for more than 2 hours after administration to the subject. In embodiments, methods of treating Fragile X syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Fragile X syndrome for more than 3 hours after administration to the subject. In embodiments, methods of treating Fragile X syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Fragile X syndrome for more than 4 hours after administration to the subject. In embodiments, methods of treating Fragile X syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Fragile X syndrome for more than 6 hours after administration to the subject. In embodiments, methods of treating Fragile X syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Fragile X syndrome for more than 8, 10, 12, 14, 16, 18, 20, 22 or 24 hours after administration to the subject. In embodiments, the pharmaceutical compositions provide improvement of next day functioning of the subject having Fragile X syndrome. For example, the pharmaceutical compositions may provide improvement in one or more symptoms of Fragile X syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having Fragile X syndrome in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Fragile X syndrome in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Fragile X syndrome simultaneously or at spaced apart intervals.

In embodiments, methods include treating Fragile X-associated tremor/ataxia syndrome (FXTAS) by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating FXTAS by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of FXTAS. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of FXTAS. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating FXTAS may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating FXTAS may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having FXTAS twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having FXTAS 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating FXTAS can be about 5 to 80 mg per day and can be increased to 150 mg per day. Dosages can be lower for infants and children than for adults. In embodiments, an infant or pediatric dose for treating FXTAS can be about 0.1 to 50 mg per day once or in 2, 3 or 4 divided doses. In embodiments, a pediatric dose for treating FXTAS can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating FXTAS. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating FXTAS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of FXTAS for more than 1 hour after administration to the subject. In embodiments, methods of treating FXTAS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of FXTAS for more than 2 hours after administration to the subject. In embodiments, methods of treating FXTAS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of FXTAS for more than 3 hours after administration to the subject. In embodiments, methods of treating FXTAS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of FXTAS for more than 4 hours after administration to the subject. In embodiments, methods of treating FXTAS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of FXTAS for more than 6 hours after administration to the subject. In embodiments, methods of treating FXTAS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of FXTAS for more than 8, 10, 12, 14, 16, 18, 20, 22 or 24 hours after administration to the subject. In embodiments, the pharmaceutical compositions provide improvement of next day functioning of the subject having FXTAS. For example, the pharmaceutical compositions may provide improvement in one or more symptoms of FXTAS for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having FXTAS in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having FXTAS in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having FXTAS simultaneously or at spaced apart intervals.

In embodiments, methods include treating Childhood Disintegrative Disorder (CDD) by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating CDD by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of CDD. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of CDD. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating CDD may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating CDD may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having CDD twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having CDD 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating CDD can be about 5 to 80 mg per day and can be increased to 150 mg per day. Dosages can be lower for infants and children than for adults. In embodiments, an infant or pediatric dose for treating CDD can be about 0.1 to 50 mg per day once or in 2, 3 or 4 divided doses. In embodiments, a pediatric dose for treating CDD can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating CDD. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating CDD are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of CDD for more than 1 hour after administration to the subject. In embodiments, methods of treating CDD are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of CDD for more than 2 hours after administration to the subject. In embodiments, methods of treating CDD are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of CDD for more than 3 hours after administration to the subject. In embodiments, methods of treating CDD are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of CDD for more than 4 hours after administration to the subject. In embodiments, methods of treating CDD are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of CDD for more than 6 hours after administration to the subject. In embodiments, methods of treating CDD are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of CDD for more than 8, 10, 12, 14, 16, 18, 20, 22 or 24 hours after administration to the subject. In embodiments, the pharmaceutical compositions provide improvement of next day functioning of the subject having CDD. For example, the pharmaceutical compositions may provide improvement in one or more symptoms of CDD for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having CDD in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having CDD in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having CDD simultaneously or at spaced apart intervals.

In embodiments, methods include treating Williams syndrome by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating Williams syndrome by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of Williams syndrome. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of Williams syndrome. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Williams syndrome may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating Williams syndrome may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having Williams syndrome twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having Williams syndrome 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating FXTAS can be about 5 to 80 mg per day and can be increased to 150 mg per day. Dosages can be lower for infants and children than for adults. In embodiments, an infant or pediatric dose for treating Williams syndrome can be about 0.1 to 50 mg per day once or in 2, 3 or 4 divided doses. In embodiments, a pediatric dose for treating Williams syndrome can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating Williams syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Williams syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Williams syndrome for more than 1 hour after administration to the subject. In embodiments, methods of treating Williams syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Williams syndrome for more than 2 hours after administration to the subject. In embodiments, methods of treating Williams syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Williams syndrome for more than 3 hours after administration to the subject. In embodiments, methods of treating Williams syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Williams syndrome for more than 4 hours after administration to the subject. In embodiments, methods of treating FXTAS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Williams syndrome for more than 6 hours after administration to the subject. In embodiments, methods of treating FXTAS are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Williams syndrome for more than 8, 10, 12, 14, 16, 18, 20, 22 or 24 hours after administration to the subject. In embodiments, the pharmaceutical compositions provide improvement of next day functioning of the subject having Williams syndrome. For example, the pharmaceutical compositions may provide improvement in one or more symptoms of Williams syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having Williams syndrome in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Williams syndrome in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Williams syndrome simultaneously or at spaced apart intervals.

In embodiments, methods include treating Jacobsen syndrome by administering to a subject in need thereof about 0.1 mg to about 1500 mg of (1S,3S)-3-amino-4-difluoromethylenyl-1-cyclopentanoic acid or a pharmaceutically acceptable salt thereof, e.g., a hydrochloride salt thereof. In embodiments, methods include treating Jacobsen syndrome by administering to a subject in need thereof about 0.5 mg to about 1000 mg of (1S,3S)-3-amino-4-difluoromethylenyl-1-cyclopentanoic acid or a pharmaceutically acceptable salt thereof, e.g., a hydrochloride salt thereof. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1500 mg/day, or 0.01 mg/kg/day to 15 mg/kg/day, for treatment of Jacobsen syndrome. In embodiments, the amount of (1S,3S)-3-amino-4-difluoromethylenyl-1-cyclopentanoic acid or a pharmaceutically acceptable salt thereof, e.g., a hydrochloride salt thereof, can be between 0.1 and 1000 mg/day for treatment of Jacobsen syndrome. For example, the daily dosage can be, e.g., in the range of about 0.1 to 1500 mg, 0.1 to 1250 mg, 0.1 to 1000 mg, 0.1 to 750 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 1 to 1500 mg, 1 to 1000 mg, 1 to 500 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 1500 mg, 5 to 1000 mg, 5 to 500 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 1500 mg, 10 to 1000 mg, 10 to 500 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 1500 mg, 15 to 1000 mg, 15 to 500 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 1500 mg, 20 to 1000 mg, 20 to 500 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 1500 mg, 25 to 1000 mg, 25 to 500 mg, 25 to 300 mg, 25 to 250 mg, 25 to 200 mg, 25 to 175 mg, 25 to 150 mg, 25 to 125 mg, 25 to 100 mg, 25 to 75 mg, 25 to 50 mg, 25 to 30 mg, 30 to 1500 mg, 30 to 1000 mg, 30 to 500 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 35 to 1500 mg, 35 to 1000 mg, 35 to 500 mg, 35 to 300 mg, 35 to 250 mg, 35 to 200 mg, 35 to 175 mg, 35 to 150 mg, 35 to 125 mg, 35 to 100 mg, 35 to 75 mg, 35 to 50 mg, 40 to 1500 mg, 40 to 1000 mg, 40 to 500 mg, 40 to 300 mg, 40 to 250 mg, 40 to 200 mg, 40 to 175 mg, 40 to 150 mg, 40 to 125 mg, 40 to 100 mg, 40 to 75 mg, 40 to 50 mg, 50 to 1500 mg, 50 to 1000 mg, 50 to 500 mg, 50 to 300 mg, 50 to 250 mg, 50 to 200 mg, 50 to 175 mg, 50 to 150 mg, 50 to 125 mg, 50 to 100 mg, 50 to 75 mg, 75 to 1500 mg, 75 to 1000 mg, 75 to 500 mg, 75 to 300 mg, 75 to 250 mg, 75 to 200 mg, 75 to 175 mg, 75 to 150 mg, 75 to 125 mg, 75 to 100 mg, 100 to 1500 mg, 100 to 1000 mg, 100 to 500 mg, 100 to 300 mg, 100 to 250 mg, 100 to 200 mg, 100 to 175 mg, 100 to 150 mg, 100 to 125 mg, 125 to 1500 mg, 125 to 1000 mg, 125 to 500 mg, 125 to 300 mg, 125 to 250 mg, 125 to 200 mg, 125 to 175 mg, 125 to 150 mg, 150 to 1500 mg, 150 to 1000 mg, 150 to 500 mg, 150 to 300 mg, 150 to 250 mg, 150 to 200 mg, 150 to 175 mg, 175 to 1500 mg, 175 to 1000 mg, 175 to 500 mg, 175 to 300 mg, 175 to 250 mg, 175 to 200 mg, 200 to 1500 mg, 200 to 1000 mg, 200 to 500 mg, 200 to 300 mg, 200 to 250 mg, 250 to 1500 mg, 250 to 1000 mg, 250 to 500 mg, 250 to 300 mg, 7.5 to 15 mg, 2.5 to 5 mg, 1 to 5 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 7.5 mg, 10 mg, 12.5 mg, 15 mg, 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 100 mg, 125 mg, 150 mg, 175 mg, 200 mg, 225 mg, 250 mg, 275 mg, 300 mg, 400 mg and 500 mg being examples.

In embodiments, pharmaceutical compositions for use in treating Jacobsen syndrome may include (1S,3S)-3-amino-4-difluoromethylenyl-1-cyclopentanoic acid or a pharmaceutically acceptable salt thereof in an amount of, e.g., about 0.01 to 500 mg, 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages for treating Jacobsen syndrome may be administered to a subject once, twice, three or four times daily, every other day, once weekly, or once a month. In embodiments, (1S,3S)-3-amino-4-difluoromethylenyl-1-cyclopentanoic acid or a pharmaceutically acceptable salt thereof is administered to a subject having Jacobsen syndrome twice a day, (e.g., morning and evening), or three times a day (e.g., at breakfast, lunch, and dinner), at a dose of 1-50 mg/administration. In embodiments, (1S,3S)-3-amino-4-difluoromethylenyl-1-cyclopentanoic acid or a pharmaceutically acceptable salt thereof is administered to a subject having Jacobsen syndrome 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 2 mg/per day, 1 mg/per day, in one or more doses. In embodiments, an adult dose for treating Jacobsen syndrome can be about 5 to 80 mg per day and can be increased to 150 mg per day. Dosages can be lower for infants and children than for adults. In embodiments, an infant or pediatric dose for treating Jacobsen syndrome can be about 0.1 to 50 mg per day once or in 2, 3 or 4 divided doses. In embodiments, a pediatric dose for treating Jacobsen syndrome can be 0.75 mg/kg/day to 1.5 mg/kg/day. In embodiments, the subject may be started at a low dose and the dosage is escalated over time.

In embodiments, (1S,3S)-3-amino-4-difluoromethylenyl-1-cyclopentanoic acid or a pharmaceutically acceptable salt thereof is administered via a pharmaceutical composition for use in treating Jacobsen syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Jacobsen syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Jacobsen syndrome for more than 1 hour after administration to the subject. In embodiments, methods of treating Jacobsen syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Jacobsen syndrome for more than 2 hours after administration to the subject. In embodiments, methods of treating Jacobsen syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Jacobsen syndrome for more than 3 hours after administration to the subject. In embodiments, methods of treating Jacobsen syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Jacobsen syndrome for more than 4 hours after administration to the subject. In embodiments, methods of treating Jacobsen syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Jacobsen syndrome for more than 6 hours after administration to the subject. In embodiments, methods of treating Jacobsen syndrome are provided which include administering to a subject in need thereof a pharmaceutical composition including (1S,3S)-3-amino-4-difluoromethylenyl-1-cyclopentanoic acid or a pharmaceutically acceptable salt thereof wherein the composition provides improvement in one or more symptoms of Jacobsen syndrome for more than 8, 10, 12, 14, 16, 18, 20, 22 or 24 hours after administration to the subject. In embodiments, the pharmaceutical compositions provide improvement of next day functioning of the subject having Jacobsen syndrome. For example, the pharmaceutical compositions may provide improvement in one or more symptoms of Jacobsen syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, (1S,3S)-3-amino-4-difluoromethylenyl-1-cyclopentanoic acid or a pharmaceutically acceptable salt thereof is administered to a subject having Jacobsen syndrome in combination with one or more of (S)-3-amino-4-(difluoromethylenyl)cyclopent-1-ene-1-carboxylic acid or a pharmaceutically acceptable salt thereof, or vigabatrin or a pharmaceutically acceptable salt thereof. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Jacobsen syndrome in separate dosage forms or combined in one dosage form. In embodiments, (1S,3S)-3-amino-4-difluoromethylenyl-1-cyclopentanoic acid or a pharmaceutically acceptable salt thereof, (S)-3-amino-4-(difluoromethylenyl)cyclopent-1-ene-1-carboxylic acid or a pharmaceutically acceptable salt thereof, or vigabatrin or a pharmaceutically acceptable salt thereof, may be administered to a subject having Jacobsen syndrome simultaneously or at spaced apart intervals.

In embodiments, methods include treating Autism Spectrum Disorder by administering to a subject in need thereof about 1 mg to about 4000 mg of vigabatrin or a pharmaceutically acceptable salt thereof, e.g., a hydrochloride salt thereof. In embodiments, methods include treating Autism Spectrum Disorder by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of Autism Spectrum Disorder. In embodiments, the amount of vigabatrin or a pharmaceutically acceptable salt thereof, e.g., a hydrochloride salt thereof, for treatment of Autism Spectrum Disorder can be between 50 and 3000 mg/day, or 0.7 mg/kg/day to 40 mg/kg/day. For example, the daily dosage for treatment of Autism Spectrum Disorder can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating Autism Spectrum Disorder may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having Autism Spectrum Disorder once, twice, three or four times daily, every other day, once weekly, or once a month. In embodiments, vigabatrin or a pharmaceutically acceptable salt thereof is administered to a subject having Autism Spectrum Disorder twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having Autism Spectrum Disorder 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating Autism Spectrum Disorder can be about 100 to 3000 mg per day and can be increased to 4000 mg per day. Dosages can be lower for infants and children than for adults. In embodiments, an infant or pediatric dose for treating Autism Spectrum Disorder can be about 10 to 500 mg per day once or in 2, 3 or 4 divided doses. In embodiments, a pediatric dose for treating Autism Spectrum Disorder can be 0.7 mg/kg/day to 150 mg/kg/day. In embodiments, the subject may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating Autism Spectrum Disorder. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Autism Spectrum Disorder are provided which include administering to a subject in need thereof a pharmaceutical composition including vigabatrin or a pharmaceutically acceptable salt thereof wherein the composition provides improvement in one or more symptoms of Autism Spectrum Disorder for more than 1 hour after administration to the subject. In embodiments, methods of treating Autism Spectrum Disorder are provided which include administering to a subject in need thereof a pharmaceutical composition including vigabatrin or a pharmaceutically acceptable salt thereof wherein the composition provides improvement in one or more symptoms of Autism Spectrum Disorder for more than 2 hours after administration to the subject. In embodiments, methods of treating Autism Spectrum Disorder are provided which include administering to a subject in need thereof a pharmaceutical composition including vigabatrin or a pharmaceutically acceptable salt thereof wherein the composition provides improvement in one or more symptoms of Autism Spectrum Disorder for more than 3 hours after administration to the subject. In embodiments, methods of treating Autism Spectrum Disorder are provided which include administering to a subject in need thereof a pharmaceutical composition including vigabatrin or a pharmaceutically acceptable salt thereof wherein the composition provides improvement in one or more symptoms of Autism Spectrum Disorder for more than 4 hours after administration to the subject. In embodiments, methods of treating Autism Spectrum Disorder are provided which include administering to a subject in need thereof a pharmaceutical composition including vigabatrin or a pharmaceutically acceptable salt thereof wherein the composition provides improvement in one or more symptoms of Autism Spectrum Disorder for more than 6 hours after administration to the subject. In embodiments, methods of treating Autism Spectrum Disorder are provided which include administering to a subject in need thereof a pharmaceutical composition including vigabatrin or a pharmaceutically acceptable salt thereof wherein the composition provides improvement in one or more symptoms of Autism Spectrum Disorder for more than 8, 10, 12, 14, 16, 18, 20, 22 or 24 hours after administration to the subject. In embodiments, the pharmaceutical compositions for use in treating Autism Spectrum Disorder provide improvement of next day functioning of the subject. For example, the pharmaceutical compositions may provide improvement in one or more symptoms of Autism Spectrum Disorder for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having Autism Spectrum Disorder in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having Autism Spectrum Disorder in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having Autism Spectrum Disorder simultaneously or at spaced apart intervals.

In embodiments, methods include treating pervasive developmental disorder not otherwise specified (PDD-NOS) by administering to a subject in need thereof about 1 mg to about 4000 mg of vigabatrin or a pharmaceutically acceptable salt thereof, e.g., a hydrochloride salt thereof. In embodiments, methods include treating PDD-NOS by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of PDD-NOS. In embodiments, the amount of vigabatrin or a pharmaceutically acceptable salt thereof, e.g., a hydrochloride salt thereof, for treatment of PDD-NOS can be between 50 and 3000 mg/day, or 0.7 mg/kg/day to 40 mg/kg/day. For example, the daily dosage for treatment of PDD-NOS can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating PDD-NOS may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having PDD-NOS once, twice, three or four times daily, every other day, once weekly, or once a month. In embodiments, vigabatrin or a pharmaceutically acceptable salt thereof is administered to a subject having PDD-NOS twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having PDD-NOS 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating PDD-NOS can be about 100 to 3000 mg per day and can be increased to 4000 mg per day. Dosages can be lower for infants and children than for adults. In embodiments, an infant or pediatric dose for treating PDD-NOS can be about 10 to 500 mg per day once or in 2, 3 or 4 divided doses. In embodiments, a pediatric dose for treating PDD-NOS can be 0.7 mg/kg/day to 150 mg/kg/day. In embodiments, the subject having PDD-NOS may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating PDD-NOS. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating PDD-NOS are provided which include administering to a subject in need thereof a pharmaceutical composition including vigabatrin or a pharmaceutically acceptable salt thereof wherein the composition provides improvement in one or more symptoms of PDD-NOS for more than 1 hour after administration to the subject. In embodiments, methods of treating PDD-NOS are provided which include administering to a subject in need thereof a pharmaceutical composition including vigabatrin or a pharmaceutically acceptable salt thereof wherein the composition provides improvement in one or more symptoms of PDD-NOS for more than 2 hours after administration to the subject. In embodiments, methods of treating PDD-NOS are provided which include administering to a subject in need thereof a pharmaceutical composition including vigabatrin or a pharmaceutically acceptable salt thereof wherein the composition provides improvement in one or more symptoms of PDD-NOS for more than 3 hours after administration to the subject. In embodiments, methods of treating PDD-NOS are provided which include administering to a subject in need thereof a pharmaceutical composition including vigabatrin or a pharmaceutically acceptable salt thereof wherein the composition provides improvement in one or more symptoms of PDD-NOS for more than 4 hours after administration to the subject. In embodiments, methods of treating PDD-NOS are provided which include administering to a subject in need thereof a pharmaceutical composition including vigabatrin or a pharmaceutically acceptable salt thereof wherein the composition provides improvement in one or more symptoms of PDD-NOS for more than 6 hours after administration to the subject. In embodiments, methods of treating PDD-NOS are provided which include administering to a subject in need thereof a pharmaceutical composition including vigabatrin or a pharmaceutically acceptable salt thereof wherein the composition provides improvement in one or more symptoms of PDD-NOS for more than 8, 10, 12, 14, 16, 18, 20, 22 or 24 hours after administration to the subject. In embodiments, the pharmaceutical compositions for use in treating PDD-NOS provide improvement of next day functioning of the subject. For example, the pharmaceutical compositions may provide improvement in one or more symptoms of PDD-NOS for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having PDD-NOS in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having PDD-NOS in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having PDD-NOS simultaneously or at spaced apart intervals.

In embodiments, methods include treating Asperger's syndrome by administering to a subject in need thereof about 1 mg to about 4000 mg of vigabatrin or a pharmaceutically acceptable salt thereof, e.g., a hydrochloride salt thereof. In embodiments, methods include treating Asperger's syndrome by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of Asperger's syndrome. In embodiments, the amount of vigabatrin or a pharmaceutically acceptable salt thereof, e.g., a hydrochloride salt thereof, for treatment of Asperger's syndrome can be between 50 and 3000 mg/day, or 0.7 mg/kg/day to 40 mg/kg/day. For example, the daily dosage for treatment of Asperger's syndrome can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating Asperger's syndrome may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having Asperger's syndrome once, twice, three or four times daily, every other day, once weekly, or once a month. In embodiments, vigabatrin or a pharmaceutically acceptable salt thereof is administered to a subject having Asperger's syndrome twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having Asperger's syndrome 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating Asperger's syndrome can be about 100 to 3000 mg per day and can be increased to 4000 mg per day. Dosages can be lower for infants and children than for adults. In embodiments, an infant or pediatric dose for treating Asperger's syndrome can be about 10 to 500 mg per day once or in 2, 3 or 4 divided doses. In embodiments, a pediatric dose for treating Asperger's syndrome can be 0.7 mg/kg/day to 150 mg/kg/day. In embodiments, the subject having Asperger's syndrome may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating Asperger's syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Asperger's syndrome are provided which include administering to a subject in need thereof a pharmaceutical composition including vigabatrin or a pharmaceutically acceptable salt thereof wherein the composition provides improvement in one or more symptoms of Asperger's syndrome for more than 1 hour after administration to the subject. In embodiments, methods of treating Asperger's syndrome are provided which include administering to a subject in need thereof a pharmaceutical composition including vigabatrin or a pharmaceutically acceptable salt thereof wherein the composition provides improvement in one or more symptoms of Asperger's syndrome for more than 2 hours after administration to the subject. In embodiments, methods of treating Asperger's syndrome are provided which include administering to a subject in need thereof a pharmaceutical composition including vigabatrin or a pharmaceutically acceptable salt thereof wherein the composition provides improvement in one or more symptoms of Asperger's syndrome for more than 3 hours after administration to the subject. In embodiments, methods of treating Asperger's syndrome are provided which include administering to a subject in need thereof a pharmaceutical composition including vigabatrin or a pharmaceutically acceptable salt thereof wherein the composition provides improvement in one or more symptoms of Asperger's syndrome for more than 4 hours after administration to the subject. In embodiments, methods of treating Asperger's syndrome are provided which include administering to a subject in need thereof a pharmaceutical composition including vigabatrin or a pharmaceutically acceptable salt thereof wherein the composition provides improvement in one or more symptoms of Asperger's syndrome for more than 6 hours after administration to the subject. In embodiments, methods of treating Asperger's syndrome are provided which include administering to a subject in need thereof a pharmaceutical composition including vigabatrin or a pharmaceutically acceptable salt thereof wherein the composition provides improvement in one or more symptoms of Asperger's syndrome for more than 8, 10, 12, 14, 16, 18, 20, 22 or 24 hours after administration to the subject. In embodiments, the pharmaceutical compositions for use in treating Asperger's syndrome provide improvement of next day functioning of the subject. For example, the pharmaceutical compositions may provide improvement in one or more symptoms of Asperger's syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having Asperger's syndrome in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having Asperger's syndrome in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having Asperger's syndrome simultaneously or at spaced apart intervals.

In embodiments, methods include treating Angelman syndrome by administering to a subject in need thereof about 1 mg to about 4000 mg of vigabatrin or a pharmaceutically acceptable salt thereof, e.g., a hydrochloride salt thereof. In embodiments, methods include treating Angelman syndrome by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of Angelman syndrome. In embodiments, the amount of vigabatrin or a pharmaceutically acceptable salt thereof, e.g., a hydrochloride salt thereof, for treatment of Angelman syndrome can be between 50 and 3000 mg/day, or 0.7 mg/kg/day to 40 mg/kg/day. For example, the daily dosage for treatment of Angelman syndrome can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating Angelman syndrome may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having Angelman syndrome once, twice, three or four times daily, every other day, once weekly, or once a month. In embodiments, vigabatrin or a pharmaceutically acceptable salt thereof is administered to a subject having Angelman syndrome twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having Angelman syndrome 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating Angelman syndrome can be about 100 to 3000 mg per day and can be increased to 4000 mg per day. Dosages can be lower for infants and children than for adults. In embodiments, an infant or pediatric dose for treating Angelman syndrome can be about 10 to 500 mg per day once or in 2, 3 or 4 divided doses. In embodiments, a pediatric dose for treating Angelman syndrome can be 0.7 mg/kg/day to 150 mg/kg/day. In embodiments, the subject having Angelman syndrome may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating Angelman syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Angelman syndrome are provided which include administering to a subject in need thereof a pharmaceutical composition including vigabatrin or a pharmaceutically acceptable salt thereof wherein the composition provides improvement in one or more symptoms of Angelman syndrome for more than 1 hour after administration to the subject. In embodiments, methods of treating Angelman syndrome are provided which include administering to a subject in need thereof a pharmaceutical composition including vigabatrin or a pharmaceutically acceptable salt thereof wherein the composition provides improvement in one or more symptoms of Angelman syndrome for more than 2 hours after administration to the subject. In embodiments, methods of treating Angelman syndrome are provided which include administering to a subject in need thereof a pharmaceutical composition including vigabatrin or a pharmaceutically acceptable salt thereof wherein the composition provides improvement in one or more symptoms of Angelman syndrome for more than 3 hours after administration to the subject. In embodiments, methods of treating Angelman syndrome are provided which include administering to a subject in need thereof a pharmaceutical composition including vigabatrin or a pharmaceutically acceptable salt thereof wherein the composition provides improvement in one or more symptoms of Angelman syndrome for more than 4 hours after administration to the subject. In embodiments, methods of treating Angelman syndrome are provided which include administering to a subject in need thereof a pharmaceutical composition including vigabatrin or a pharmaceutically acceptable salt thereof wherein the composition provides improvement in one or more symptoms of Angelman syndrome for more than 6 hours after administration to the subject. In embodiments, methods of treating Angelman syndrome are provided which include administering to a subject in need thereof a pharmaceutical composition including vigabatrin or a pharmaceutically acceptable salt thereof wherein the composition provides improvement in one or more symptoms of Angelman syndrome for more than 8, 10, 12, 14, 16, 18, 20, 22 or 24 hours after administration to the subject. In embodiments, the pharmaceutical compositions for use in treating Angelman syndrome provide improvement of next day functioning of the subject. For example, the pharmaceutical compositions may provide improvement in one or more symptoms of Angelman syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having Angelman syndrome in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having Angelman syndrome in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having Angelman syndrome simultaneously or at spaced apart intervals.

In embodiments, methods include treating Fragile X syndrome by administering to a subject in need thereof about 1 mg to about 4000 mg of vigabatrin or a pharmaceutically acceptable salt thereof, e.g., a hydrochloride salt thereof. In embodiments, methods include treating Fragile X syndrome by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of Fragile X syndrome. In embodiments, the amount of vigabatrin or a pharmaceutically acceptable salt thereof, e.g., a hydrochloride salt thereof, for treatment of Fragile X syndrome can be between 50 and 3000 mg/day, or 0.7 mg/kg/day to 40 mg/kg/day. For example, the daily dosage for treatment of Fragile X syndrome can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating Fragile X syndrome may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having Fragile X syndrome once, twice, three or four times daily, every other day, once weekly, or once a month. In embodiments, vigabatrin or a pharmaceutically acceptable salt thereof is administered to a subject having Fragile X syndrome twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having Fragile X syndrome 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating Fragile X syndrome can be about 100 to 3000 mg per day and can be increased to 4000 mg per day. Dosages can be lower for infants and children than for adults. In embodiments, an infant or pediatric dose for treating Fragile X syndrome can be about 10 to 500 mg per day once or in 2, 3 or 4 divided doses. In embodiments, a pediatric dose for treating Fragile X syndrome can be 0.7 mg/kg/day to 150 mg/kg/day. In embodiments, the subject having Fragile X syndrome may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating Fragile X syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Fragile X syndrome are provided which include administering to a subject in need thereof a pharmaceutical composition including vigabatrin or a pharmaceutically acceptable salt thereof wherein the composition provides improvement in one or more symptoms of Fragile X syndrome for more than 1 hour after administration to the subject. In embodiments, methods of treating Fragile X syndrome are provided which include administering to a subject in need thereof a pharmaceutical composition including vigabatrin or a pharmaceutically acceptable salt thereof wherein the composition provides improvement in one or more symptoms of Fragile X syndrome for more than 2 hours after administration to the subject. In embodiments, methods of treating Fragile X syndrome are provided which include administering to a subject in need thereof a pharmaceutical composition including vigabatrin or a pharmaceutically acceptable salt thereof wherein the composition provides improvement in one or more symptoms of Fragile X syndrome for more than 3 hours after administration to the subject. In embodiments, methods of treating Fragile X syndrome are provided which include administering to a subject in need thereof a pharmaceutical composition including vigabatrin or a pharmaceutically acceptable salt thereof wherein the composition provides improvement in one or more symptoms of Fragile X syndrome for more than 4 hours after administration to the subject. In embodiments, methods of treating Fragile X syndrome are provided which include administering to a subject in need thereof a pharmaceutical composition including vigabatrin or a pharmaceutically acceptable salt thereof wherein the composition provides improvement in one or more symptoms of Fragile X syndrome for more than 6 hours after administration to the subject. In embodiments, methods of treating Fragile X syndrome are provided which include administering to a subject in need thereof a pharmaceutical composition including vigabatrin or a pharmaceutically acceptable salt thereof wherein the composition provides improvement in one or more symptoms of Fragile X syndrome for more than 8, 10, 12, 14, 16, 18, 20, 22 or 24 hours after administration to the subject. In embodiments, the pharmaceutical compositions for use in treating Fragile X syndrome provide improvement of next day functioning of the subject. For example, the pharmaceutical compositions may provide improvement in one or more symptoms of Fragile X syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having Fragile X syndrome in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having Fragile X syndrome in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having Fragile X syndrome simultaneously or at spaced apart intervals.

In embodiments, methods include treating Fragile X-associated tremor/ataxia syndrome (FXTAS) by administering to a subject in need thereof about 1 mg to about 4000 mg of vigabatrin or a pharmaceutically acceptable salt thereof, e.g., a hydrochloride salt thereof. In embodiments, methods include treating FXTAS by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of FXTAS. In embodiments, the amount of vigabatrin or a pharmaceutically acceptable salt thereof, e.g., a hydrochloride salt thereof, for treatment of FXTAS can be between 50 and 3000 mg/day, or 0.7 mg/kg/day to 40 mg/kg/day. For example, the daily dosage for treatment of FXTAS can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating FXTAS may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having FXTAS once, twice, three or four times daily, every other day, once weekly, or once a month. In embodiments, vigabatrin or a pharmaceutically acceptable salt thereof is administered to a subject having FXTAS twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having FXTAS 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating FXTAS can be about 100 to 3000 mg per day and can be increased to 4000 mg per day. Dosages can be lower for infants and children than for adults. In embodiments, an infant or pediatric dose for treating FXTAS can be about 10 to 500 mg per day once or in 2, 3 or 4 divided doses. In embodiments, a pediatric dose for treating FXTAS can be 0.7 mg/kg/day to 150 mg/kg/day. In embodiments, the subject having FXTAS may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating FXTAS. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating FXTAS are provided which include administering to a subject in need thereof a pharmaceutical composition including vigabatrin or a pharmaceutically acceptable salt thereof wherein the composition provides improvement in one or more symptoms of FXTAS for more than 1 hour after administration to the subject. In embodiments, methods of treating FXTAS are provided which include administering to a subject in need thereof a pharmaceutical composition including vigabatrin or a pharmaceutically acceptable salt thereof wherein the composition provides improvement in one or more symptoms of FXTAS for more than 2 hours after administration to the subject. In embodiments, methods of treating FXTAS are provided which include administering to a subject in need thereof a pharmaceutical composition including vigabatrin or a pharmaceutically acceptable salt thereof wherein the composition provides improvement in one or more symptoms of FXTAS for more than 3 hours after administration to the subject. In embodiments, methods of treating FXTAS are provided which include administering to a subject in need thereof a pharmaceutical composition including vigabatrin or a pharmaceutically acceptable salt thereof wherein the composition provides improvement in one or more symptoms of FXTAS for more than 4 hours after administration to the subject. In embodiments, methods of treating FXTAS are provided which include administering to a subject in need thereof a pharmaceutical composition including vigabatrin or a pharmaceutically acceptable salt thereof wherein the composition provides improvement in one or more symptoms of FXTAS for more than 6 hours after administration to the subject. In embodiments, methods of treating FXTAS are provided which include administering to a subject in need thereof a pharmaceutical composition including vigabatrin or a pharmaceutically acceptable salt thereof wherein the composition provides improvement in one or more symptoms of FXTAS for more than 8, 10, 12, 14, 16, 18, 20, 22 or 24 hours after administration to the subject. In embodiments, the pharmaceutical compositions for use in treating FXTAS provide improvement of next day functioning of the subject. For example, the pharmaceutical compositions may provide improvement in one or more symptoms of FXTAS for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having FXTAS in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having FXTAS in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having FXTAS simultaneously or at spaced apart intervals.

In embodiments, methods include treating Childhood Disintegrative Disorder (CDD) by administering to a subject in need thereof about 1 mg to about 4000 mg of vigabatrin or a pharmaceutically acceptable salt thereof, e.g., a hydrochloride salt thereof. In embodiments, methods include treating CDD by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of CDD. In embodiments, the amount of vigabatrin or a pharmaceutically acceptable salt thereof, e.g., a hydrochloride salt thereof, for treatment of CDD can be between 50 and 3000 mg/day, or 0.7 mg/kg/day to 40 mg/kg/day. For example, the daily dosage for treatment of CDD can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating CDD may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having CDD once, twice, three or four times daily, every other day, once weekly, or once a month. In embodiments, vigabatrin or a pharmaceutically acceptable salt thereof is administered to a subject having CDD twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having CDD 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating CDD can be about 100 to 3000 mg per day and can be increased to 4000 mg per day. Dosages can be lower for infants and children than for adults. In embodiments, an infant or pediatric dose for treating CDD can be about 10 to 500 mg per day once or in 2, 3 or 4 divided doses. In embodiments, a pediatric dose for treating CDD can be 0.7 mg/kg/day to 150 mg/kg/day. In embodiments, the subject having CDD may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating CDD. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating CDD are provided which include administering to a subject in need thereof a pharmaceutical composition including vigabatrin or a pharmaceutically acceptable salt thereof wherein the composition provides improvement in one or more symptoms of CDD for more than 1 hour after administration to the subject. In embodiments, methods of treating CDD are provided which include administering to a subject in need thereof a pharmaceutical composition including vigabatrin or a pharmaceutically acceptable salt thereof wherein the composition provides improvement in one or more symptoms of CDD for more than 2 hours after administration to the subject. In embodiments, methods of treating CDD are provided which include administering to a subject in need thereof a pharmaceutical composition including vigabatrin or a pharmaceutically acceptable salt thereof wherein the composition provides improvement in one or more symptoms of CDD for more than 3 hours after administration to the subject. In embodiments, methods of treating CDD are provided which include administering to a subject in need thereof a pharmaceutical composition including vigabatrin or a pharmaceutically acceptable salt thereof wherein the composition provides improvement in one or more symptoms of CDD for more than 4 hours after administration to the subject. In embodiments, methods of treating CDD are provided which include administering to a subject in need thereof a pharmaceutical composition including vigabatrin or a pharmaceutically acceptable salt thereof wherein the composition provides improvement in one or more symptoms of CDD for more than 6 hours after administration to the subject. In embodiments, methods of treating CDD are provided which include administering to a subject in need thereof a pharmaceutical composition including vigabatrin or a pharmaceutically acceptable salt thereof wherein the composition provides improvement in one or more symptoms of CDD for more than 8, 10, 12, 14, 16, 18, 20, 22 or 24 hours after administration to the subject. In embodiments, the pharmaceutical compositions for use in treating CDD provide improvement of next day functioning of the subject. For example, the pharmaceutical compositions may provide improvement in one or more symptoms of CDD for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having CDD in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having CDD in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having CDD simultaneously or at spaced apart intervals.

In embodiments, methods include treating Williams syndrome by administering to a subject in need thereof about 1 mg to about 4000 mg of vigabatrin or a pharmaceutically acceptable salt thereof, e.g., a hydrochloride salt thereof. In embodiments, methods include treating Williams syndrome by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of Williams syndrome. In embodiments, the amount of vigabatrin or a pharmaceutically acceptable salt thereof, e.g., a hydrochloride salt thereof, for treatment of Williams syndrome can be between 50 and 3000 mg/day, or 0.7 mg/kg/day to 40 mg/kg/day. For example, the daily dosage for treatment of Williams syndrome can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating Williams syndrome may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having Williams syndrome once, twice, three or four times daily, every other day, once weekly, or once a month. In embodiments, vigabatrin or a pharmaceutically acceptable salt thereof is administered to a subject having Williams syndrome twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having Williams syndrome 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating Williams syndrome can be about 100 to 3000 mg per day and can be increased to 4000 mg per day. Dosages can be lower for infants and children than for adults. In embodiments, an infant or pediatric dose for treating Williams syndrome can be about 10 to 500 mg per day once or in 2, 3 or 4 divided doses. In embodiments, a pediatric dose for treating Williams syndrome can be 0.7 mg/kg/day to 150 mg/kg/day. In embodiments, the subject having Williams syndrome may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating Williams syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Williams syndrome are provided which include administering to a subject in need thereof a pharmaceutical composition including vigabatrin or a pharmaceutically acceptable salt thereof wherein the composition provides improvement in one or more symptoms of Williams syndrome for more than 1 hour after administration to the subject. In embodiments, methods of treating Williams syndrome are provided which include administering to a subject in need thereof a pharmaceutical composition including vigabatrin or a pharmaceutically acceptable salt thereof wherein the composition provides improvement in one or more symptoms of Williams syndrome for more than 2 hours after administration to the subject. In embodiments, methods of treating Williams syndrome are provided which include administering to a subject in need thereof a pharmaceutical composition including vigabatrin or a pharmaceutically acceptable salt thereof wherein the composition provides improvement in one or more symptoms of Williams syndrome for more than 3 hours after administration to the subject. In embodiments, methods of treating Williams syndrome are provided which include administering to a subject in need thereof a pharmaceutical composition including vigabatrin or a pharmaceutically acceptable salt thereof wherein the composition provides improvement in one or more symptoms of Williams syndrome for more than 4 hours after administration to the subject. In embodiments, methods of treating Williams syndrome are provided which include administering to a subject in need thereof a pharmaceutical composition including vigabatrin or a pharmaceutically acceptable salt thereof wherein the composition provides improvement in one or more symptoms of Williams syndrome for more than 6 hours after administration to the subject. In embodiments, methods of treating Williams syndrome are provided which include administering to a subject in need thereof a pharmaceutical composition including vigabatrin or a pharmaceutically acceptable salt thereof wherein the composition provides improvement in one or more symptoms of Williams syndrome for more than 8, 10, 12, 14, 16, 18, 20, 22 or 24 hours after administration to the subject. In embodiments, the pharmaceutical compositions for use in treating Williams syndrome provide improvement of next day functioning of the subject. For example, the pharmaceutical compositions may provide improvement in one or more symptoms of Williams syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having Williams syndrome in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having Williams syndrome in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having Williams syndrome simultaneously or at spaced apart intervals.

In embodiments, methods include treating Jacobsen syndrome by administering to a subject in need thereof about 1 mg to about 4000 mg of vigabatrin or a pharmaceutically acceptable salt thereof, e.g., a hydrochloride salt thereof. In embodiments, methods include treating Jacobsen syndrome by administering to a subject in need thereof about 100 mg to about 4000 mg of vigabatrin or a pharmaceutically acceptable salt thereof, e.g., a hydrochloride salt thereof. In embodiments, the amount of vigabatrin or a pharmaceutically acceptable salt thereof, e.g., a hydrochloride salt thereof, can be between 1 and 4000 mg/day, or 0.01 mg/kg/day to 55 mg/kg/day, for treatment of Jacobsen syndrome. In embodiments, the amount of vigabatrin or a pharmaceutically acceptable salt thereof, e.g., a hydrochloride salt thereof, for treatment of Jacobsen syndrome can be between 50 and 3000 mg/day, or 0.7 mg/kg/day to 40 mg/kg/day. For example, the daily dosage for treatment of Jacobsen syndrome can be, e.g., in the range of about 50 to 3000 mg, 50 to 2750 mg, 50 to 2500 mg, 50 to 2225 mg, 50 to 2000 mg, 50 to 1750 mg, 50 to 1500 mg, 50 to 1250 mg, 50 to 1000 mg, 50 to 750 mg, 50 to 500 mg, 50 to 450 mg, 50 to 400 mg, 50 to 350 mg, 50 to 300 mg, 50 to 250 mg, 50 to 200 mg, 50 to 175 mg, 50 to 150 mg, 50 to 125 mg, 50 to 100 mg, 50 to 75 mg, 100 to 3000 mg, 100 to 2750 mg, 100 to 2500 mg, 100 to 2225 mg, 100 to 2000 mg, 100 to 1750 mg, 100 to 1500 mg, 100 to 1250 mg, 100 to 1000 mg, 100 to 750 mg, 100 to 500 mg, 100 to 450 mg, 100 to 400 mg, 100 to 350 mg, 100 to 300 mg, 100 to 250 mg, 100 to 200 mg, 100 to 175 mg, 100 to 150 mg, 100 to 125 mg, 150 to 3000 mg, 150 to 2750 mg, 150 to 2500 mg, 150 to 2225 mg, 150 to 2000 mg, 150 to 1750 mg, 150 to 1500 mg, 150 to 1250 mg, 150 to 1000 mg, 150 to 750 mg, 150 to 500 mg, 150 to 450 mg, 150 to 400 mg, 150 to 350 mg, 150 to 300 mg, 150 to 250 mg, 150 to 200 mg, 150 to 175 mg, 200 to 3000 mg, 200 to 2750 mg, 200 to 2500 mg, 200 to 2225 mg, 200 to 2000 mg, 200 to 1750 mg, 200 to 1500 mg, 200 to 1250 mg, 200 to 1000 mg, 200 to 750 mg, 200 to 500 mg, 200 to 450 mg, 200 to 400 mg, 200 to 350 mg, 200 to 300 mg, 200 to 250 mg, 250 to 3000 mg, 250 to 2750 mg, 250 to 2500 mg, 250 to 2225 mg, 250 to 2000 mg, 250 to 1750 mg, 250 to 1500 mg, 250 to 1250 mg, 250 to 1000 mg, 250 to 750 mg, 250 to 500 mg, 250 to 450 mg, 250 to 400 mg, 250 to 350 mg, 250 to 300 mg, 300 to 3000 mg, 300 to 2750 mg, 300 to 2500 mg, 300 to 2225 mg, 300 to 2000 mg, 300 to 1750 mg, 300 to 1500 mg, 300 to 1250 mg, 300 to 1000 mg, 300 to 750 mg, 300 to 500 mg, 300 to 450 mg, 300 to 400 mg, 300 to 350 mg, 350 to 3000 mg, 350 to 2750 mg, 350 to 2500 mg, 350 to 2225 mg, 350 to 2000 mg, 350 to 1750 mg, 350 to 1500 mg, 350 to 1250 mg, 350 to 1000 mg, 350 to 750 mg, 350 to 500 mg, 350 to 450 mg, 350 to 400 mg, 400 to 3000 mg, 400 to 2750 mg, 400 to 2500 mg, 400 to 2225 mg, 400 to 2000 mg, 400 to 1750 mg, 400 to 1500 mg, 400 to 1250 mg, 400 to 1000 mg, 400 to 750 mg, 400 to 500 mg, 400 to 450 mg, 450 to 3000 mg, 450 to 2750 mg, 450 to 2500 mg, 450 to 2225 mg, 450 to 2000 mg, 450 to 1750 mg, 450 to 1500 mg, 450 to 1250 mg, 450 to 1000 mg, 450 to 750 mg, 450 to 500 mg, 500 to 3000 mg, 500 to 2750 mg, 500 to 2500 mg, 500 to 2225 mg, 500 to 2000 mg, 500 to 1750 mg, 500 to 1500 mg, 500 to 1250 mg, 500 to 1000 mg, 500 to 750 mg, 550 to 3000 mg, 550 to 2750 mg, 550 to 2500 mg, 550 to 2225 mg, 550 to 2000 mg, 550 to 1750 mg, 550 to 1500 mg, 550 to 1250 mg, 550 to 1000 mg, 550 to 750 mg, 600 to 3000 mg, 600 to 2750 mg, 600 to 2500 mg, 600 to 2225 mg, 600 to 2000 mg, 600 to 1750 mg, 600 to 1500 mg, 600 to 1250 mg, 600 to 1000 mg, 600 to 750 mg, 600 to 700 mg, 650 to 3000 mg, 650 to 2750 mg, 650 to 2500 mg, 650 to 2225 mg, 650 to 2000 mg, 650 to 1750 mg, 650 to 1500 mg, 650 to 1250 mg, 650 to 1000 mg, 650 to 750 mg, 700 to 3000 mg, 700 to 2750 mg, 700 to 2500 mg, 700 to 2225 mg, 700 to 2000 mg, 700 to 1750 mg, 700 to 1500 mg, 700 to 1250 mg, 700 to 1000 mg, 700 to 750 mg, 750 to 3000 mg, 750 to 2750 mg, 750 to 2500 mg, 750 to 2225 mg, 750 to 2000 mg, 750 to 1750 mg, 750 to 1500 mg, 750 to 1250 mg, 750 to 1000 mg, 800 to 3000 mg, 800 to 2750 mg, 800 to 2500 mg, 800 to 2225 mg, 800 to 2000 mg, 800 to 1750 mg, 800 to 1500 mg, 800 to 1250 mg, 800 to 1000 mg, 850 to 3000 mg, 850 to 2750 mg, 850 to 2500 mg, 850 to 2225 mg, 850 to 2000 mg, 850 to 1750 mg, 850 to 1500 mg, 850 to 1250 mg, 850 to 1000 mg, 900 to 3000 mg, 900 to 2750 mg, 900 to 2500 mg, 900 to 2225 mg, 900 to 2000 mg, 900 to 1750 mg, 900 to 1500 mg, 900 to 1250 mg, 900 to 1000 mg, with doses of, e.g., about 25 mg, 50 mg, 75 mg, 100 mg, 125 mg, 150 mg, 175 mg, 200 mg, 225 mg, 250 mg, 275 mg, 300 mg, 350 mg, 400 mg, 450 mg, 500 mg and 525 mg, being examples.

In embodiments, pharmaceutical compositions for use in treating Jacobsen syndrome may contain vigabatrin or a pharmaceutically acceptable salt thereof in an amount of, e.g., about 0.1 to 500 mg, 0.1 to 450 mg, 0.1 to 300 mg, 0.1 to 250 mg, 0.1 to 200 mg, 0.1 to 175 mg, 0.1 to 150 mg, 0.1 to 125 mg, 0.1 to 100 mg, 0.1 to 75 mg, 0.1 to 50 mg, 0.1 to 30 mg, 0.1 to 25 mg, 0.1 to 20 mg, 0.1 to 15 mg, 0.1 to 10 mg, 0.1 to 5 mg, 0.1 to 1 mg, 0.5 to 500 mg, 0.5 to 450 mg, 0.5 to 300 mg, 0.5 to 250 mg, 0.5 to 200 mg, 0.5 to 175 mg, 0.5 to 150 mg, 0.5 to 125 mg, 0.5 to 100 mg, 0.5 to 75 mg, 0.5 to 50 mg, 0.5 to 30 mg, 0.5 to 25 mg, 0.5 to 20 mg, 0.5 to 15 mg, 0.5 to 10 mg, 0.5 to 5 mg, 0.5 to 1 mg, 1 to 500 mg, 1 to 450 mg, 1 to 300 mg, 1 to 250 mg, 1 to 200 mg, 1 to 175 mg, 1 to 150 mg, 1 to 125 mg, 1 to 100 mg, 1 to 75 mg, 1 to 50 mg, 1 to 30 mg, 1 to 25 mg, 1 to 20 mg, 1 to 15 mg, 1 to 10 mg, 1 to 5 mg, 5 to 500 mg, 5 to 450 mg, 5 to 300 mg, 5 to 250 mg, 5 to 200 mg, 5 to 175 mg, 5 to 150 mg, 5 to 125 mg, 5 to 100 mg, 5 to 75 mg, 5 to 50 mg, 5 to 30 mg, 5 to 25 mg, 5 to 20 mg, 5 to 15 mg, 5 to 10 mg, 10 to 500 mg, 10 to 450 mg, 10 to 300 mg, 10 to 250 mg, 10 to 200 mg, 10 to 175 mg, 10 to 150 mg, 10 to 125 mg, 10 to 100 mg, 10 to 75 mg, 10 to 50 mg, 10 to 30 mg, 10 to 25 mg, 10 to 20 mg, 10 to 15 mg, 15 to 500 mg, 15 to 450 mg, 15 to 300 mg, 15 to 250 mg, 15 to 200 mg, 15 to 175 mg, 15 to 150 mg, 15 to 125 mg, 15 to 100 mg, 15 to 75 mg, 15 to 50 mg, 15 to 30 mg, 15 to 25 mg, 15 to 20 mg, 20 to 500 mg, 20 to 450 mg, 20 to 300 mg, 20 to 250 mg, 20 to 200 mg, 20 to 175 mg, 20 to 150 mg, 20 to 125 mg, 20 to 100 mg, 20 to 75 mg, 20 to 50 mg, 20 to 30 mg, 20 to 25 mg, 25 to 500 mg, 25 to 450 mg, 25 to 300 mg, 25 to 250 mg, 25 to 200 mg, 25 to 175 mg, 25 to 150 mg, 25 to 125 mg, 25 to 100 mg, 25 to 80 mg, 25 to 75 mg, 25 to 50 mg, 25 to 30 mg, 30 to 500 mg, 30 to 450 mg, 30 to 300 mg, 30 to 250 mg, 30 to 200 mg, 30 to 175 mg, 30 to 150 mg, 30 to 125 mg, 30 to 100 mg, 30 to 75 mg, 30 to 50 mg, 40 to 500 mg, 40 to 450 mg, 40 to 400 mg, 40 to 250 mg, 40 to 200 mg, 40 to 175 mg, 40 to 150 mg, 40 to 125 mg, 40 to 100 mg, 40 to 75 mg, 40 to 50 mg, 50 to 500 mg, 50 to 450 mg, 50 to 300 mg, 50 to 250 mg, 50 to 200 mg, 50 to 175 mg, 50 to 150 mg, 50 to 125 mg, 50 to 100 mg, 50 to 75 mg, 75 to 500 mg, 75 to 450 mg, 75 to 300 mg, 75 to 250 mg, 75 to 200 mg, 75 to 175 mg, 75 to 150 mg, 75 to 125 mg, 75 to 100 mg, 100 to 500 mg, 100 to 450 mg, 100 to 300 mg, 100 to 250 mg, 100 to 200 mg, 100 to 175 mg, 100 to 150 mg, 100 to 125 mg, 125 to 500 mg, 125 to 450 mg, 125 to 300 mg, 125 to 250 mg, 125 to 200 mg, 125 to 175 mg, 125 to 150 mg, 150 to 500 mg, 150 to 450 mg, 150 to 300 mg, 150 to 250 mg, 150 to 200 mg, 200 to 500 mg, 200 to 450 mg, 200 to 300 mg, 200 to 250 mg, 250 to 500 mg, 250 to 450 mg, 250 to 300 mg, 300 to 500 mg, 300 to 450 mg, 300 to 400 mg, 300 to 350 mg, 350 to 500 mg, 350 to 450 mg, 350 to 400 mg, 400 to 500 mg, 400 to 450 mg, with 0.1 mg, 0.25 mg, 0.5 mg, 0.75 mg, 1 mg, 2.5 mg, 5 mg, 7.5 mg, 10 mg, 12.5 mg, 15 mg, 17.5 mg, 20 mg, 22.5 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg 175 mg, 200 mg, 225 mg, 250 mg, 275 mg, 300 mg, 325 mg, 350 mg, 375 mg, 400 mg, 425 mg, 450 mg, 475 mg, and 500 mg being examples.

Typically, dosages may be administered to a subject having Jacobsen syndrome once, twice, three or four times daily, every other day, once weekly, or once a month. In embodiments, vigabatrin or a pharmaceutically acceptable salt thereof is administered to a subject having Jacobsen syndrome twice a day, (e.g., morning and evening), or three times a day (e.g., at breakfast, lunch, and dinner), at a dose of 1-500 mg/administration. In embodiments, vigabatrin or a pharmaceutically acceptable salt thereof is administered to a subject having Jacobsen syndrome 4000 mg/per day, 3000 mg/per day, 2750 mg/per day, 2500 mg/per day, 2250 mg/per day, 2000 mg/per day, 1750 mg/per day, 1500 mg/per day, 1250 mg/per day, 1000 mg/per day, 975 mg/per day, 950 mg/per day, 925 mg/per day, 900 mg/per day, 875 mg/per day, 850 mg/per day, 825 mg/per day, 800 mg/per day, 775 mg/per day, 750 mg/per day, 700 mg/per day, 675 mg/per day, 650 mg/per day, 625 mg/per day, 600 mg/per day, 575 mg/per day, 550 mg/per day, 525 mg/per day, 500 mg/per day, 475 mg/per day, 450 mg/per day, 425 mg/per day, 400 mg/per day, 375 mg/per day, 350 mg/per day, 325 mg/per day, 300 mg/per day, 275 mg/per day, 250 mg/per day, 225 mg/per day, 200 mg/per day, 175 mg/per day, 150 mg/per day, 125 mg/per day, 100 mg/per day, 95 mg/per day, 90 mg/per day, 85 mg/per day, 80 mg/per day, 75 mg/per day, 70 mg/per day, 65 mg/per day, 60 mg/per day, 55 mg/per day, 50 mg/per day, 45 mg/per day, 40 mg/per day, 35 mg/per day, 30 mg/per day, 25 mg/per day, 20 mg/per day, 15 mg/per day, 10 mg/per day, 5 mg/per day, 4 mg/per day, 3 mg/per day, 3 mg/per day, 2 mg/per day, 1 mg/per day, in one or more doses. In embodiments, an adult dose for treating Jacobsen syndrome can be about 100 to 3000 mg per day and can be increased to 4000 mg per day. Dosages can be lower for infants and children than for adults. In embodiments, an infant or pediatric dose for treating Jacobsen syndrome can be about 10 to 500 mg per day once or in 2, 3 or 4 divided doses. In embodiments, a pediatric dose for treating Jacobsen syndrome can be 0.7 mg/kg/day to 150 mg/kg/day. In embodiments, the subject having Jacobsen syndrome may be started at a low dose and the dosage is escalated over time. In embodiments, initial daily dosing can be 50 mg/kg/day given in two divided doses (25 mg/kg twice daily); subsequent dosing can be titrated by 25 mg/kg/day to 50 mg/kg/day increments every 3 days, up to a maximum of 150 mg/kg/day given in 2 divided doses (75 mg/kg twice daily).

In embodiments, vigabatrin or a pharmaceutically acceptable salt thereof is administered via a pharmaceutical composition for use in treating Jacobsen syndrome. Pharmaceutical compositions herein encompass dosage forms. Dosage forms herein encompass unit doses. In embodiments, as discussed below, various dosage forms including conventional formulations and modified release formulations can be administered one or more times daily. Any suitable route of administration may be utilized, e.g., oral, rectal, nasal, pulmonary, vaginal, sublingual, transdermal, intravenous, intraarterial, intramuscular, intraperitoneal and subcutaneous routes. Suitable dosage forms include tablets, capsules, oral liquids, powders, aerosols, transdermal modalities such as topical liquids, patches, creams and ointments, parenteral formulations and suppositories.

In embodiments, methods of treating Jacobsen syndrome are provided which include administering to a subject in need thereof a pharmaceutical composition including vigabatrin or a pharmaceutically acceptable salt thereof wherein the composition provides improvement in one or more symptoms of Jacobsen syndrome for more than 1 hour after administration to the subject. In embodiments, methods of treating Jacobsen syndrome are provided which include administering to a subject in need thereof a pharmaceutical composition including vigabatrin or a pharmaceutically acceptable salt thereof wherein the composition provides improvement in one or more symptoms of Jacobsen syndrome for more than 2 hours after administration to the subject. In embodiments, methods of treating FXTAS are provided which include administering to a subject in need thereof a pharmaceutical composition including vigabatrin or a pharmaceutically acceptable salt thereof wherein the composition provides improvement in one or more symptoms of Jacobsen syndrome for more than 3 hours after administration to the subject. In embodiments, methods of treating Jacobsen syndrome are provided which include administering to a subject in need thereof a pharmaceutical composition including vigabatrin or a pharmaceutically acceptable salt thereof wherein the composition provides improvement in one or more symptoms of Jacobsen syndrome for more than 4 hours after administration to the subject. In embodiments, methods of treating Jacobsen syndrome are provided which include administering to a subject in need thereof a pharmaceutical composition including vigabatrin or a pharmaceutically acceptable salt thereof wherein the composition provides improvement in one or more symptoms of Jacobsen syndrome for more than 6 hours after administration to the subject. In embodiments, methods of treating FXTAS are provided which include administering to a subject in need thereof a pharmaceutical composition including vigabatrin or a pharmaceutically acceptable salt thereof wherein the composition provides improvement in one or more symptoms of Jacobsen syndrome for more than 8, 10, 12, 14, 16, 18, 20, 22 or 24 hours after administration to the subject. In embodiments, the pharmaceutical compositions for use in treating Jacobsen syndrome provide improvement of next day functioning of the subject. For example, the pharmaceutical compositions may provide improvement in one or more symptoms of Jacobsen syndrome for more than about, e.g., 2 hours, 4 hours, 6 hours, 8 hours, 10 hours, 12 hours, 14 hours, 16 hours, 18 hours, 20 hours, 22 hours or 24 hours after administration and waking from a night of sleep.

In embodiments, vigabatrin or a pharmaceutically acceptable salt thereof may be administered to a subject having Jacobsen syndrome in combination with one or more of (S)-3-amino-4-(difluoromethylenyl)cyclopent-1-ene-1-carboxylic acid or a pharmaceutically acceptable salt thereof, or (1S,3S)-3-amino-4-(difluoromethylidene)cyclopentane-1-carboxylic acid or a pharmaceutically acceptable salt thereof. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be administered to a subject having Jacobsen syndrome in separate dosage forms or combined in one dosage form. In embodiments, vigabatrin or a pharmaceutically acceptable salt thereof, (S)-3-amino-4-(difluoromethylenyl)cyclopent-1-ene-1-carboxylic acid or a pharmaceutically acceptable salt thereof, and (1S,3S)-3-amino-4-(difluoromethylidene)cyclopentane-1-carboxylic acid or a pharmaceutically acceptable salt thereof, may be co-administered to a subject having Jacobsen syndrome simultaneously or at spaced apart intervals.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof (1S,3S)-3-amino-4-(difluoromethylidene)cyclopentane-1-carboxylic acid or a pharmaceutically acceptable salt thereof, either alone or in combination with one or more of a compound of Formula 1 or a pharmaceutically acceptable salt thereof, (S)-3-amino-4-(difluoromethylenyl)cyclopent-1-ene-1-carboxylic acid or vigabatrin ((RS)-4-aminohex-5-enoic acid) or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with one or more of Formula 1 or a pharmaceutically acceptable salt thereof, (S)-3-amino-4-(difluoromethylenyl)cyclopent-1-ene-1-carboxylic acid or vigabatrin ((RS)-4-aminohex-5-enoic acid) or a pharmaceutically acceptable salt of any of the preceding, is reduced by more than 50% and the method provides improvement in the subject for more than 10, 12, 14, 16, 18, 20, 22 or 24 hours after administration. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof (S)-3-amino-4-(difluoromethylenyl)cyclopent-1-ene-1-carboxylic acid or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or vigabatrin ((RS)-4-aminohex-5-enoic acid) or a pharmaceutically acceptable salt of any of the preceding, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or vigabatrin ((RS)-4-aminohex-5-enoic acid) or a pharmaceutically acceptable salt of any of the preceding, is reduced by more than 50% and the method provides improvement in the subject for more than 10, 12, 14, 16, 18, 20, 22 or 24 hours after administration. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof vigabatrin ((RS)-4-aminohex-5-enoic acid) or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration vigabatrin ((RS)-4-aminohex-5-enoic acid) or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or (S)-3-amino-4-(difluoromethylenyl)cyclopent-1-ene-1-carboxylic acid or a pharmaceutically acceptable salt of any of the preceding, is reduced by more than 50% and the method provides improvement in the subject for more than 10, 12, 14, 16, 18, 20, 22 or 24 hours after administration.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof (1S,3S)-3-amino-4-(difluoromethylidene)cyclopentane-1-carboxylic acid or a pharmaceutically acceptable salt thereof, either alone or in combination with one or more of a compound of Formula 1 or a pharmaceutically acceptable salt thereof, (S)-3-amino-4-(difluoromethylenyl)cyclopent-1-ene-1-carboxylic acid or vigabatrin ((RS)-4-aminohex-5-enoic acid) or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with one or more of a compound of Formula 1 or a pharmaceutically acceptable salt thereof, (S)-3-amino-4-(difluoromethylenyl)cyclopent-1-ene-1-carboxylic acid or vigabatrin ((RS)-4-aminohex-5-enoic acid) or a pharmaceutically acceptable salt of any of the preceding, is reduced by more than 55% and the method provides improvement in the subject for more than 10, 12, 14, 16, 18, 20, 22 or 24 hours after administration. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof (S)-3- amino-4-(difluoromethylenyl)cyclopent-1-ene-1-carboxylic acid or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or vigabatrin ((RS)-4-aminohex-5-enoic acid) or a pharmaceutically acceptable salt of any of the preceding, which provides an in vivo plasma profile, wherein the in vivo plasma profile of the subject 10 hours after administration of (S)-3-amino-4-(difluoromethylenyl) cyclopent-1-ene-1-carboxylic acid or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or vigabatrin ((RS)-4-aminohex-5-enoic acid) or a pharmaceutically acceptable salt of any of the preceding, is reduced by more than 55% and the method provides improvement in the subject for more than 10, 12, 14, 16, 18, 20, 22 or 24 hours after administration. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof vigabatrin ((RS)-4-aminohex-5-enoic acid) or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration vigabatrin ((RS)-4-aminohex-5-enoic acid) or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or (S)-3-amino-4-(difluoromethylenyl)cyclopent-1-ene-1-carboxylic acid or a pharmaceutically acceptable salt of any of the preceding, is reduced by more than 55% and the method provides improvement in the subject for more than 10, 12, 14, 16, 18, 20, 22 or 24 hours after administration.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof (1S,3S)-3-amino-4-(difluoromethylidene)cyclopentane-1-carboxylic acid or a pharmaceutically acceptable salt thereof, either alone or in combination with one or more of a compound of Formula 1 or a pharmaceutically acceptable salt thereof, (S)-3-amino-4-(difluoromethylenyl)cyclopent-1-ene-1-carboxylic acid or vigabatrin ((RS)-4-aminohex-5-enoic acid) or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with one or more of a compound of Formula 1 or a pharmaceutically acceptable salt thereof, (S)-3-amino-4-(difluoromethylenyl)cyclopent-1-ene-1-carboxylic acid or vigabatrin ((RS)-4-aminohex-5-enoic acid) or a pharmaceutically acceptable salt of any of the preceding, is reduced by more than 60% and the method provides improvement in the subject for more than 10, 12, 14, 16, 18, 20, 22 or 24 hours after administration. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof (S)-3-amino-4-(difluoromethylenyl)cyclopent-1-ene-1-carboxylic acid or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or vigabatrin ((RS)-4-aminohex-5-enoic acid) or a pharmaceutically acceptable salt of any of the preceding, which provides an in vivo plasma profile, wherein the in vivo plasma profile of the subject 10 hours after administration of (S)-3-amino-4-(difluoromethylenyl) cyclopent-1-ene-1-carboxylic acid or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or vigabatrin ((RS)-4-aminohex-5-enoic acid) or a pharmaceutically acceptable salt of any of the preceding, is reduced by more than 60% and the method provides improvement in the subject for more than 10, 12, 14, 16, 18, 20, 22 or 24 hours after administration. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof vigabatrin ((RS)-4-aminohex-5-enoic acid) or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration vigabatrin ((RS)-4-aminohex-5-enoic acid) or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or (S)-3-amino-4-(difluoromethylenyl)cyclopent-1-ene-1-carboxylic acid or a pharmaceutically acceptable salt of any of the preceding, is reduced by more than 60% and the method provides improvement in the subject for more than 10, 12, 14, 16, 18, 20, 22 or 24 hours after administration.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof (1S,3S)-3-amino-4-(difluoromethylidene)cyclopentane-1-carboxylic acid or a pharmaceutically acceptable salt thereof, either alone or in combination with one or more of a compound of Formula 1 or a pharmaceutically acceptable salt thereof, (S)-3-amino-4-(difluoromethylenyl)cyclopent-1-ene-1-carboxylic acid or vigabatrin ((RS)-4-aminohex-5-enoic acid) or a pharmaceutically acceptable salt of any of the preceding, which provides an in vivo plasma profile, wherein the in vivo plasma profile of the subject 10 hours after administration of (1S,3S)-3-amino-4-(difluoromethylidene)cyclopentane-1-carboxylic acid or a pharmaceutically acceptable salt thereof, either alone or in combination with one or more of a compound of Formula 1 or a pharmaceutically acceptable salt thereof, (S)-3-amino-4-(difluoromethylenyl)cyclopent-1-ene-1-carboxylic acid or vigabatrin ((RS)-4-aminohex-5-enoic acid) or a pharmaceutically acceptable salt of any of the preceding, is reduced by more than 65% and the method provides improvement in the subject for more than 10, 12, 14, 16, 18, 20, 22 or 24 hours after administration. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof (S)-3-amino-4-(difluoromethylenyl)cyclopent-1-ene-1-carboxylic acid or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or vigabatrin ((RS)-4-aminohex-5-enoic acid) or a pharmaceutically acceptable salt of any of the preceding, which provides an in vivo plasma profile, wherein the in vivo plasma profile of the subject 10 hours after administration of (S)-3-amino-4-(difluoromethylenyl)cyclopent-1-ene-1-carboxylic acid or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or vigabatrin ((RS)-4-aminohex-5-enoic acid) or a pharmaceutically acceptable salt of any of the preceding, is reduced by more than 65% and the method provides improvement in the subject for more than 10, 12, 14, 16, 18, 20, 22 or 24 hours after administration. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof vigabatrin ((RS)-4-aminohex-5-enoic acid) or a pharmaceutically acceptable salt thereof, either alone or in combination with one or more Formula 1 or a pharmaceutically acceptable salt thereof, (1S,3S)-3-amino-4-(difluoromethylidene)cyclopentane-1-carboxylic acid or (S)-3-amino-4-(difluoromethylenyl)cyclopent-1-ene-1-carboxylic acid or a pharmaceutically acceptable salt of any of the preceding, which provides an in vivo plasma profile, wherein the in vivo plasma profile of the subject 10 hours after administration vigabatrin ((RS)-4-aminohex-5-enoic acid) or a pharmaceutically acceptable salt thereof, either alone or in combination with one or more of a compound of Formula 1 or a pharmaceutically acceptable salt thereof, (1S,3S)-3-amino-4-(difluoromethylidene)cyclopentane-1-carboxylic acid or (S)-3-amino-4-(difluoromethylenyl)cyclopent-1-ene-1-carboxylic acid or a pharmaceutically acceptable salt of any of the preceding, is reduced by more than 65% and the method provides improvement in the subject for more than 10, 12, 14, 16, 18, 20, 22 or 24 hours after administration.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome wherein the amount of active substance, e.g., (1S,3S)-3-amino-4-(difluoromethylidene)cyclopentane-1-carboxylic acid, (S)-3-amino-4-(difluoromethylenyl)cyclopent-1-ene-1-carboxylic acid, a compound of Formula 1 or a pharmaceutically acceptable salt thereof or vigabatrin ((RS)-4-aminohex-5-enoic acid), or a pharmaceutically acceptable salt of any of the preceding, individually or in any combination, within the subject about 4 hours after administration of the pharmaceutical composition is less than about 75% of the administered dose. In embodiments, provided herein are methods wherein the amount of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, individually or in any combination, within the subject about, e.g., 6 hours, 8 hours, 10 hours, 12 hours, 15 hours, or 20 hours after administration of the pharmaceutical composition is less than about 75%.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome wherein the amount of active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, individually or in any combination, within the subject about 4 hours after administration of the pharmaceutical composition is less than about 80% of the administered dose. In embodiments, provided herein are methods wherein the amount of active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, individually or in any combination, within the subject about, e.g., 6 hours, 8 hours, 10 hours, 12 hours, 15 hours, or 20 hours after administration of the pharmaceutical composition is less than about 80% of the administered dose.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome wherein the amount of active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, individually or in any combination, within the subject about 4 hours after administration of the pharmaceutical composition is between about 65% to about 85% of the administered dose. In embodiments, the amount of active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, individually or in any combination, within the subject after about, e.g., 6 hours, 8 hours, 10 hours, 12 hours, 15 hours, or 20 hours after administration of the pharmaceutical composition is between about 65% to about 85% of the administered dose.

In embodiments, the pharmaceutical compositions described herein may be administered once daily, twice daily, three times daily, four times daily, or every other day. In embodiments, the pharmaceutical compositions described herein may be administered by continuous infusion. In embodiments, a pharmaceutical composition described herein is provided to the subject in the morning. In embodiments, a pharmaceutical composition described herein is provided to the subject in the evening. In embodiments, a pharmaceutical composition described herein is provided to the subject once in the evening and once in the morning. In embodiments, a pharmaceutical composition described herein is provided to the subject once in the morning, once in the afternoon and once in the evening.

In embodiments, as mentioned previously, pharmaceutical compositions herein may be provided with conventional release or modified release profiles. Pharmaceutical compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions. Those with skill in the art are familiar with such pharmaceutical carriers and methods of compounding pharmaceutical compositions using such carriers.

In embodiments, pharmaceutical compositions herein are modified release dosage forms which provide modified release profiles. Modified release profiles may exhibit immediate release, delayed release, or extended release profiles. Conventional (or unmodified) release oral dosage forms such as tablets, capsules, suppositories, syrups, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Subjects with Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which one or more of (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, is applied to beads, e.g., confectioners nonpareil beads, and then coated with conventional release retarding materials such as waxes, enteric coatings and the like. In embodiments, beads can be formed in which one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, is mixed with a material to provide a mass from which the drug leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

In embodiments, modified dosage forms herein incorporate delayed release dosage forms having delayed release profiles. Delayed release dosage forms can include delayed release tablets or delayed release capsules. A delayed release tablet is a solid dosage form which releases a drug (or drugs) such as one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, at a time other than promptly after administration. A delayed release capsule is a solid dosage form in which the drug is enclosed within either a hard or soft soluble container made from a suitable form of gelatin, and which releases a drug (or drugs) at a time other than promptly after administration. For example, enteric-coated tablets, capsules, particles and beads are well-known examples of delayed release dosage forms. Enteric coated tablets, capsules and particles and beads pass through the stomach and release the drug in the intestine. In embodiments, a delayed release tablet is a solid dosage form containing a conglomerate of medicinal particles that releases a drug (or drugs) at a time other than promptly after administration. In embodiments, the conglomerate of medicinal particles are covered with a coating which delays release of the drug. In embodiments, a delayed release capsule is a solid dosage form containing a conglomerate of medicinal particles that releases a drug (or drugs) at a time other than promptly after administration. In embodiments, the conglomerate of medicinal particles are covered with a coating which delays release of the drug.

Delayed release dosage forms are known to those skilled in the art. For example, coated delayed release beads or granules in which one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, is applied to beads, e.g., confectioners nonpareil beads, and then coated with conventional release delaying materials such as waxes, enteric coatings and the like. In embodiments, beads can be formed in which one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, is mixed with a material to provide a mass from which the drug leaches out. In embodiments, the beads may be engineered to provide different rates of release by varying characteristics of the coating or mass, e.g., thickness, porosity, using different materials, etc. In embodiments, enteric coated granules of one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, can be contained in an enterically coated capsule or tablet which releases the granules in the small intestine. In embodiments, the granules have a coating which remains intact until the coated granules reach at least the ileum and thereafter provide a delayed release of the drug in the colon. Suitable enteric coating materials are well known in the art, e.g., Eudragit® coatings such methacrylic acid and methyl methacrylate polymers and others. The granules can be contained in capsules or compressed into tablets.

In embodiments, one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, is incorporated into porous inert carriers that provide delayed release profiles. In embodiments, the porous inert carriers incorporate channels or passages from which the drug diffuses into surrounding fluids. In embodiments, one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, is incorporated into an ion-exchange resin to provide a delayed release profile. Delayed action may result from a predetermined rate of release of the drug from the resin when the drug-resin complex contacts gastrointestinal fluids and the ionic constituents dissolved therein. In embodiments, membranes are utilized to control rate of release from drug containing reservoirs. In embodiments, liquid preparations may also be utilized to provide a delayed release profile. For example, a liquid preparation consisting of solid particles dispersed throughout a liquid phase in which the particles are not soluble. The suspension is formulated to allow at least a reduction in dosing frequency as compared to that drug presented as a conventional dosage form (e.g., as a solution or a prompt drug-releasing, conventional solid dosage form). For example, a suspension of ion-exchange resin constituents or microbeads.

In embodiments, pharmaceutical compositions described herein are suitable for parenteral administration, including, e.g., intramuscular (i.m.), intravenous (i.v.), subcutaneous (s.c.), intraperitoneal (i.p.), or intrathecal (i.t.). Parenteral compositions must be sterile for administration by injection, infusion or implantation into the body and may be packaged in either single-dose or multi-dose containers. In embodiments, liquid pharmaceutical compositions for parenteral administration to a subject include an active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, in any of the respective amounts described above. In embodiments, the pharmaceutical compositions for parenteral administration are formulated as a total volume of about, e.g., 10 ml, 20 ml, 25 ml, 50 ml, 100 ml, 200 ml, 250 ml, or 500 ml. In embodiments, the compositions are contained in a bag, a glass vial, a plastic vial, or a bottle.

In embodiments, pharmaceutical compositions for parenteral administration include respective amounts described above for a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, and vigabatrin ((RS)-4-aminohex-5-enoic acid), or a pharmaceutically acceptable salt of any of the preceding. In embodiments, pharmaceutical compositions for parenteral administration include about 0.05 mg to about 500 mg active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding. In embodiments, pharmaceutical compositions for parenteral administration to a subject include an active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, at a respective concentration of about 0.005 mg/ml to about 500 mg/ml. In embodiments, the pharmaceutical composition for parenteral administration includes an active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, at a respective concentration of, e.g., about 0.05 mg/ml to about 50 mg/ml, about 0.1 mg/ml to about 50 mg/ml, about 0.1 mg/ml to about 10 mg/ml, about 0.05 mg/ml to about 25 mg/ml, about 0.05 mg/ml to about 10 mg/ml, about 0.05 mg/ml to about 5 mg/ml, or about 0.05 mg/ml to about 1 mg/ml. In embodiments, the pharmaceutical composition for parenteral administration includes an active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, at a respective concentration of, e.g., about 0.05 mg/ml to about 15 mg/ml, about 0.5 mg/ml to about 10 mg/ml, about 0.25 mg/ml to about 5 mg/ml, about 0.5 mg/ml to about 7 mg/ml, about 1 mg/ml to about 10 mg/ml, about 5 mg/ml to about 10 mg/ml, or about 5 mg/ml to about 15 mg/ml.

In embodiments, a pharmaceutical composition for parenteral administration is provided wherein the pharmaceutical composition is stable for at least six months. In embodiments, the pharmaceutical compositions for parenteral administration exhibit no more than about 5% decrease in active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, e.g., 3 months or 6 months. In embodiments, the amount of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, degrades at no more than about, e.g., 2.5%, 1%, 0.5% or 0.1%. In embodiments, the degradation is less than about, e.g., 5%, 2.5%, 1%, 0.5%, 0.25%, 0.1%, for at least six months.

In embodiments, pharmaceutical compositions for parenteral administration are provided wherein the pharmaceutical composition remains soluble. In embodiments, pharmaceutical compositions for parenteral administration are provided that are stable, soluble, local site compatible and/or ready-to-use. In embodiments, the pharmaceutical compositions herein are ready-to-use for direct administration to a subject in need thereof.

The pharmaceutical compositions for parenteral administration provided herein may include one or more excipients, e.g., solvents, solubility enhancers, suspending agents, buffering agents, isotonicity agents, stabilizers or antimicrobial preservatives. When used, the excipients of the parenteral compositions will not adversely affect the stability, bioavailability, safety, and/or efficacy of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, used in the composition. Thus, parenteral compositions are provided wherein there is no incompatibility between any of the components of the dosage form.

In embodiments, parenteral compositions including a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, include a stabilizing amount of at least one excipient. For example, excipients may be selected from the group consisting of buffering agents, solubilizing agents, tonicity agents, antioxidants, chelating agents, antimicrobial agents, and preservative. One skilled in the art will appreciate that an excipient may have more than one function and be classified in one or more defined group.

In embodiments, parenteral compositions including a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, and an excipient wherein the excipient is present at a weight percent (w/v) of less than about, e.g., 10%, 5%, 2.5%, 1%, or 0.5%. In embodiments, the excipient is present at a weight percent between about, e.g., 1.0% to 10%, 10% to 25%, 15% to 35%, 0.5% to 5%, 0.001% to 1%, 0.01% to 1%, 0.1% to 1%, or 0.5% to 1%. In embodiments, the excipient is present at a weight percent between about, e.g., 0.001% to 1%, 0.01% to 1%, 1.0% to 5%, 10% to 15%, or 1% to 15%.

In embodiments, parenteral compositions may be administered as needed, e.g., once, twice, thrice or four or more times daily, or continuously depending on the subject's needs.

In embodiments, parenteral compositions of an active substance, e.g., a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, are provided, wherein the pH of the composition is between about 4.0 to about 8.0. In embodiments, the pH of the compositions is between, e.g., about 5.0 to about 8.0, about 6.0 to about 8.0, about 6.5 to about 8.0. In embodiments, the pH of the compositions is between, e.g., about 6.5 to about 7.5, about 7.0 to about 7.8, about 7.2 to about 7.8, or about 7.3 to about 7.6. In embodiments, the pH of the aqueous solution is, e.g., about 6.8, about 7.0, about 7.2, about 7.4, about 7.6, about 7.7, about 7.8, about 8.0, about 8.2, about 8.4, or about 8.6.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof a pharmaceutical composition including an active substance, e.g., one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, in a respective amount described herein, wherein the composition provides an in vivo plasma profile having a $C_{max}$ less than about 800 ng/ml. In embodiments, the composition provides improvement for more than 6 hours after administration to the subject.

In embodiments, pharmaceutical compositions including one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, provide an in vivo plasma profile having a $C_{max}$ less than about, e.g., 2000 ng/ml, 1000 ng/ml, 850 ng/ml, 800 ng/ml, 750 ng/ml, 700 ng/ml, 650 ng/ml, 600 ng/ml, 550 ng/ml, 450 ng/ml, 400 ng/ml 350 ng/ml, or 300 ng/ml and wherein the composition provides improvement of next day functioning of the subject. In embodiments, the pharmaceutical composition provides an in vivo plasma profile having a $C_{max}$ less than about, e.g., 250 ng/ml, 200 ng/ml 150 ng/ml, or 100 ng/ml and wherein the composition provides improvement of next day functioning of the subject. In embodiments, the pharmaceutical composition provides improvement in one or more symptoms of a disorder herein for more than 6 hours after administration.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof a pharmaceutical composition containing one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, wherein the composition provides a consistent in vivo plasma profile having a $AUC_{0-\infty}$ of less than about 900 ng·hr/ml. In embodiments, the pharmaceutical composition provides improvement in next day functioning of the subject. In embodiments, the compositions provide an in vivo plasma profile having a $AUC_{0-\infty}$ of less than about, e.g., 850 ng·hr/ml, 800 ng·hr/ml, 750 ng·hr/ml, or 700 ng·hr/ml and wherein the pharmaceutical composition provides improvement of next day functioning of the subject. In embodiments, the composition provides improvement in one or more symptoms of a disorder herein for more than 6 hours after administration.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof a pharmaceutical composition comprising an active substance, e.g., one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, wherein the pharmaceutical composition provides an in vivo plasma profile having a $AUC_{0-\infty}$ of less than about, e.g., 650 ng·hr/ml, 600 ng·hr/ml, 550 ng·hr/ml, 500 ng·hr/ml, or 450 ng·hr/ml. In embodiments, the composition provides an in vivo plasma profile having a $AUC_{0-\infty}$ of less than about, e.g., 400 ng·hr/ml, 350 ng·hr/ml, 300 ng·hr/ml, 250 ng·hr/ml, or 200 ng·hr/ml. In embodiments, the pharmaceutical composition provides an in vivo plasma profile having a $AUC_{0-\infty}$ of less than about, e.g., 150 ng·hr/ml, 100 ng·hr/ml, 75 ng·hr/ml, or 50 ng·hr/ml. In embodiments, the pharmaceutical composition provides improvement of next day functioning of the subject after administration for more than, e.g., 4 hours, 6 hours, 8 hours, 10 hours, or 12 hours, after administration of the composition to the subject.

In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof a first pharmaceutical composition including one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, and a second pharmaceutical composition including one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding.

In embodiments, the second pharmaceutical composition provides an in vivo plasma profile having a mean $AUC_{0-\infty}$ which is about the same as the mean $AUC_{0-\infty}$ of the first pharmaceutical composition. In embodiments, the second pharmaceutical composition provides an in vivo plasma profile having a mean $AUC_{0-\infty}$ of at least about 20% less than the first pharmaceutical composition. In embodiments, provided herein are methods of treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome which include administering to a subject in need thereof a first pharmaceutical composition including one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, and a second pharmaceutical composition including one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, wherein the second pharmaceutical composition provides a stable in vivo plasma profile having a mean $AUC_{0-\infty}$ of at least about, e.g., 25%, 30%, 35%, 40%, 45% or 50% less than the first pharmaceutical composition. In embodiments, the compositions provide improvement of next day functioning of the subject. For example, the pharmaceutical compositions may provide improvement in one or more symptoms for more than about, e.g., 6 hours, 8 hours, 10 hours, 12 hours, 14 hours, 16 hours, 18 hours, 20 hours, 22 hours or 24 hours after administration of the first and/or second pharmaceutical composition.

In embodiments, provided herein are methods of treating Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome which include administering to a subject in need thereof a first pharmaceutical composition including one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, and a second pharmaceutical composition including one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid), or vigabatrin ((RS)-4-aminohex-5-enoic acid), or a pharmaceutically acceptable salt of any of the preceding, wherein the second pharmaceutical composition provides an in vivo plasma profile having a mean $AUC_{0-\infty}$ of less than about 900 ng·hr/ml. In embodiments, the second pharmaceutical composition provides an in vivo plasma profile having a $AUC_{0-\infty}$ of less than about, e.g., 800 ng·hr/ml, 750 ng·hr/ml, 700 ng·hr/ml, 650 ng·hr/ml, or 600 ng·hr/ml. In embodiments, the second pharmaceutical composition provides an in vivo plasma profile having a $AUC_{0-\infty}$ of less than about, e.g., 550 ng·hr/ml, 500 ng·hr/ml, 450 ng·hr/ml, 400 ng·hr/ml, or 350 ng·hr/ml. In embodiments, the second pharmaceutical composition provides an in vivo plasma profile having a $AUC_{0-\infty}$ of less than about, e.g., 300 ng·hr/ml, 250 ng·hr/ml, 200 ng·hr/ml, 150 ng·hr/ml, or 100 ng·hr/ml. In embodiments, the first and second pharmaceutical composition are administered wherein the compositions provide improvement of next day functioning of the subject. In embodiments, the first pharmaceutical composition provides improvement in one or more symptom for more than, e.g., 6 hours, 8 hours, 10 hours, 12 hours, 14 hours, 16 hours, 18 hours, 20 hours, 22 hours or 24 hours after administration of the first pharmaceutical composition.

In embodiments, provided herein are methods of treating Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome which include administering to a subject in need thereof a first pharmaceutical composition including one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, and a second pharmaceutical composition including one or more of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic, or vigabatrin ((RS)-4-aminohex-5-enoic acid), or a pharmaceutically acceptable salt of any of the preceding, wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour. In embodiments, the $T_{max}$ of the first pharmaceutical composition is less than 0.5 hour. In embodiments, the $T_{max}$ of the first pharmaceutical composition is less than 0.25 hour. In embodiments, the $T_{max}$ of the second pharmaceutical composition is less than 3 hours. In embodiments, the $T_{max}$ of the second pharmaceutical composition is less than 2.5 hours. In embodiments, the $T_{max}$ of the second pharmaceutical composition is less than 2 hours. In embodiments, the $T_{max}$ of the second pharmaceutical composition is less than 1.5 hours. In embodiments, the $T_{max}$ of the second pharmaceutical composition is less than 1 hour. In embodiments, the $T_{max}$ of the second pharmaceutical composition is less than 0.5 hour. In embodiments, the $T_{max}$ of the second pharmaceutical composition is less than 0.25 hour.

In embodiments, the first pharmaceutical composition provides a dissolution of at least about 80% within the first 20 minutes of administration to a subject in need thereof. In embodiments, the first pharmaceutical composition provides a dissolution of at least about, e.g., 85%, 90% or 95% within the first 20 minutes of administration to a subject in need thereof. In embodiments, the first pharmaceutical composition provides a dissolution of at least 80% within the first 10 minutes of administration to a subject in need thereof.

In embodiments, administration of the first and second pharmaceutical compositions may be simultaneous or separated by an interval of time to achieve long-term improvement in at least one symptom. In embodiments, the first and second pharmaceutical composition may be administered 1, 2, 3, 4, 5, 6, 7, 8, 9, 10, 11, or 12 hours apart. In embodiments the first and second pharmaceutical composition may be administered 12 hours apart. In embodiments, the first and second pharmaceutical compositions may administered within, e.g., 15 minutes, 30 minutes, 1 hour, 2 hours, 6 hours, 12 hours, 18 hours, 24 hours, etc. In embodiments, the first and second pharmaceutical compositions may administered separated by at least, e.g., 15 minutes, 30 minutes, 1 hour, 2 hours, 12 hours, 18 hours, 24 hours, etc. In embodiments, improvement in at least one symptom of Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome for more than 8 hours after administration to the subject is provided. In embodiments, improvement for more than about, e.g., 10 hours, 12 hours, 15 hours, 18 hours, 20 hours, 24 hours, 30 hours, 36 hours, 42 hours or 48 hours after administration to the subject is provided.

In embodiments, the administration of the first and second pharmaceutical composition may provide a synergistic effect to improve at least one symptom of Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome.

In embodiments, provided herein are methods of treating Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome which include administering to a subject in need thereof a first pharmaceutical dosage including a sub-therapeutic amount of one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding. In embodiments, treating Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome includes administering to a subject in need thereof a first pharmaceutical dosage including a sub-therapeutic amount of one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, wherein the composition provides improvement in one or more symptoms of the disorder for more than 6 hours after administration.

In embodiments, the first and/or the second pharmaceutical compositions contain sub-therapeutic dosages. A sub-therapeutic dosage is an amount of active substance, e.g., one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, that is less than the amount typically required for a therapeutic effect. In embodiments, a sub-therapeutic dosage is an amount of one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, that alone may not provide improvement in at least one symptom of Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome, but is sufficient to maintain such improvement. In embodiments, the methods provide administering a first pharmaceutical composition that provides improvement in at least one symptom of Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome, and a second composition that maintains the improvement. In embodiments, the second composition contains a sub-therapeutic dose of one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding. In embodiments, after administration of the first pharmaceutical composition, the second pharmaceutical composition may provide a synergistic effect to improve at least one symptom of Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome. In embodiments, the second pharmaceutical composition may provide a synergistic effect to improve at least one symptom of Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome.

In embodiments, provided herein are methods of treating Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome which include administering to a subject in need thereof a first pharmaceutical composition including a first pharmaceutical dosage of, e.g., one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, wherein the first pharmaceutical dosage provides improvement for more than 6 hours after administration, and a second pharmaceutical composition including a sub-therapeutic dosage of one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding.

In embodiments, the first or the second pharmaceutical composition are provided to the subject once in the evening and once in the morning. In embodiments, the total amount of one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, administered to a subject in a 24-hour period is any of the respective amounts described herein.

In embodiments, the first and/or the second pharmaceutical compositions may be provided with conventional release or modified release profiles. The first and second pharmaceutical compositions may be provided at the same time or separated by an interval of time, e.g., 1 hour, 2 hours, 3 hours, 4 hours, 5 hours, 6 hours, 12 hours, etc. In embodiments, the first and the second pharmaceutical compositions may be provided with different drug release profiles to create a two-phase release profile. For example, the first pharmaceutical composition may be provided with an immediate release profile, e.g., ODDF, parenteral, etc., and the second pharmaceutical composition may provide an extended release profile. In embodiments, one or both of the first and second pharmaceutical compositions may be provided with an extended release or delayed release profile. Such compositions may be provided as pulsatile formulations, multilayer tablets or capsules containing tablets, beads, granules, etc. In embodiments, the first pharmaceutical composition is an immediate release composition. In embodiments, the second pharmaceutical composition is an immediate release composition. In embodiments, the first and second pharmaceutical compositions are provided as separate immediate release compositions, e.g., film, tablets or capsules. In embodiments the first and second pharmaceutical compositions are provided 12 hours apart.

It should be understood that respective dosage amounts of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, that are provided herein are applicable to all the dosage forms described herein including conventional dosage forms, modified dosage forms, the first and second pharmaceutical compositions, as well as the parenteral formulations described herein. Those skilled in the art will determine appropriate amounts depending on criteria such as dosage form, route of administration, subject tolerance, efficacy, therapeutic goal and therapeutic benefit, among other pharmaceutically acceptable criteria.

Combination therapies utilizing one or more a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, can include administration of the active agents together in the same admixture, or in separate admixtures. In embodiments, the pharmaceutical composition can includes two, three, or more active agents. In embodiments, the combinations result in a more than additive effect on the treatment of the disease or disorder. Thus, treatment is provided for Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome with a combination of agents that, as combined, may provide a synergistic effect that enhances efficacy.

In embodiments, a co-therapy of a compound of Formula 1, (1S,3S)-3-amino-4-(difluoromethylidene)cyclopentane-1-carboxylic acid, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, is effective to reduce frequency or severity of symptoms in the subject greater than any of the compounds administered alone. In embodiments, the co-therapy produces a more than additive result compared to compounds administered individually.

In embodiments, the subject may be started at a low dose and the dosage is escalated. In this manner, it can be determined if the drug is well tolerated in the subject. Dosages can be lower for children than for adults.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of Angelman syndrome, Fragile X syndrome, and Fragile X-associated tremor/ataxia syndrome, Autism Spectrum Disorder, Asperger's syndrome, pervasive developmental disorder not otherwise characterized, Childhood Disintegrative Disorder, Williams syndrome, or Jacobsen syndrome, measured relative to at least one symptom of the foregoing disorders.

"Improvement in next day functioning" or "wherein there is improvement in next day functioning" refers to improvement after waking from an overnight sleep period wherein the beneficial effect of administration of (1S,3S)-3-amino-4-(difluoromethylidene)cyclopentane-1-carboxylic acid, a compound of Formula 1, (S)-3-amino-4-(difluoromethylenyl)cyclopent-1-ene-1-carboxylic acid, or vigabatrin ((RS)-4-aminohex-5-enoic acid), or a pharmaceutically acceptable salt of any of the preceding, applies to at least one symptom of a syndrome or disorder herein and is discernable, either subjectively by a subject or objectively by an observer, for a period of time, e.g., 2 hours, 3 hours, 4 hours, 5 hours, 6 hours, 12 hours, 24 hours, etc. after waking.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml or µg·hr/ml). The area under the curve is governed by clearance. Clearance is defined as the volume of blood or plasma that is totally cleared of its content of drug per unit time (ml/min).

"Treating", "treatment" or "treat" can refer to the following: alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating", "treat" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating", "treat" or "treatment" also refers to inhibiting the disease or condition, e.g., arresting or reducing its development or at least one clinical or subclinical symptom thereof. "Treating", "treat" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Pharmaceutically acceptable" refers to molecular entities and compositions that are "generally regarded as safe", e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount", previously referred to, can also mean a dosage sufficient to alleviate one or more symptoms of a syndrome, disorder, disease, or condition being treated, or to otherwise provide a desired pharmacological and/or physiologic effect. "Effective amount" or "therapeutically effective amount" may be used interchangeably herein.

"Co-administered with", "administered in combination with", "a combination of" or "administered along with" may be used interchangeably and mean that two or more agents are administered in the course of therapy. The agents may be administered together at the same time or separately in spaced apart intervals. The agents may be administered in a single dosage form or in separate dosage forms.

"Subject in need thereof" may include individuals that have been diagnosed with Angelman syndrome, Fragile X syndrome, and Fragile X-associated tremor/ataxia syndrome, Autism Spectrum Disorder, Asperger's syndrome, Pervasive developmental disorder not otherwise characterized, Childhood Disintegrative Disorder, Williams syndrome, or Jacobsen syndrome. The methods may be provided to any individual including, e.g., wherein the subject is a neonate, infant, a pediatric subject (6 months to 12 years), an adolescent subject (age 12-18 years) or an adult (over 18 years). Subjects include mammals. "Patient" and "subject" may be used interchangeably herein.

"Prodrug" refers to a pharmacological substance (drug) that is administered to a subject in an inactive (or significantly less active) form. Once administered, the prodrug is metabolized in the body (in vivo) into a compound having the desired pharmacological activity.

"Analog" and "Derivative" may be used interchangeably and refer to a compound that possesses the same core as the parent compound, but may differ from the parent compound in bond order, the absence or presence of one or more atoms and/or groups of atoms, and combinations thereof. The derivative can differ from the parent compound, for example, in one or more substituents present on the core, which may include one or more atoms, functional groups, or substructures. In general, a derivative can be imagined to be formed, at least theoretically, from the parent compound via chemical and/or physical processes.

The term "pharmaceutically acceptable salt", as used herein, refers to derivatives of the compounds defined herein, wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include but are not limited to those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts. The pharmaceutically acceptable salts can be synthesized from the parent compound, which contains a basic or acidic moiety, by conventional chemical methods.

EXAMPLES

The examples provided herein are included solely for augmenting the disclosure herein and should not be considered to be limiting in any respect.

Effect of (S)-3-Amino-4-(difluoromethylenyl)cyclopent-1-ene-1-carboxylic acid on Fmr1 Knock-Out Mice Mutant fmr1 knockout (KO) mice recapitulate the Fragile X syndrome (FXS) phenotype and represent a preclinical model for assessment of putative drug treatments. In this study three different mice models of FXS were used: Fmr1 KO1 is the original Fmr1 knockout animal that carries an insertion in exon 5. See, e.g., Bakker C E, et al., The Dutch-Belgian Fragile X Consortium, Fmr1 knockout mice: A model to study fragile X mental retardation. Cell. 1994; 78:23-33 It is a protein null, although Fmr1 mRNA is still present. It is backcrossed to the C57/Bl6 strain. Subsequently, these mice were bred into different background strains, such as the FVB inbred mouse strain. Fmr1 KO2 is a null allele at Fmr1 generated by deletion of the promoter and first exon of Fmr1. See, Mientjes, E J et al., The generation of a conditional Fmr1 knock out mouse model to study Fmrp function in vivo. Neurobiology of Disease (2006) 21(3): 549-555. It is both protein and mRNA null. Backcrossed to the C57/Bl6 strain. Genotyping was accomplished using TransnetXY Automated Genotyping (http://www.transnetyx.com/). TRANSNETYX, INC., 8110 Cordova Rd. Suite 119, Cordova, Tenn. 38016, USA.

The mice were housed in plastic cages (35×30×12 cm), 5 in each and habituated to the animal facilities for at least a week before test. The room temperature (21±2° C.), relative humidity (55±5%), a 12-h light-dark cycle (lights on 7 a.m.-7 p.m.) and air exchange (16 times per h) were automatically controlled. The animals had free access to commercial food pellets and water. Testing was conducted during the light phase. Testing was conducted on Fmr1 knockout mice and their wild-type (WT) littermates. Ten mice per treatment group, 14 weeks of age, were used for behavioral experiments. Experiments were conducted in line with the requirements of the UK Animals (Scientific Procedures) Act, 1986.

Oral dosing was performed by using 1.5-in. curved, 20-gauge, stainless steel feeding needles with a 2.25-mm ball (Braintree Scientific, Braintree, Mass.). Each gavage treatment was given in 0.5% methyl cellulose (Methyl Cellulose M0512, Sigma-Aldrich, St Louis, Mo.) used as vehicle with or without treatment compounds. The same veterinarian, blinded to the treatment groups, performed the procedure, and documented animal reactions to oral gavage. Reactions considered to indicate stress were defined as excessive struggling during gavage or abnormal behavior after gavage (labored breathing, frozen stance, exaggerated jumping, shuddering, and hunched posture). If mice demonstrated any of these signs during gavage itself or the 10 seconds immediately after the procedure, the procedure was scored as a stressful event, and the animal removed from the study.

For experiments all mice were tested once in the same apparatus. Prior to testing, mice not in the study were placed in the apparatus for some minutes before the experiment. The apparatus was then cleaned with moist and dry tissues before testing each mouse. The aim was to create a low but constant background mouse odor for all experimental subjects. All experiments were conducted with the experimenters blind to genotype and drug treatment during all testing and data analysis. Separate investigators prepared and coded dosing solutions, allocated the mice to the study treatment groups, dosed the animals, and collected the behavioral data. Data were analyzed by one-way analysis of variance (ANOVA) followed by post-hoc comparisons where appropriate using Tukey's Multiple Comparison Test. Data are represented as the mean and standard error of the mean (SEM).

Aim 1:

Dosing protocol in the Fmr1 KO2 mouse is provided in Table 1. (S)-3-Amino-4-(difluoromethylenyl)cyclopent-1-ene-1-carboxylic acid is referred to as "compound" in Table 1. "QD" is once daily.

TABLE 1

| Group no. | Group | Dosing route | Dosing | n |
|---|---|---|---|---|
| 1a | WT-Veh | PO (0.5% Methylcellulose at 5 mL/kg) | QD for seven days prior to testing | 10 |
| 1b | KO2-Veh | PO (0.5% Methylcellulose at 5 mL/kg) | QD for seven days prior to testing | 10 |
| 1c | KO2-Compound (0.01 mg/kg) | PO (0.5% Methylcellulose at 5 mL/kg) | QD for seven days prior to testing | 10 |

TABLE 1-continued

| Group no. | Group | Dosing route | Dosing | n |
|---|---|---|---|---|
| 1d | KO2-Compound (0.05 mg/kg) | PO (0.5% Methylcellulose at 5 mL/kg) | QD for seven days prior to testing | 10 |
| 1e | KO2-Compound (0.1 mg/kg) | PO (0.5% Methylcellulose at 5 mL/kg) | QD for seven days prior to testing | 10 |

Test Criteria:
 1. Open Field (hyperactivity)
 2. Open Field Repetitive Behaviors (stereotypies: anticlockwise circling and self-grooming)
 3. Tests of daily living (nesting)
 4. Hyponeophagia (anxiety)

Results:
 1. Open field hyperactivity is demonstrated by locomotor activity in the open field. FIG. 1 is a bar graph illustrating open field locomotor activity (total distance traveled) of wild-type mice administered 0.5% methyl cellulose vehicle, Fmr1 KO2 mice administered 0.5% methyl cellulose vehicle, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

ANOVA summary: F-32.09, P value-<0.0001, P value summary ****, significant difference among means (P<0.05)—yes, R square-0.732. Multiple comparisons test are provided in Table 2.

TABLE 2

| Multiple comparisons test | Significant? | Summary | Adjusted P Value |
|---|---|---|---|
| WT-Veh vs. KO2-Veh | Yes | **** | 0.0001 |
| WT-Veh vs. KO2-Compound 0.01 mg/Kg | Yes | **** | 0.0001 |
| WT-Veh vs. KO2-Compound 0.05 mg/Kg | Yes | * | 0.0174 |
| WT-Veh vs. KO2-Compound 0.1 mg/Kg | No | ns | 0.6927 |

As can be seen from FIG. 1, Fmr1 KO2 animals were more active than WT littermates in the open field (p<0.0001) and this hyperactivity was significantly reduced by (S)-3-amino-4-(difluoromethylenyl)cyclopent-1-ene-1-carboxylic acid treatment at 0.1 mg/Kg.

2. Open Field Repetitive Behaviors (stereotypies: anticlockwise circling (aka counter revolutions) (CCW) and self grooming). niFmr KO2 mice display the autism-like phenotypes of repetitive behaviors like CCW, self grooming and stereotypy that typically involves behaviors such as head bobbing.

Figure 2:
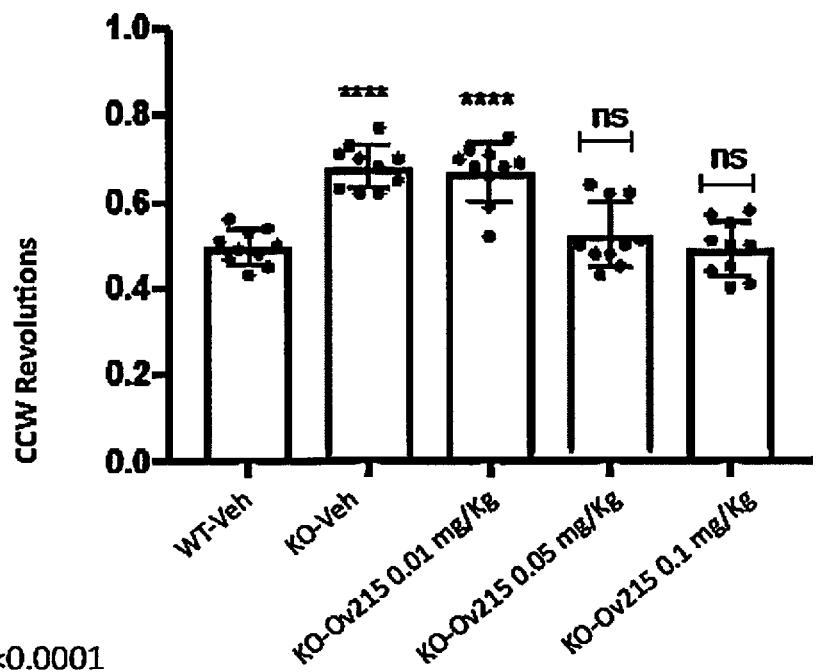
FIG. 2 is a bar graph illustrating open field counter revolutions (CCW) of wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

A. CCW: FIG. 2 is a bar graph illustrating open field counter revolutions of wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

ANOVA summary: F-24.34, P value-<0.0001, P value summary ****, significant difference among means (P<0.05)—yes, R square-0.6839. CCW multiple comparisons test are provided in Table 3.

TABLE 3

| Multiple comparisons test | Significant? | Summary | Adjusted P Value |
|---|---|---|---|
| WT-Veh vs. KO2-Veh | Yes | **** | 0.0001 |
| WT-Veh vs. KO2-Compound 0.01 mg/Kg | Yes | **** | 0.0001 |
| WT-Veh vs. KO2-Compound 0.05 mg/Kg | No | ns | 0.7956 |
| WT-Veh vs. KO2-Compound 0.1 mg/Kg | No | ns | 0.9996 |

As can be seen from FIG. 2, Fmr1 KO2+vehicle revolved in the CCW direction significantly more than WT+vehicle (p<0.0001). This phenotype was rescued by (S)-3-amino-4-(difluoromethylenyl) cyclopent-1-ene-1-carboxylic acid at 0.05 and 0.1 mg/Kg, because CCW revolutions were significantly lower than in Fmr1 KO2+vehicle but similar to CCW revolutions in WT+vehicle.

Figure 3:
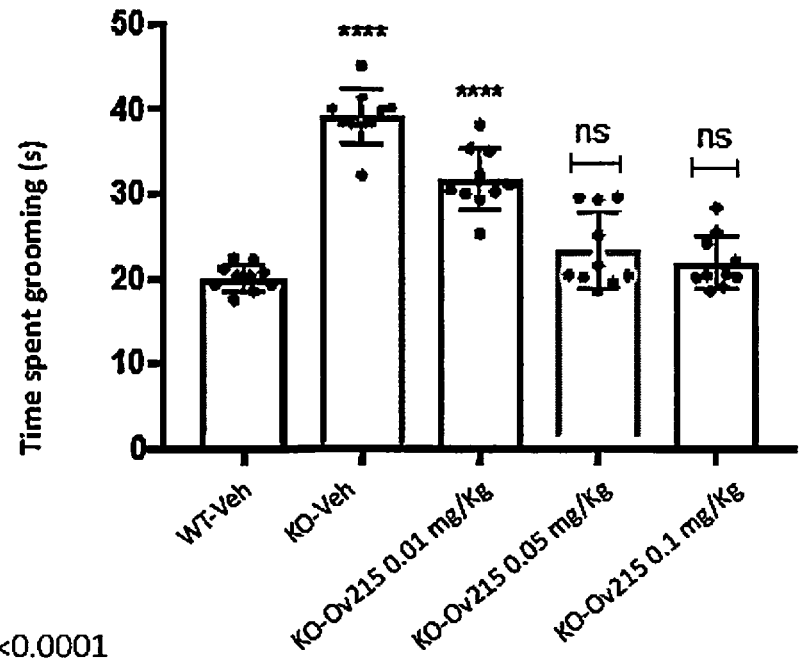
FIG. 3 is a bar graph illustrating time spent grooming by wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

B. Self grooming: FIG. 3 is a bar graph illustrating time spent grooming by wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg. ANOVA summary: F-56.67, P value-<0.0001, P value summary ****, significant difference among means (P<0.05)—yes, R square-0.8344. CCW multiple comparisons test are provided in Table 4.

TABLE 4

| Multiple comparisons test | Significant? | Summary | Adjusted P Value |
|---|---|---|---|
| WT-Veh vs. KO2-Veh | Yes | **** | 0.0001 |
| WT-Veh vs. KO2-Compound 0.01 mg/Kg | Yes | **** | 0.0001 |
| WT-Veh vs. KO2-Compound 0.05 mg/Kg | No | ns | 0.1434 |
| WT-Veh vs. KO2-Compound 0.1 mg/Kg | No | ns | 0.7018 |

As can be seen from FIG. 3, Fmr1 KO2 mice exhibit abnormal self grooming. Fmr1 KO2+vehicle self groomed significantly more than WT+vehicle (p<0.0001). This phenotype was rescued by S)-3-amino-4-(difluoromethylenyl) cyclopent-1-ene-1-carboxylic acid at 0.05 and 0.1 mg/Kg.

Figure 4:
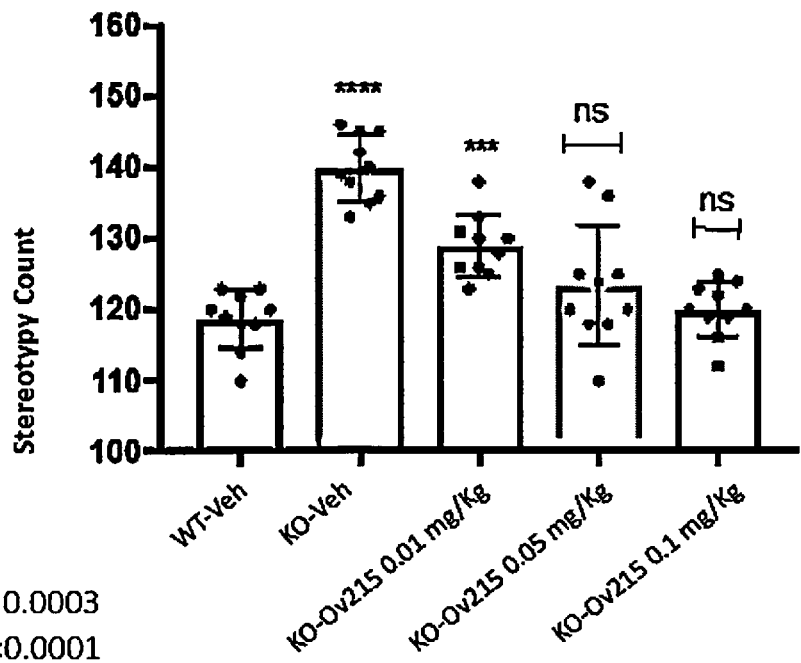
FIG. 4 is a bar graph illustrating stereotypy count by wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

C. Stereotypy: FIG. 4 is a bar graph illustrating stereotypy count by wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg. ANOVA summary: F-26.13, P value-<0.0001, P value summary ****, significant difference among means (P<0.05)—yes, R square-0.699. Sterotypy count multiple comparisons test are provided in Table 5.

TABLE 5

| Multiple comparisons test | Significant? | Summary | Adjusted P Value |
|---|---|---|---|
| WT-Veh vs. KO2-Veh | Yes | **** | 0.0001 |
| WT-Veh vs. KO2-Compound 0.01 mg/Kg | Yes | *** | 0.0001 |
| WT-Veh vs. KO2-Compound 0.05 mg/Kg | No | ns | 0.1679 |
| WT-Veh vs. KO2-Compound 0.1 mg/Kg | No | ns | 0.9520 |

As can be seen from FIG. 4, Fmr1 KO2+vehicle exhibited higher levels of stereotypy counts compared with WT+veh, and this phenotype was reversed by S)-3-amino-4-(difluoromethylenyl) cyclopent-1-ene-1-carboxylic acid at 0.05 and 0.1 mg/Kg.

Figure 5:
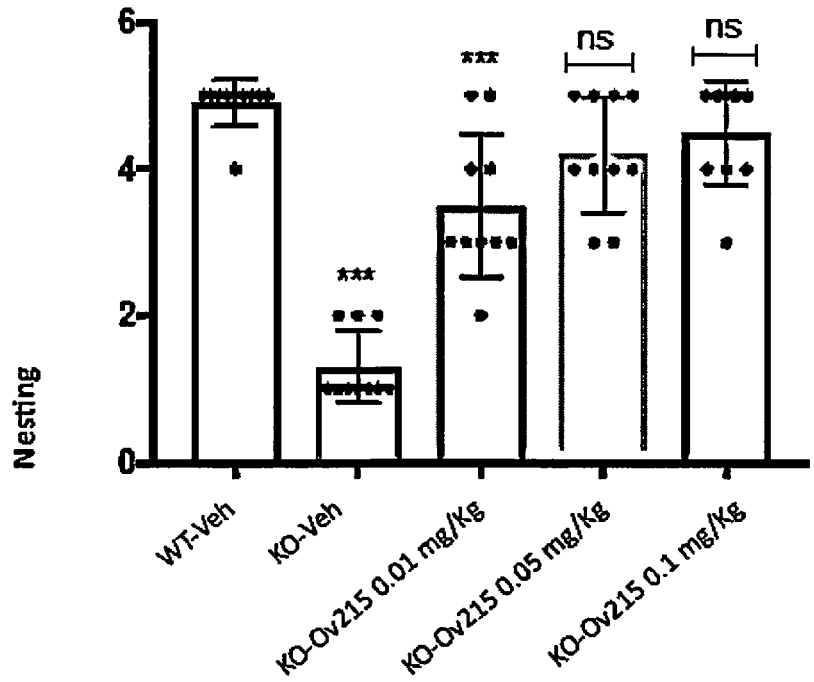
FIG. 5 is a bar graph illustrating nesting behavior by wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

3. Tests of daily living (nesting). Species-typical behaviors offer easy ways to test for hippocampal dysfunction. The hippocampus is vital for the performance of species-typical tasks, or "activities of daily living" of mice. FIG. 5 is a bar graph illustrating nesting behavior by wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

ANOVA summary: F-42.33, P value-<0.0001, P value summary ****, significant difference among means (P<0.05)—yes, R square-0.79. Nesting multiple comparisons test are provided in Table 6.

TABLE 6

| Multiple comparisons test | Significant? | Summary | Adjusted P Value |
|---|---|---|---|
| WT-Veh vs. KO2-Veh | Yes | **** | 0.0001 |
| WT-Veh vs. KO2-Compound 0.01 mg/Kg | Yes | *** | 0.0001 |
| WT-Veh vs. KO2-Compound 0.05 mg/Kg | No | ns | 0.0924 |
| WT-Veh vs. KO2-Compound 0.1 mg/Kg | No | ns | 0.5110 |

As can be seen from FIG. 5, Fmr1 KO2 mice showed poorer nest building than WT littermates. This phenotype was rescued by (S)-3-amino-4-(difluoromethylenyl) cyclopent-1-ene-1-carboxylic acid at 0.05 and 0.1 mg/Kg.

Figure 6:
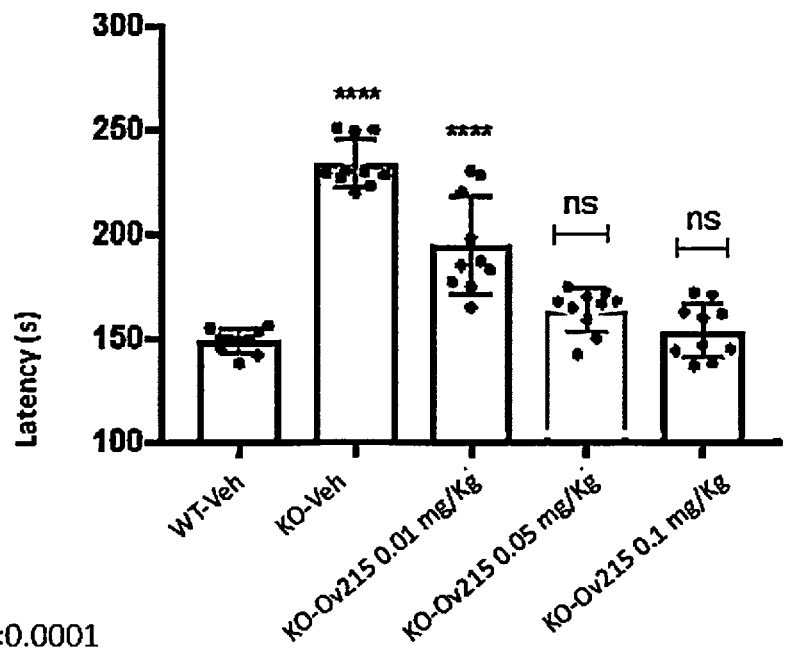
FIG. 6 is a bar graph latency to eat behavior (novel food in a novel environment) by wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg.

4. Hyponeophagia (inhibition of feeding) is used as a measure of anxiety which can be produced by a novel environment, particularly in rodents. FIG. 6 is a bar graph latency to eat behavior (novel food in a novel environment) by wild-type mice administered 0.5% methyl cellulose vehicle, Fmr1 KO2 mice administered 0.5% methyl cellulose, Fmr1 KO2 mice administered (S)-3-amino-4-(difluoromethylenyl) cyclopent-1-ene-1-carboxylic acid 0.01 mg/kg, Fmr1 KO2 mice administered (S)-3-amino-4-(difluoromethylenyl) cyclopent-1-ene-1-carboxylic acid 0.05 mg/kg, and Fmr1 KO2 mice administered (S)-3-amino-4-(difluoromethylenyl) cyclopent-1-ene-1-carboxylic acid 0.1 mg/kg. ANOVA summary: F-63.24, P value-<0.0001, P value summary ****, significant difference among means (P<0.05)—yes, R square-0.79. Hyponeophagia multiple comparisons test are provided in Table 7.

TABLE 7

| Multiple comparisons test | Significant? | Summary | Adjusted P Value |
|---|---|---|---|
| WT-Veh vs. KO2-Veh | Yes | **** | 0.0001 |
| WT-Veh vs. KO2-Compound 0.01 mg/Kg | Yes | **** | 0.0001 |
| WT-Veh vs. KO2-Compound 0.05 mg/Kg | No | ns | 0.0759 |
| WT-Veh vs. KO2-Compound 0.1 mg/Kg | No | ns | 0.8342 |

In the hyponeophagia test, which assesses a specific type of anxiety—eating a novel food in a novel environmental context and as can be seen from FIG. 6, Fmr1 KO2 mice showed a significantly higher latency to eat than WT controls, indicating that they were much more anxious. (S)-3-amino-4-(difluoromethylenyl) cyclopent-1-ene-1-carboxylic acid at 0.05 and 0.1 mg/Kg had a strong effect in Fmr1 KO2 decreasing their latency to eat to virtually control levels. Thus, (S)-3-amino-4-(difluoromethylenyl) cyclopent-1-ene-1-carboxylic acid showed strong restorative effects in this preclinical model of FX syndrome.

Aim 2:

Dosing protocol in the Fmr1 KO1 mouse (C57/B6 background) is provided in Table 8. (S)-3-Amino-4-(difluoromethylenyl)cyclopent-1-ene-1-carboxylic acid is referred to as "compound" in Table 8. "QD" is once daily.

TABLE 8

| Group no. | Group | Dosing route | Dosing | n |
|---|---|---|---|---|
| 2a | WT-Veh | PO (0.5% Methylcellulose at 5 mL/kg) | QD for seven days prior to testing | 10 |
| 2b | KO1-Veh | PO (0.5% Methylcellulose at 5 mL/kg) | QD for seven days prior to testing | 10 |
| 2c | KO1-Compound (0.01 mg/kg) | PO (0.5% Methylcellulose at 5 mL/kg) | QD for seven days prior to testing | 10 |
| 2d | KO1-Compound (0.05 mg/kg) | PO (0.5% Methylcellulose at 5 mL/kg) | QD for seven days prior to testing | 10 |
| 2e | KO1-Compound (0.1 mg/kg) | PO (0.5% Methylcellulose at 5 mL/kg) | QD for seven days prior to testing | 10 |

Figure 7:
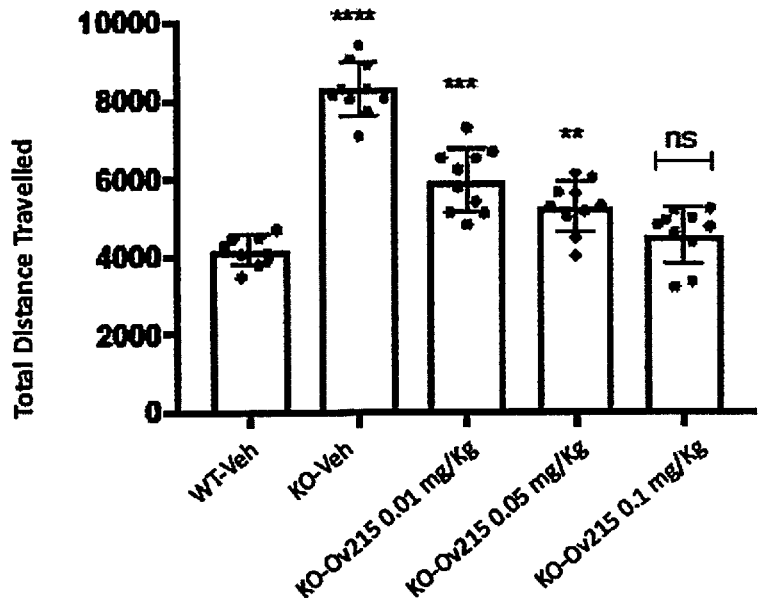
FIG. 7 is a bar graph illustrating open field locomotive activity (total distance traveled) of wild-type mice administered 0.5% methyl cellulose vehicle, Fmr1 KO1 mice administered 0.5% methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

Test Criteria:
1. Open Field (hyperactivity)
2. Open Field Repetitive Behaviors (stereotypies: anti-clockwise circling and self-grooming)
3. Tests of daily living (nesting)
4. Audiogenic Seizures Results:
1. Open field hyperactivity is demonstrated by locomotor activity in the open field. FIG. 7 is a bar graph illustrating open field locomotive activity (total distance traveled) of wild-type mice administered 0.5% methyl cellulose vehicle, Fmr1 KO1 mice administered 0.5%0 methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

ANOVA summary: F-59.86, P value-<0.0001, P value summary ****, significant difference among means (P<0.05)—yes, R square-0.8418. Open field (hyperactivity) multiple comparisons test are provided in Table 9.

TABLE 9

| Multiple comparisons test | Significant? | Summary | Adjusted P Value |
|---|---|---|---|
| WT-Veh vs. KO1-Veh | Yes | **** | 0.0001 |
| WT-Veh vs. KO1-Compound 0.01 mg/Kg | Yes | **** | 0.0001 |
| WT-Veh vs. KO1-Compound 0.05 mg/Kg | Yes | ** | 0.0027 |
| WT-Veh vs. KO1-Compound 0.1 mg/Kg | No | ns | 0.5878 |

As can be seen from FIG. 7, at 0.1 mg/Kg (S)-3-amino-4-(difluoromethylenyl)cyclopent-1-ene-1-carboxylic acid reversed hyperactivity in Fmr1 KO1 mice. Fmr1 KO1 mice were more active in the open-field test than were WT littermates. However, this increase in motor activity was reversed by treatment with (S)-3-Amino-4-(difluoromethylenyl)cyclopent-1-ene-1-carboxylic acid; these values were not significantly different than WT+veh.

2. Open Field Repetitive Behaviors (RB) (stereotypies: anticlockwise circling and self grooming). Fmr1 KO1 mice display the autism-like phenotypes of repetitive behaviors like counter revolutions (CCW), self grooming and stereotypy that typically involves behaviors such as head bobbing.

Figure 8:
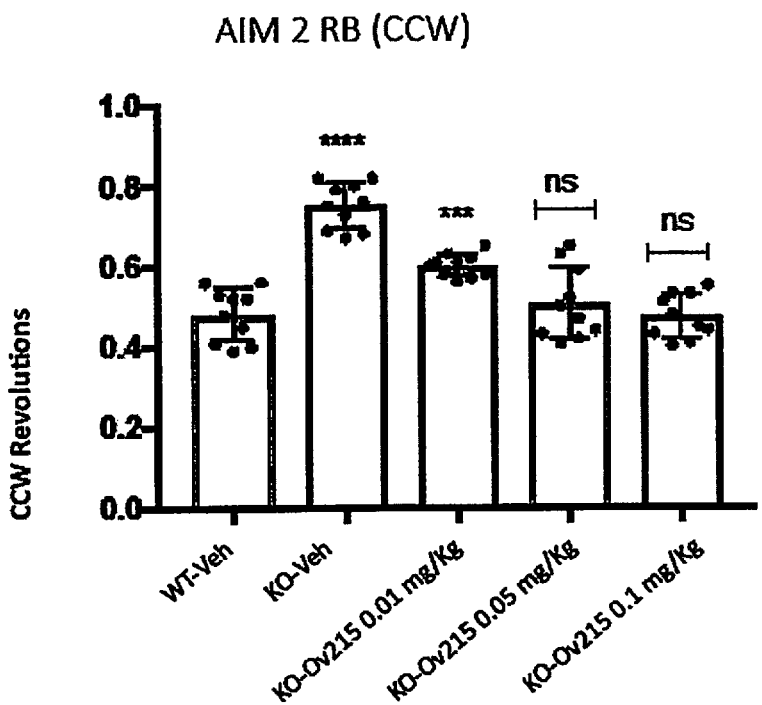
FIG. 8 is a bar graph illustrating open field counter revolutions (CCW) of wild-type mice administered 0.5% methyl cellulose vehicle, Fmr1 KO1 mice administered 0.5% methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

A. CCW: FIG. 8 is a bar graph illustrating open field counter revolutions of wild-type mice administered 0.5% methyl cellulose vehicle, Fmr1 KO1 mice administered 0.5% methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

ANOVA summary: F-35.49, P value-<0.0001, P value summary ****, significant difference among means (P<0.05)—yes, R square-0.7593. CCW multiple comparisons test are provided in Table 10.

TABLE 10

| Multiple comparisons test | Significant? | Summary | Adjusted P Value |
|---|---|---|---|
| WT-Veh vs. KO1-Veh | Yes | **** | 0.0001 |
| WT-Veh vs. KO1-Compound 0.01 mg/Kg | Yes | *** | 0.0004 |
| WT-Veh vs. KO1-Compound 0.05 mg/Kg | No | ns | 0.8012 |
| WT-Veh vs. KO1-Compound 0.1 mg/Kg | No | ns | 0.9927 |

As can be seen from FIG. 8, Fmr1 KO1+veh made more counterclockwise revolutions than WT+veh. (S)-3-amino-4-(difluoromethylenyl) cyclopent-1-ene-1-carboxylic acid reversed CCW repetitive behavior in Fmr1 KO1 mice at 0.05 and 0.1 mg/Kg. Fmr1 KO+(S)-3-amino-4-(difluoromethylenyl) cyclopent-1-ene-1-carboxylic acid did not differ from WT+veh.

Figure 9:
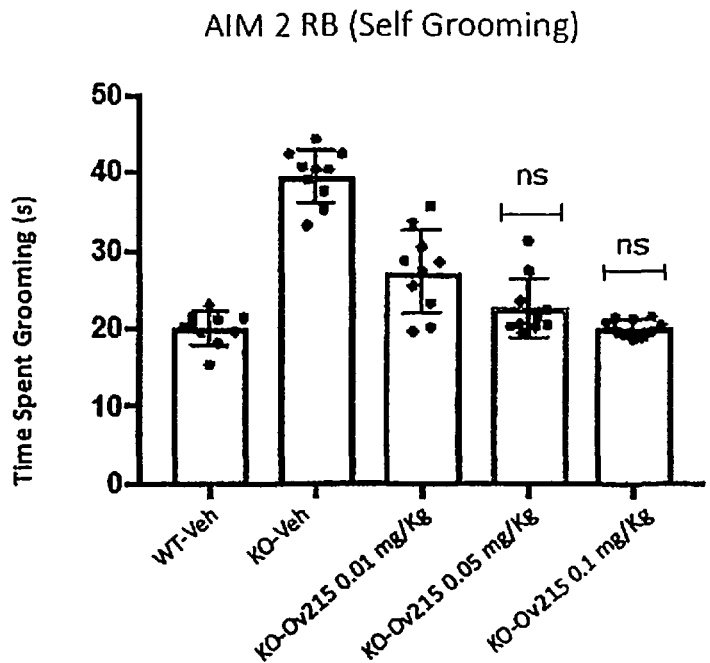
FIG. 9 is a bar graph illustrating time spent grooming by wild-type mice administered 0.5% methyl cellulose vehicle, Fmr1 KO1 mice administered 0.5% methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

B. Self grooming: FIG. 9 is a bar graph illustrating time spent grooming by wild-type mice administered 0.5% methyl cellulose vehicle, Fmr1 KO1 mice administered 0.5%0 methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

ANOVA summary: F-55.31, P value-<0.0001, P value summary ****, significant difference among means (P<0.05)—yes, R square-0.831. Self grooming multiple comparisons test are provided in Table 11.

TABLE 11

| Multiple comparisons test | Significant? | Summary | Adjusted P Value |
|---|---|---|---|
| WT-Veh vs. KO1-Veh | Yes | **** | 0.0001 |
| WT-Veh vs. KO1-Compound 0.01 mg/Kg | Yes | *** | 0.0001 |
| WT-Veh vs. KO1-Compound 0.05 mg/Kg | No | ns | 0.2624 |
| WT-Veh vs. KO1-Compound 0.1 mg/Kg | No | ns | 0.9999 |

As can be seen from FIG. 9, Fmr1 KO1+veh spent more time self-grooming than WT+veh and (S)-3-amino-4-(difluoromethylenyl) cyclopent-1-ene-1-carboxylic acid treated Fmr1 KO1 at 0.05 and 0.1 mg/Kg. Fmr1 KO1+(S)-3-amino-4-(difluoromethylenyl) cyclopent-1-ene-1-carboxylic acid did not differ from WT+veh.

Figure 10:
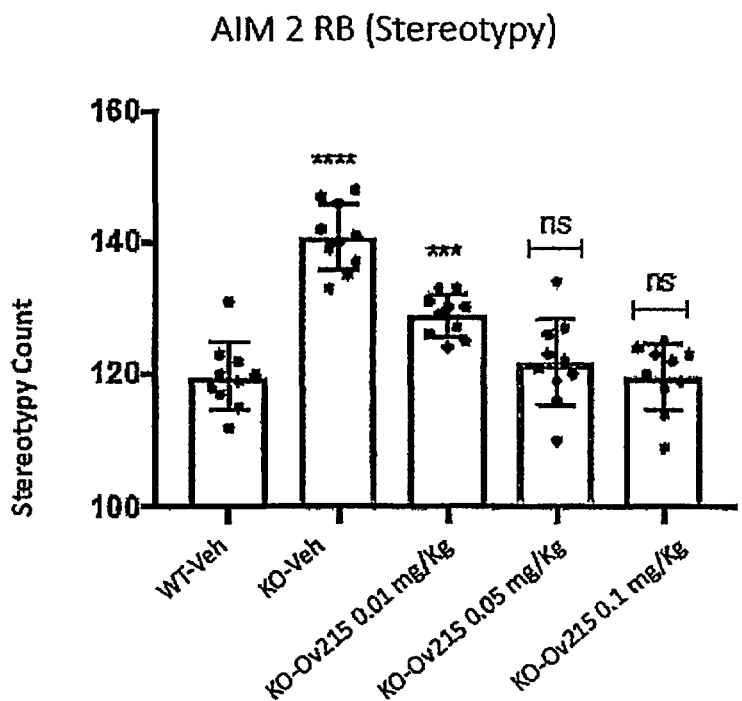
FIG. 10 is a bar graph illustrating stereotypy count by wild-type mice administered 0.5% methyl cellulose vehicle, Fmr1 KO1 mice administered 0.5% methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

C. Stereotypy: FIG. 10 is a bar graph illustrating stereotypy count by wild-type mice administered 0.5% methyl cellulose vehicle, Fmr1 KO1 mice administered 0.5% methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

ANOVA summary: F-31.32, P value-<0.0001, P value summary ****, significant difference among means (P<0.05)—yes, R square-0.7357. Sterotypy count multiple comparisons test are provided in Table 12.

TABLE 12

| Multiple comparisons test | Significant? | Summary | Adjusted P Value |
|---|---|---|---|
| WT-Veh vs. KO1-Veh | Yes | **** | 0.0001 |
| WT-Veh vs. KO1-Compound 0.01 mg/Kg | Yes | *** | 0.0009 |
| WT-Veh vs. KO1-Compound 0.05 mg/Kg | No | ns | 0.7637 |
| WT-Veh vs. KO1-Compound 0.1 mg/Kg | No | ns | 0.9999 |

As can be seen from FIG. 10, Fmr1 KO1+veh made more stereotypical movements than WT+veh. Repetitive behaviors were decreased by S)-3-amino-4-(difluoromethylenyl) cyclopent-1-ene-1-carboxylic acid treatment at 0.05 and 0.1 mg/Kg.

Figure 11:
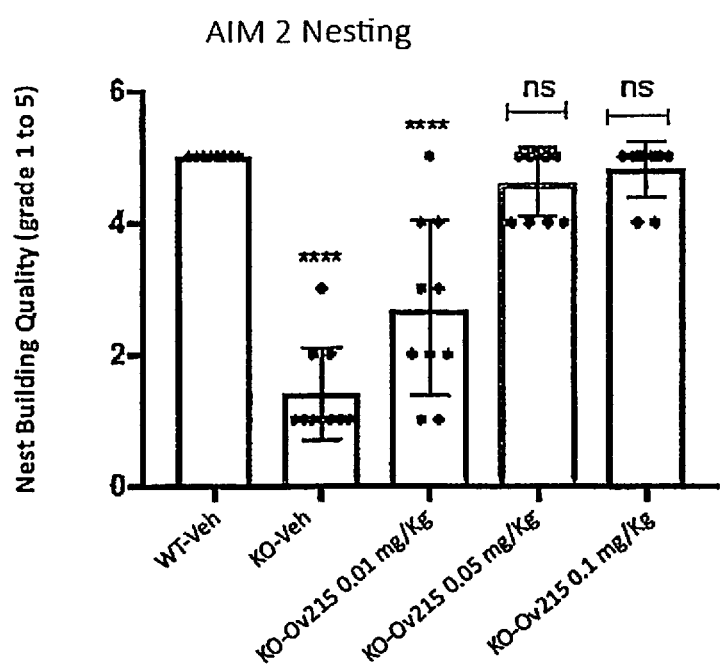
FIG. 11 is a bar graph illustrating nest building quality by wild-type mice administered 0.5% methyl cellulose vehicle, Fmr1 KO1 mice administered 0.5% methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

3. Tests of daily living (Nesting): FIG. 11 is a bar graph illustrating nest building quality by wild-type mice administered 0.50% methyl cellulose vehicle, Fmr1 KO1 mice administered 0.5%0 methyl cellulose, Fmr1 KO1 mice administered (S)-3-amino-4-(difluoromethylenyl) cyclopent-1-ene-1-carboxylic acid 0.01 mg/kg, Fmr1 KO1 mice administered (S)-3-amino-4-(difluoromethylenyl) cyclopent-1-ene-1-carboxylic acid 0.05 mg/kg, and Fmr1 KO1 mice administered (S)-3-amino-4-(difluoromethylenyl) cyclopent-1-ene-1-carboxylic acid 0.1 mg/kg.

ANOVA summary: F-45.92, P value-<0.0001, P value summary ****, significant difference among means (P<0.05)—yes, R square-0.8032. Nesting multiple comparisons test are provided in Table 13.

TABLE 13

| Multiple comparisons test | Significant? | Summary | Adjusted P Value |
|---|---|---|---|
| WT-Veh vs. KO1-Veh | Yes | **** | 0.0001 |
| WT-Veh vs. KO1-Compound 0.01 mg/Kg | Yes | *** | 0.0001 |
| WT-Veh vs. KO1-Compound 0.05 mg/Kg | No | ns | 0.5648 |
| WT-Veh vs. KO1-Compound 0.1 mg/Kg | No | ns | 0.9313 |

As can be seen from FIG. 11, Fmr1 KO1 mice build nests of poorer quality than WT littermates. (S)-3-amino-4-(difluoromethylenyl) cyclopent-1-ene-1-carboxylic acid rescues poor nesting behavior at 0.05 and 0.1 mg/Kg. Poor nesting behavior is associated with the medial prefrontal cortex, ventral tegmental area and hippocampus of the mice.

4. Audiogenic Seizures (AGS) are reflex seizures generated by loud noises in genetically predisposed mice. The Fmr1 KO1 mice display audiogenic seizures depending on age and background strain, the Fmr1 KO1 mouse on the FVB background is characterized by an increased AGS susceptibility at all ages and is considered a good animal model for epilepsy. The effect of (S)-3-amino-4-(difluoromethylenyl) cyclopent-1-ene-1-carboxylic acid was tested on AGS Fmr1 KO1 transgenic mice in an FVB background. Observable criteria are: 1. normal behavior, 2. wild running, 3. seizure, and 4. respiratory arrest.

(S)-3-amino-4-(difluoromethylenyl) cyclopent-1-ene-1-carboxylic acid was administered to Fmr1 KO1 mice, males, age 2 months in the following amounts: 0.01 mg/kg, 0.05 mg/kg, and 0.1 mg/kg. Positive controls were administered 2-Methyl-6-(phenylethynyl)pyridine (MPEP), a mGluR5 antagonist, 30 mg/kg by i.p. and tested 20 minutes after injection. Audio stimulus was administered continuously for 60 seconds at 124 db. Observable results are shown in Table 14.

TABLE 14

| Doses | Wild running | Seizure | Respiratory arrest | Incidence |
|---|---|---|---|---|
| WT-Vehicle | 0/10 | 0/10 | 0/10 | 0% |
| Fmr1 KO1-Vehicle | 10/10 | 10/10 | 6/10 | 100% |
| Fmr1 KO1-MPEP | 0/10 | 0/10 | 0/10 | 0% |
| Fmr1 KO1-Compound 0.01 mg/kg | 10/10 | 10/10 | 7/10 | 100% |
| Fmr1 KO1-Compound 0.05 mg/kg | 10/10 | 8/10 | 5/10 | 100% |
| Fmr1 KO1-Compound 0.1 mg/kg | 4/10 | 5/10 | 4/10 | 40% |

Audiogenic seizure susceptibility was reduced to 40% in Fmr1 KO1 mice treated by (S)-3-amino-4-(difluoromethylenyl) cyclopent-1-ene-1-carboxylic acid at 0.1 mg/Kg.

CONCLUSION (S)-3-amino-4-(difluoromethylenyl) cyclopent-1-ene-1-carboxylic acid provided a significant ameliorating effect in both Fmr1 KO2 and Fmr1 KO1 phenotypes in multiple domains. Fmr1 KO2 and Fmr1 KO1 mice showed behavioral abnormalities in increased hyperactivity and repetitive behavior (FIGS. 1-4 and FIGS. 7-10). (S)-3-amino-4-(difluoromethylenyl) cyclopent-1-ene-1-carboxylic acid modulated the reversions of these behavioral abnormalities at concentrations 0.05 and 0.1 mg/Kg. Fmr1 KO2 animals showed increased anxiety-like behavior (AIM 1 FIG. 6). (S)-3-amino-4-(difluoromethylenyl) cyclopent-1-ene-1-carboxylic acid at 0.05 and 0.1 mg/Kg had a strong effect in decreasing their anxiety—latency to eat—to virtually control levels. Thus, (S)-3-amino-4-(difluoromethylenyl) cyclopent-1-ene-1-carboxylic acid showed strong restorative effects in this preclinical model of FX syndrome (AIM 1 FIG. 6). This summary of the data suggests that behavior abnormalities (i.e., altered hyperactivity, repetitive behaviors, activities of daily living and anxiety) were overall corrected by (S)-3-amino-4-(difluoromethylenyl) cyclopent-1-ene-1-carboxylic acid in the Fmr1 KO2 and Fmr1 KO2 models at 0.05 and 0.1 mg/Kg. Furthermore, epilepsy-like behavior (AGS) was also clearly altered in the Fmr1 KO1 mice (FVB background) and (S)-3-amino-4-(difluoromethylenyl) cyclopent-1-ene-1-carboxylic acid at 0.1 was effective in reducing seizures to 40%.

It should be understood that the examples and embodiments provided herein are exemplary examples and embodiments. Those skilled in the art will envision various modifications of the examples and embodiments that are consistent with the scope of the disclosure herein. Such modifications are intended to be encompassed by the claims.

What is claimed is:

1. A method of treating Fragile X syndrome comprising administering (S)-3-amino-4-(difluoromethylenyl)cyclopent-1-ene-1-carboxylic acid or a pharmaceutically acceptable salt thereof to a subject having Fragile X syndrome in an amount of from 0.001 mg to 75 mg.

2. The method of claim 1, wherein the subject is administered from 0.1 mg to 50 mg of (S)-3-amino-4-(difluoromethylenyl)cyclopent-1-ene-1-carboxylic acid or a pharmaceutically acceptable salt thereof.

3. The method of claim 1, wherein the subject is administered from 1 mg to 10 mg of (S)-3-amino-4-(difluoromethylenyl)cyclopent-1-ene-1-carboxylic acid or a pharmaceutically acceptable salt thereof.

4. The method of claim 1, wherein the total amount of (S)-3-amino-4-(difluoromethylenyl)cyclopent-1-ene-1-carboxylic acid or a pharmaceutically acceptable salt thereof administered to the subject in a twenty-four hour period is between 1 mg and 10 mg.

5. The method of claim 1, wherein (S)-3-amino-4-(difluoromethylenyl)cyclopent-1-ene-1-carboxylic acid or a pharmaceutically acceptable salt thereof is administered from one to four times a day.

6. The method of claim 1, wherein administering is accomplished via a route selected from the group consisting of oral, buccal, sublingual, rectal, topical, intranasal, ophthalmic, vaginal and parenteral.

7. The method of claim 1, wherein treating Fragile X syndrome ameliorates one or more symptoms of Fragile X syndrome.

8. A method of treating Fragile X syndrome comprising administering ((1S,3S)-3-amino-4-(difluoromethylidene) cyclopentane-1-carboxylic acid or a pharmaceutically acceptable salt thereof to a subject having Fragile X syndrome in an amount of from 0.01 mg to 750 mg.

9. The method of claim 8, wherein the subject is administered from 0.1 mg to 500 mg of (1S,3S)-3-amino-4-

(difluoromethylidene) cyclopentane-1-carboxylic acid or a pharmaceutically acceptable salt thereof.

10. The method of claim 8, wherein the subject is administered from 0.1 mg to 100 mg of (1S,3S)-3-amino-4-(difluoromethylidene) cyclopentane-1-carboxylic acid or a pharmaceutically acceptable salt thereof.

11. The method of claim 8, wherein the total amount of (1S,3S)-3-amino-4-(difluoromethylidene) cyclopentane-1-carboxylic acid or a pharmaceutically acceptable salt thereof administered to the subject in a twenty-four hour period is between 1 mg and 100 mg.

12. The method of claim 8, wherein (1S,3S)-3-amino-4-(difluoromethylidene) cyclopentane-1-carboxylic acid or a pharmaceutically acceptable salt thereof is administered from one to four times a day.

13. The method of claim 8, wherein administering is accomplished via a route selected from the group consisting of oral, buccal, sublingual, rectal, topical, intranasal, ophthalmic, vaginal and parenteral.

14. The method of claim 8, wherein treating Fragile X syndrome ameliorates one or more symptoms of Fragile X syndrome.

\* \* \* \* \*